United States Patent
Mayfield et al.

(10) Patent No.: US 10,047,371 B2
(45) Date of Patent: *Aug. 14, 2018

(54) COLOSTRUM/MILK PROTEIN COMPOSITIONS

(71) Applicant: The Regents of the University of California, Oakland, CA (US)

(72) Inventors: Stephen P. Mayfield, Cardiff, CA (US); Beth A. Rasala, San Diego, CA (US); Miller Tran, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/117,439

(22) PCT Filed: Feb. 19, 2015

(86) PCT No.: PCT/US2015/016596
§ 371 (c)(1),
(2) Date: Aug. 8, 2016

(87) PCT Pub. No.: WO2015/127061
PCT Pub. Date: Aug. 27, 2015

(65) Prior Publication Data
US 2016/0369291 A1    Dec. 22, 2016

Related U.S. Application Data

(60) Provisional application No. 61/942,024, filed on Feb. 19, 2014.

(51) Int. Cl.
| | | |
|---|---|---|
| *C12N 1/20* | (2006.01) | |
| *C12N 15/82* | (2006.01) | |
| *C07K 14/52* | (2006.01) | |
| *A23K 10/18* | (2016.01) | |
| *A23L 2/52* | (2006.01) | |
| *C07K 14/47* | (2006.01) | |
| *C07K 14/475* | (2006.01) | |
| *C07K 14/775* | (2006.01) | |
| *C12P 21/00* | (2006.01) | |
| *C07K 14/705* | (2006.01) | |
| *C07K 14/76* | (2006.01) | |
| *C12N 9/36* | (2006.01) | |
| *A23L 33/135* | (2016.01) | |

(52) U.S. Cl.
CPC .......... *C12N 15/8257* (2013.01); *A23K 10/18* (2016.05); *A23L 2/52* (2013.01); *A23L 33/135* (2016.08); *C07K 14/47* (2013.01); *C07K 14/475* (2013.01); *C07K 14/4705* (2013.01); *C07K 14/52* (2013.01); *C07K 14/70596* (2013.01); *C07K 14/76* (2013.01); *C07K 14/775* (2013.01); *C12N 9/2462* (2013.01); *C12N 15/8214* (2013.01); *C12P 21/00* (2013.01); *C12Y 302/01017* (2013.01); *A23V 2002/00* (2013.01)

(58) Field of Classification Search
CPC ............................ A23K 10/18; C07K 14/775
USPC ...................................................... 435/252.3
See application file for complete search history.

(56) References Cited

U.S. PATENT DOCUMENTS

| | | | |
|---|---|---|---|
| 4,778,759 A | 10/1988 | Szalay et al. | |
| 7,678,561 B2 | 3/2010 | Mayfield | |
| RE44,266 E | 6/2013 | Mayfield | |
| 9,732,351 B2* | 8/2017 | Mayfield ............ | C12N 15/8257 |
| 2002/0048577 A1 | 4/2002 | Bornstein et al. | |
| 2004/0022797 A1 | 2/2004 | Winslow et al. | |
| 2007/0134229 A1 | 6/2007 | Tian | |
| 2007/0298050 A1 | 12/2007 | Mayfield | |
| 2009/0098149 A1 | 4/2009 | Sayre | |
| 2010/0129394 A1 | 5/2010 | Mayfield | |
| 2010/0267139 A1 | 10/2010 | Kjems et al. | |
| 2012/0208279 A1 | 8/2012 | Vick et al. | |
| 2016/0257730 A1 | 9/2016 | Mayfield et al. | |
| 2016/0369291 A1 | 12/2016 | Mayfield et al. | |
| 2017/0342434 A1 | 11/2017 | Mayfield et al. | |

FOREIGN PATENT DOCUMENTS

| | | |
|---|---|---|
| EP | 0 195 680 A2 | 9/1986 |
| WO | WO 2015/126992 A1 | 8/2015 |
| WO | WO 2015/127061 A1 | 8/2015 |

OTHER PUBLICATIONS

U.S. Office Action dated Sep. 22, 2016 issued in U.S. Appl. No. 15/135,559.
PCT International Search Report and Written Opinion dated Jun. 26, 2015 issued in PCT/US2015/016460.
PCT International Preliminary Report on Patentability dated Sep. 1, 2016 issued in PCT/US2015/016460.
PCT International Search Report and Written Opinion dated Jun. 9, 2015 issued in PCT/US2015/016596.
PCT International Preliminary Report on Patentability dated Sep. 1, 2016 issued in PCT/US2015/016596.
Kerr et al., (2012) "Osteopontin," *UniProtKB*, P31096.2; pp. 1-7.
Artym, Jolanta et al., (2013) "Milk-derived proteins and peptides in clinical trials," *Postepy Hig Med Dosw* (online), 67:800-816.
Blom et al., (1999) "Sequence and Structure-based Prediction of Eukaryotic Protein Phosphorylation Sites," *J. Mol. Biol.*, 294:1351-1362.
Horiguchi et al., (2002) "Production of Recombinant Human Osteopontin Using Baculovirus Expression Systems," *Bulletin of Kanagawa Dental College*; 30:19P-21P.

(Continued)

*Primary Examiner* — Tekchand Saidha
(74) *Attorney, Agent, or Firm* — Weaver Austin Villeneuve & Sampson LLP

(57) ABSTRACT

Provided are colostrum and milk polypeptides recombinantly expressed in photosynthetic organisms containing colostrum and milk polypeptides, compositions comprising such organisms and methods for producing such organisms.

35 Claims, 19 Drawing Sheets

(56) References Cited

OTHER PUBLICATIONS

Larson et al., (2003) "Human serum amyloid A3 peptide enhances intestinal MUC3 expression and inhibits EPEC adherence," *Biochemical and Biophysical Research Communications*, 300:531-540.
Lis, Jolanta et al., (2013) "Proteins of human milk involved in immunological processes," *Postepy Hig Med Dosw* (online), 67:529-547, [English abstract].
Nazifi et al., (2008) "Evaluation of serum and milk amyloid A in some inflammatory diseases of cattle," *Iranian Journal of Veterinary Research*, Ser. No. 24, 9(3):222-226.
Smolenski, G. et al., (Jan. 2007) "Characterisation of host defence proteins in milk using a proteomic approach," *J Proteome Res*, 6(1):207-215, [PubMed abstract].
Wynn et al., (2012) "Minor Proteins, Including Growth Factors," *Advanced Dairy Chemistry: vol. 1A: Proteins: Basic Aspects*, 4th Edition, McSweeney and Fox (eds); pp. 317-335.
U.S. Notice of Allowance dated Apr. 28, 2017 issued in U.S. Appl. No. 15/135,559.
Ashkar et al., (1993) "In Vitro Phosphorylation of Mouse Osteopontin Expressed in *E. coli*," *Biochemical and Biophysical Research Communications*, 191(1):126-133.
Ashkar et al., (2000) "Eta-1 (Osteopontin): An Early Component of Type-1 (Cell-Mediated) Immunity,"*SCIENCE*, 287(5454):860-864 [Retrieved on Nov. 29, 2016 from http://science.sciencemag.org].
Hu et al., (1995) "A Biochemical Characterization of the Binding of Osteopontin to Integrins $\alpha_v\beta_1$ and $\alpha_v\gamma_5$," *The Journal of Biological Chemistry*, 270(44) Issue 3:26232-26238 [Retrieved on Dec. 14, 2016 from http://www.jbc.org].

\* cited by examiner

| Protein | Class | Function |
|---|---|---|
| mammary assoc. serum amyloid A3 | antimicrobial | Induces the expression of mucus to block pathogenic bacterial adhesion |
| osteopontin | bone strength anti-inflammatory | Extracellular matrix protein, binds calcium, major organic component of bone<br>Modulates immune function<br>Involved in wound repair |
| lysozyme C | anti-microbial | Hydrolyzes bacterial cell walls, inducing cell lysis. |
| alpha-lactalbumin | antimicrobial nutritional | Contains antimicrobial peptides<br>Prebiotic stimulation activities<br>Immuno-stimulatory effect<br>Enhances mineral absorption<br>Good source of tryptophan, first limited amino acid in infant formula |
| lactadherin | anti-inflammatory | Functions in the removal of apoptotic cells<br>Functions in intestinal epithelial homeostasis<br>Promotes mucosal healing<br>Treatment of bowel injuries |
| soluble CD14 | immuno-stimulation antimicrobial | Pattern recognition molecule that binds lipopolysaccharide (LPS) and initiates immune response to bacterial infections. |
| lingual antimicrobial peptide | antimicrobial | Broad-spectrum antimicrobial.<br>Inserts into cell membranes and causes cell lysis |
| cathelicidin-1 | antimicrobial | Broad-spectrum antimicrobial.<br>Inserts into cell membranes and causes cell lysis |

Fig. 1

```
AAG AAG TTC CAG CGC TGC GAG CTG GCC CGC ACC CTG AAG AAG CTG    < 45
 K   K   F   Q   R   C   E   L   A   R   T   L   K   K   L
GGC CTG GAC GGC TAC CGC GGC GTG TCC CTG GCC AAC TGG GTG TGC    < 90
 G   L   D   G   Y   R   G   V   S   L   A   N   W   V   C
CTG GCC CGC TGG GAG AGC AAC TAC AAC ACC CGC GCC ACC AAC TAC    < 135
 L   A   R   W   E   S   N   Y   N   T   R   A   T   N   Y
AAC CGC GGC GAC AAG AGC ACC GAC TAC GGC ATC TTC CAG ATC AAC    < 180
 N   R   G   D   K   S   T   D   Y   G   I   F   Q   I   N
AGC CGC TGG TGG TGC AAC GAC GGC AAG ACC CCC AAG GCC GTG AAC    < 225
 S   R   W   W   C   N   D   G   K   T   P   K   A   V   N
GCC TGC CGC ATC CCC TGC AGC GCC CTG CTG AAG GAC GAC ATC ACC    < 270
 A   C   R   I   P   C   S   A   L   L   K   D   D   I   T
CAG GCC GTG GCC TGC GCC AAG CGC GTC GTG CGC GAC CCC CAG GGC    < 315
 Q   A   V   A   C   A   K   R   V   V   R   D   P   Q   G
ATC AAG GCG TGG GTG GCG TGG CGC AAC AAG TGC CAG AAC CGC GAC    < 360
 I   K   A   W   V   A   W   R   N   K   C   Q   N   R   D
CTG CGC AGC TAC GTG CAG GGC TGC CGC GTG gga tcc GAC TAC AAG    < 405
 L   R   S   Y   V   Q   G   C   R   V   G   S   D   Y   K
GAC GAC GAC GAC AAG GAC GAG CTC TAA    < 432
 D   D   D   D   K   D   E   L   *
```

*Fig. 2*

```
TTC AGC GGC GAC TTC TGC GAC AGC AGC CAG TGC CTG CAC GGC    < 42
 F   S   G   D   F   C   D   S   S   Q   C   L   H   G
GGC ACC TGC CTG CTG AAC GAG GAC CGC ACC CCC CCC TTC TAC    < 84
 G   T   C   L   L   N   E   D   R   T   P   P   F   Y
TGC CTG TGC CCC GAG GGC TTC ACC GGC CTG CTG TGC AAC GAG    < 126
 C   L   C   P   E   G   F   T   G   L   L   C   N   E
ACC GAG CAC GGC CCC TGC TTC CCC AAC CCC TGC CAC AAC GAC    < 168
 T   E   H   G   P   C   F   P   N   P   C   H   N   D
GCC GAG TGC CAG GTG ACC GAC GAC AGC CAC CGC GGC GAC GTG    < 210
 A   E   C   Q   V   T   D   D   S   H   R   G   D   V
TTC ATC CAG TAC ATC TGC AAG TGC CCC CTG GGC TAC GTG GGC    < 252
 F   I   Q   Y   I   C   K   C   P   L   G   Y   V   G
ATC CAC TGC GAG ACC ACC TGC ACC TCG CCC CTG GGC ATG CAG    < 294
 I   H   C   E   T   T   C   T   S   P   L   G   M   Q
ACC GGC GCG ATC GCC GAC AGC CAG ATC AGC GCC AGC AGC ATG    < 336
 T   G   A   I   A   D   S   Q   I   S   A   S   S   M
CAC CTG GGC TTC ATG GGC CTG CAG CGC TGG GCC CCC GAG CTG    < 378
 H   L   G   F   M   G   L   Q   R   W   A   P   E   L
GCC CGC CTG CAC CAG ACC GGC ATC GTG AAC GCC TGG ACC AGC    < 420
 A   R   L   H   Q   T   G   I   V   N   A   W   T   S
GGC AAC TAC GAC AAG AAC CCG TGG ATT CAG GTG AAC CTG ATG    < 462
 G   N   Y   D   K   N   P   W   I   Q   V   N   L   M
CGC AAG ATG TGG GTC ACC GGC GTC GTG ACC CAG GGC GCC AGC    < 504
 R   K   M   W   V   T   G   V   V   T   Q   G   A   S
CGC GCC GGC AGC GCC GAG TAC CTG AAG ACC TTC AAG GTG GCC    < 546
 R   A   G   S   A   E   Y   L   K   T   F   K   V   A
TAC AGC ACC GAC GGC CGC CAG TTC CAG TTC ATC CAG GTG GCC    < 588
 Y   S   T   D   G   R   Q   F   Q   F   I   Q   V   A
GGC CGC AGC GGC GAC AAG ATC TTC ATC GGC AAC GTG AAC AAC    < 630
 G   R   S   G   D   K   I   F   I   G   N   V   N   N
```

*Fig. 3A*

```
TCC GGC CTG AAG ATC AAC CTG TTC GAC ACC CCC CTG GAG ACC   < 672
 S   G   L   K   I   N   L   F   D   T   P   L   E   T
CAG TAC GTG CGC CTG GTG CCC ATC ATC TGC CAC CGC GGC TGC   < 714
 Q   Y   V   R   L   V   P   I   I   C   H   R   G   C
ACC CTG CGC TTC GAG CTG CTG GGC TGC GAG CTG AAC GGC TGC   < 756
 T   L   R   F   E   L   L   G   C   E   L   N   G   C
ACC GAG CCG CTG GGC CTG AAG GAC AAC ACC ATC CCC AAC AAG   < 798
 T   E   P   L   G   L   K   D   N   T   I   P   N   K
CAG ATC ACC GCC TCC AGC TAC TAC AAG ACC TGG GGC CTG AGC   < 840
 Q   I   T   A   S   S   Y   Y   K   T   W   G   L   S
GCC TTC TCC TGG TTC CCC TAC TAC GCC CGC CTG GAC AAC CAG   < 882
 A   F   S   W   F   P   Y   Y   A   R   L   D   N   Q
GGC AAG TTC AAC GCG TGG ACC GCC CAG ACC AAC AGC GCC TCC   < 924
 G   K   F   N   A   W   T   A   Q   T   N   S   A   S
GAG TGG CTG CAG ATC GAC CTG GGC AGC CAG AAG CGC GTG ACC   < 966
 E   W   L   Q   I   D   L   G   S   Q   K   R   V   T
GGC ATC ATC ACC CAG GGC GCG CGC GAC TTC GGC CAC ATC CAG   < 1008
 G   I   I   T   Q   G   A   R   D   F   G   H   I   Q
TAC GTG GCC GCC TAC CGC GTG GCC TAC GGC GAC GAC GGC GTG   < 1050
 Y   V   A   A   Y   R   V   A   Y   G   D   D   G   V
ACC TGG ACC GAG TAC AAG GAC CCC GGC GCC AGC GAG AGC AAG   < 1092
 T   W   T   E   Y   K   D   P   G   A   S   E   S   K
ATC TTC CCG GGC AAC ATG GAC AAC AAC AGC CAC AAG AAG AAC   < 1134
 I   F   P   G   N   M   D   N   N   S   H   K   K   N
ATC TTC GAG ACC CCC TTC CAG GCC CGC TTC GTG CGC ATC CAG   < 1176
 I   F   E   T   P   F   Q   A   R   F   V   R   I   Q
CCC GTG GCC TGG CAC AAC CGC ATC ACC CTG CGC GTG GAG CTG   < 1218
 P   V   A   W   H   N   R   I   T   L   R   V   E   L
CTG GGC TGC ggc ggc gga gga tcc GAC TAC AAG GAC GAC GAC   < 1260
 L   G   C   G   G   G   G   S   D   Y   K   D   D   D
GAC AAG GAC GAG CTC TAA   < 1278
 D   K   D   E   L   *
```

*Fig. 3B*

```
CTGCCCGTGAAGCCCACCAGCAGCGGCAGCAGCGAGGAGAAGCAGCTGAACAACAAGTAC    < 60
  L  P  V  K  P  T  S  S  G  S  S  E  E  K  Q  L  N  N  K  Y
CCCGACGCCGTGGCCACCTGGCTGAAGCCCGACCCCAGCCAGAAGCAGACCTTCCTGGCC    < 120
   P  D  A  V  A  T  W  L  K  P  D  P  S  Q  K  Q  T  F  L  A
CCCCAGAACAGCGTGTCCTCCGAGGAGACCGACGACAACAAGCAGAACACCCTGCCCAGC    < 180
    P  Q  N  S  V  S  S  E  E  T  D  D  N  K  Q  N  T  L  P  S
AAGAGCAACGAGAGCCCCGAGCAGACCGACGACCTGGACGACGACGACGACAACAGCCAG    < 240
     K  S  N  E  S  P  E  Q  T  D  D  L  D  D  D  D  D  N  S  Q
GACGTGAACAGCAACGACAGCGACGACGCCGAGACCACCGACGACCCCGACCACAGCGAC    < 300
      D  V  N  S  N  D  S  D  D  A  E  T  T  D  D  P  D  H  S  D
GAGAGCCACCACTCCGACGAGTCGGACGAGGTGGACTTCCCCACCGACATCCCCACCATC    < 360
       E  S  H  H  S  D  E  S  D  E  V  D  F  P  T  D  I  P  T  I
GCGGTGTTCACCCCCTTCATCCCGACCGAGAGCGCCAACGACGGCCGCGGCGACAGCGTG    < 420
        A  V  F  T  P  F  I  P  T  E  S  A  N  D  G  R  G  D  S  V
GCCTACGGCCTGAAGTCCCGCAGCAAGAAGTTCCGCCGCAGCAACGTGCAGTCGCCCGAC    < 480
         A  Y  G  L  K  S  R  S  K  K  F  R  R  S  N  V  Q  S  P  D
GCCACCGAGGAGGACTTCACCTCCCACATCGAGTCGGAGGAGATGCACGACGCCCCCAAG    < 540
          A  T  E  E  D  F  T  S  H  I  E  S  E  E  M  H  D  A  P  K
AAGACCAGCCAGCTGACCGACCACTCCAAGGAGACCAACAGCTCCGAGCTGAGCAAGGAG    < 600
           K  T  S  Q  L  T  D  H  S  K  E  T  N  S  S  E  L  S  K  E
CTGACCCCCAAGGCCAAGGACAAGAACAAGCACAGCAACCTGATCGAGAGCCAGGAGAAC    < 660
            L  T  P  K  A  K  D  K  N  K  H  S  N  L  I  E  S  Q  E  N
AGCAAGCTGTCCCAGGAGTTCCACAGCCTGGAGGACAAGCTGGACCTGGACCACAAGAGC    < 720
             S  K  L  S  Q  E  F  H  S  L  E  D  K  L  D  L  D  H  K  S
GAGGAGGACAAGCACCTGAAGATCCGCATCAGCCACGAGCTGGACAGCGCCTCCAGCGAG    < 780
              E  E  D  K  H  L  K  I  R  I  S  H  E  L  D  S  A  S  S  E
GTGAACggcggcggaggatccGACTACAAGGACGACGACGACAAGGACGAGCTCTAA    < 837
               V  N  G  G  G  S  D  Y  K  D  D  D  D  K  D  E  L  *
```

*Fig. 4*

```
GAGCAGCTGACCAAGTGCGAGGTGTTCCGCGAGCTGAAGGACCTGAAGGGCTACGGCGGC   < 60
  E   Q   L   T   K   C   E   V   F   R   E   L   K   D   L   K   G   Y   G   G
GTGTCGCTGCCCGAGTGGGTGTGCACCACCTTCCACACCAGCGGCTACGACACCCAGGCG   < 120
  V   S   L   P   E   W   V   C   T   T   F   H   T   S   G   Y   D   T   Q   A
ATCGTGCAGAACAACGACAGCACCGAGTACGGCCTGTTCCAGATCAACAACAAGATCTGG   < 180
  I   V   Q   N   N   D   S   T   E   Y   G   L   F   Q   I   N   N   K   I   W
TGCAAGGACGACCAGAACCCCCACAGCAGCAACATCTGCAACATCAGCTGCGACAAGTTC   < 240
  C   K   D   D   Q   N   P   H   S   S   N   I   C   N   I   S   C   D   K   F
CTGGACGACGACCTGACCGACGACATTATGTGCGTGAAGAAGATCCTGGACAAGGTGGGC   < 300
  L   D   D   D   L   T   D   D   I   M   C   V   K   K   I   L   D   K   V   G
ATCAACTACTGGCTGGCCCACAAGGCCCTGTGCAGCGAGAAGCTGGACCAGTGGCTGTGC   < 360
  I   N   Y   W   L   A   H   K   A   L   C   S   E   K   L   D   Q   W   L   C
GAGAAGCTGggcggcggaggatccGACTACAAGGACGACGACGACAAGGACGAGCTCTAA  < 420
  E   K   L   G   G   G   S   D   Y   K   D   D   D   D   K   D   E   L   *
```

*Fig. 5*

```
CAG GCC CTG AGC TAC CGC GAG GCC GTG CTG CGC GCC GTG GAC CAG     < 45
 Q   A   L   S   Y   R   E   A   V   L   R   A   V   D   Q
CTG AAC GAG CAG AGC AGC GAG CCC AAC ATC TAC CGC CTG CTG GAG     < 90
 L   N   E   Q   S   S   E   P   N   I   Y   R   L   L   E
CTG GAC CAG CCC CCC CAG GAC GAC GAG GAC CCC GAC AGC CCC AAG     < 135
 L   D   Q   P   P   Q   D   D   E   D   P   D   S   P   K
CGC GTG TCC TTC CGC GTG AAG GAG ACC GTG TGC AGC CGC ACC ACC     < 180
 R   V   S   F   R   V   K   E   T   V   C   S   R   T   T
CAG CAG CCC CCC GAG CAG TGC GAC TTC AAG GAG AAC GGC CTG CTG     < 225
 Q   Q   P   P   E   Q   C   D   F   K   E   N   G   L   L
AAG CGC TGC GAG GGC ACC GTG ACC CTG GAC CAG GTG CGC GGC AAC     < 270
 K   R   C   E   G   T   V   T   L   D   Q   V   R   G   N
TTC GAC ATC ACC TGC AAC AAC CAC CAG AGC ATC CGC ATC ACC AAG     < 315
 F   D   I   T   C   N   N   H   Q   S   I   R   I   T   K
CAG CCG TGG GCC CCC CCG CAG GCC GCC CGC CTG TGC CGC ATC GTC     < 360
 Q   P   W   A   P   P   Q   A   A   R   L   C   R   I   V
GTG ATC CGC GTG TGC CGC ggc ggc gga gga tcc GAC TAC AAG GAC     < 405
 V   I   R   V   C   R   G   G   G   G   S   D   Y   K   D
GAC GAC GAC AAG GAC GAG CTC TAA     < 429
 D   D   D   K   D   E   L   *
```

*Fig. 6*

```
GTGCGCAACAGCCAGAGCTGCCGCCGCAACAAGGGCATCTGCGTGCCCATCCGCTGCCCC   < 60
  V   R   N   S   Q   S   C   R   R   N   K   G   I   C   V   P   I   R   C   P
GGCAGCATGCGCCAGATCGGCACCTGCCTGGGCGCCCAGGTGAAGTGCTGCCGCCGCAAG   < 120
  G   S   M   R   Q   I   G   T   C   L   G   A   Q   V   K   C   C   R   R   K
ggcggcggaggatccGACTACAAGGACGACGACGACAAGGACGAGCTCTAA   < 171
  G   G   G   G   S   D   Y   K   D   D   D   D   K   D   E   L   *
```

*Fig. 7*

```
GACACCACCGAGCCCTGCGAGCTGGACGACGACGACTTCCGCTGCGTGTGCAACTTCACC    < 60
  D   T   T   E   P   C   E   L   D   D   D   D   F   R   C   V   C   N   F   T
GACCCCAAGCCCGACTGGTCCAGCGCCGTGCAGTGCATGGTGGCCGTGGAGGTGGAGATC    < 120
  D   P   K   P   D   W   S   S   A   V   Q   C   M   V   A   V   E   V   E   I
AGCGCCGGCGGCCGCAGCCTGGAGCAGTTCCTGAAGGGCGCGGACACCAACCCGAAGCAG    < 180
  S   A   G   G   R   S   L   E   Q   F   L   K   G   A   D   T   N   P   K   Q
TACGCCGACACCATCAAGGCGCTGCGCGTGCGCCGCCTGAAGCTGGGCGCGGCCCAGGTG    < 240
  Y   A   D   T   I   K   A   L   R   V   R   R   L   K   L   G   A   A   Q   V
CCCGCGCAGCTGCTGGTGGCGGTGCTGCGCGCCCTGGGCTACTCGCGCCTGAAGGAGCTG    < 300
  P   A   Q   L   L   V   A   V   L   R   A   L   G   Y   S   R   L   K   E   L
ACCCTGGAGGACCTGGAGGTGACCGGCCCCACCCCCCCGACCCCCCTGGAGGCCGCGGGC    < 360
  T   L   E   D   L   E   V   T   G   P   T   P   P   T   P   L   E   A   A   G
CCCGCCCTGACCACCCTGAGCCTGCGCAACGTGTCCTGGACCACCGGCGGCGCCTGGCTG    < 420
  P   A   L   T   T   L   S   L   R   N   V   S   W   T   T   G   G   A   W   L
GGCGAGCTGCAGCAGTGGCTGAAGCCCGGCCTGCGCGTGCTGAACATCGCCCAGGCCCAC    < 480
  G   E   L   Q   Q   W   L   K   P   G   L   R   V   L   N   I   A   Q   A   H
AGCCTGGCCTTCCCCGTGCGCGGGCCTGAGCACCTTCGAGGCGCTGACCACCCTGGACCTG    < 540
  S   L   A   F   P   C   A   G   L   S   T   F   E   A   L   T   T   L   D   L
AGCGACAACCCCTCGCTGGGCGACAGCGGCCTGATGGCCGCCCTGTGCCCCAACAAGTTC    < 600
  S   D   N   P   S   L   G   D   S   G   L   M   A   A   L   C   P   N   K   F
CCCGCGCTGCAGTACCTGGCGCTGCGCAACGCCGGCATGGAGACCCCCAGCGGCGTGTGC    < 660
  P   A   L   Q   Y   L   A   L   R   N   A   G   M   E   T   P   S   G   V   C
GCCGCGCTGGCCGCCGCCCGCGTGCAGCCCCAGTCGCTGGACCTGTCCCACAACTCCCTG    < 720
  A   A   L   A   A   A   R   V   Q   P   Q   S   L   D   L   S   H   N   S   L
CGCGTGACCGCGCCCGGCGCCACCCGCTGCGTGTGGCCCAGCGCCCTGCGCAGCCTGAAC    < 780
  R   V   T   A   P   G   A   T   R   C   V   W   P   S   A   L   R   S   L   N
CTGAGCTTCGCCGGCCTGGAGCAGGTGCCCAAGGGCCTGCCCCCCAAGCTGAGCGTGCTG    < 840
  L   S   F   A   G   L   E   Q   V   P   K   G   L   P   P   K   L   S   V   L
GACCTGAGCTGCAACAAGCTGAGCCGCGAGCCGCGCCGCGACGAGCTGCCCGAGGTGAAC    < 900
  D   L   S   C   N   K   L   S   R   E   P   R   R   D   E   L   P   E   V   N
GACCTGACCCTGGACGGCAACCCCTTCCTGGACCCGGGCGCCCTGCAGCACCAGAACGAC    < 960
  D   L   T   L   D   G   N   P   F   L   D   P   G   A   L   Q   H   Q   N   D
CCCATGATCTCCGGCGTGGTGCCCGCCTGCGCCCGCTCGGCCCTGACCATGGGCGTGTCG    <
1020
  P   M   I   S   G   V   V   P   A   C   A   R   S   A   L   T   M   G   V   S
GGCGCGCTGGCCCTGCTGCAGGGCGCGCGCGGCTTCGCCggcggcggaggatccGACTAC    <
1080
  G   A   L   A   L   L   Q   G   A   R   G   F   A   G   G   G   S   D   Y
AAGGACGACGACGACAAGGACGAGCTCTAA    < 1110
  K   D   D   D   D   K   D   E   L   *
```

*Fig. 8*

```
GACACCACCCTGACCAACGTGACCGACCCCAGCCTGGACCTGACCGCCCTGAGCTGGGAG    < 60
  D  T  T  L  T  N  V  T  D  P  S  L  D  L  T  A  L  S  W  E
GTGGGCTGCGGCGCCCCCGTGCCCCTGGTCAAGTGCGACGAGAACAGCCCCTACCGCACC    < 120
  V  G  C  G  A  P  V  P  L  V  K  C  D  E  N  S  P  Y  R  T
ATCACCGGCGACTGCAACAACCGCCGCTCCCCCGCCCTGGGCGCCGCCAACCGCGCCCTG    < 180
  I  T  G  D  C  N  N  R  R  S  P  A  L  G  A  A  N  R  A  L
GCCCGCTGGCTGCCCGCCGAGTACGAGGACGGCCTGGCCCTGCCCTTCGGCTGGACCCAG    < 240
  A  R  W  L  P  A  E  Y  E  D  G  L  A  L  P  F  G  W  T  Q
CGCAAGACCCGCAACGGCTTCCGCGTGCCGCTGGCCCGCGAGGTGTCCAACAAGATCGTG    < 300
  R  K  T  R  N  G  F  R  V  P  L  A  R  E  V  S  N  K  I  V
GGCTACCTGGACGAGGAGGGCGTGCTGGACCAGAACCGCAGCCTGCTGTTCATGCAGTGG    < 360
  G  Y  L  D  E  E  G  V  L  D  Q  N  R  S  L  L  F  M  Q  W
GGCCAGATCGTGGACCACGACCTGGACTTCGCCCCCGAGACCGAGCTGGGCAGCAACGAG    < 420
  G  Q  I  V  D  H  D  L  D  F  A  P  E  T  E  L  G  S  N  E
CACAGCAAGACCCAGTGCGAGGAGTACTGCATCCAGGGCGACAACTGCTTCCCCATCATG    < 480
  H  S  K  T  Q  C  E  E  Y  C  I  Q  G  D  N  C  F  P  I  M
TTCCCCAAGAACGACCCCAAGCTGAAGACCCAGGGCAAGTGCATGCCGTTCTTCCGCGCC    < 540
  F  P  K  N  D  P  K  L  K  T  Q  G  K  C  M  P  F  F  R  A
GGCTTCGTGTGCCCCACCCCCCCGTACCAGAGCCTGGCGCGCGAGCAGATCAACGCCGTG    < 600
  G  F  V  C  P  T  P  P  Y  Q  S  L  A  R  E  Q  I  N  A  V
ACCTCGTTCCTGGACGCCAGCCTGGTGTACGGCAGCGAGCCCTCCCTGGCCTCCCGCCTG    < 660
  T  S  F  L  D  A  S  L  V  Y  G  S  E  P  S  L  A  S  R  L
CGCAACCTGTCCAGCCCCCTGGGCCTGATGGCCGTGAACCAGGAGGCCTGGGACCACGGC    < 720
  R  N  L  S  S  P  L  G  L  M  A  V  N  Q  E  A  W  D  H  G
CTGGCCTACCTGCCCTTCAACAACAAGAAGCCCAGCCCCTGCGAGTTCATCAACACCACC    < 780
  L  A  Y  L  P  F  N  N  K  K  P  S  P  C  E  F  I  N  T  T
GCCCGCGTGCCCTGCTTCCTGGCGGGCGACTTCCGCGCGTCGGAGCAGATCCTGCTGGCC    < 840
  A  R  V  P  C  F  L  A  G  D  F  R  A  S  E  Q  I  L  L  A
ACCGCCCACACCCTGCTGCTGCGCGAGCACAACCGCCTGGCCCGCGAGCTGAAGAAGCTG    < 900
  T  A  H  T  L  L  L  R  E  H  N  R  L  A  R  E  L  K  K  L
AACCCCCACTGGAACGGCGAGAAGCTGTACCAGGAGGCGCGCAAGATCCTGGGCGCCTTC    < 960
  N  P  H  W  N  G  E  K  L  Y  Q  E  A  R  K  I  L  G  A  F
```

*Fig. 9A*

```
ATCCAGATCATCACCTTCCGCGACTACCTGCCGATCGTGCTGGGCTCCGAGATGCAGAAG    < 1020
   I  Q  I  I  T  F  R  D  Y  L  P  I  V  L  G  S  E  M  Q  K
TGGATTCCGCCCTACCAGGGCTACAACAACAGCGTGGACCCCCGCATCAGCAACGTGTTC    < 1080
   W  I  P  P  Y  Q  G  Y  N  N  S  V  D  P  R  I  S  N  V  F
ACCTTCGCCTTCCGCTTCGGCCACATGGAGGTGCCCAGCACCGTGTCCCGCCTGGACGAG    < 1140
   T  F  A  F  R  F  G  H  M  E  V  P  S  T  V  S  R  L  D  E
AACTACCAGCCCTGGGGCCCCGAGGCGGAGCTGCCCCTGCACACCCTGTTCTTCAACACC    < 1200
   N  Y  Q  P  W  G  P  E  A  E  L  P  L  H  T  L  F  F  N  T
TGGCGCATCATCAAGGACGGCGGCATCGACCCCCTGGTGCGCGGCCTGCTGGCGAAGAAG    < 1260
   W  R  I  I  K  D  G  G  I  D  P  L  V  R  G  L  L  A  K  K
TCCAAGCTGATGAACCAGGACAAGATGGTCACCAGCGAGCTGCGCAACAAGCTGTTCCAG    < 1320
   S  K  L  M  N  Q  D  K  M  V  T  S  E  L  R  N  K  L  F  Q
CCCACCCACAAGATCCACGGCTTCGACCTGGCCGCCATCAACCTGCAGCGCTGCCGCGAC    < 1380
   P  T  H  K  I  H  G  F  D  L  A  A  I  N  L  Q  R  C  R  D
CACGGCATGCCCGGCTACAACTCGTGGCGCGGCTTCTGCGGCCTGAGCCAGCCCAAGACC    < 1440
   H  G  M  P  G  Y  N  S  W  R  G  F  C  G  L  S  Q  P  K  T
CTGAAGGGCCTGCAGACCGTGCTGAAGAACAAGATCCTGGCCAAGAAGCTGATGGACCTG    < 1500
   L  K  G  L  Q  T  V  L  K  N  K  I  L  A  K  K  L  M  D  L
TACAAGACCCCCGACAACATCGACATCTGGATCGGCGGCAACGCCGAGCCCATGGTGGAG    < 1560
   Y  K  T  P  D  N  I  D  I  W  I  G  G  N  A  E  P  M  V  E
CGCGGCCGCGTGGGCCCGCTGCTGGCCTGCCTGCTGGGCCGCCAGTTCCAGCAGATCCGC    < 1620
   R  G  R  V  G  P  L  L  A  C  L  L  G  R  Q  F  Q  Q  I  R
GACGGCGACCGCTTCTGGTGGGAGAACCCCGGCGTGTTCACCGAGAAGCAGCGCGACAGC    < 1680
   D  G  D  R  F  W  W  E  N  P  G  V  F  T  E  K  Q  R  D  S
CTGCAGAAGGTGTCCTTCAGCCGCCTGATCTGCGACAACACCCACATCACCAAGGTGCCG    < 1740
   L  Q  K  V  S  F  S  R  L  I  C  D  N  T  H  I  T  K  V  P
CTGCACGCCTTCCAGGCCAACAACTACCCCCACGACTTCGTGGACTGCTCCACCGTGGAC    < 1800
   L  H  A  F  Q  A  N  N  Y  P  H  D  F  V  D  C  S  T  V  D
AAGCTGGACCTGTCCCCGTGGGCCAGCCGCGAGAACggatccGACTACAAGGACGACGAC    < 1860
   K  L  D  L  S  P  W  A  S  R  E  N  G  S  D  Y  K  D  D  D
GACAAGGACGAGCTCTAA    < 1878
   D  K  D  E  L  *
```

*Fig. 9B*

```
ATGTGGGGCACCTTCCTGAAGGAGGCGGGCCAGGGCGCGAAGGACATGTGGCGC  < 60
 M  W  G  T  F  L  K  E  A  G  Q  G  A  K  D  M  W  R
GCCTACCAGGACATGAAGGAGGCCAACTACCGCGGCGCGGACAAGTACTTCCACGCCCGC  < 120
 A  Y  Q  D  M  K  E  A  N  Y  R  G  A  D  K  Y  F  H  A  R
GGCAACTACGACGCGGCCCGCCGCGGCCCCGGCGGCGCGTGGGCGGCGAAGGTGATCAGC  < 180
  G  N  Y  D  A  A  R  R  G  P  G  G  A  W  A  A  K  V  I  S
AACGCGCGCGAGACCATCCAGGGCATCACCGACCCCCTGTTCAAGGGCATGACCCGCGAC  < 240
  N  A  R  E  T  I  Q  G  I  T  D  P  L  F  K  G  M  T  R  D
CAGGTGCGCGAGGACAGCAAGGCCGACCAGTTCGCGAACGAGTGGGGCCGCAGCGGCAAG  < 300
  Q  V  R  E  D  S  K  A  D  Q  F  A  N  E  W  G  R  S  G  K
GACCCCAACCACTTCCGCCCCGCGGGCCTGCCCGACAAGTACTAG  < 351
  D  P  N  H  F  R  P  A  G  L  P  D  K  Y  *
```

*Fig. 10*

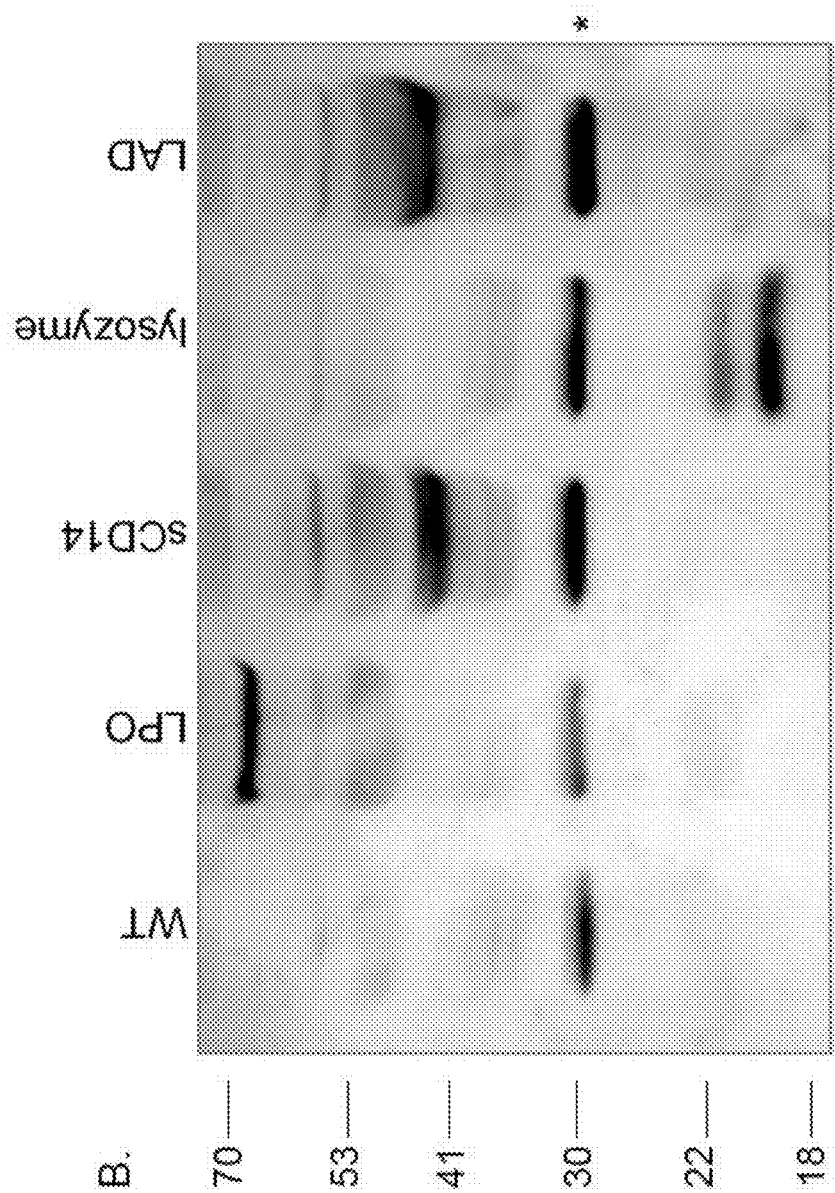
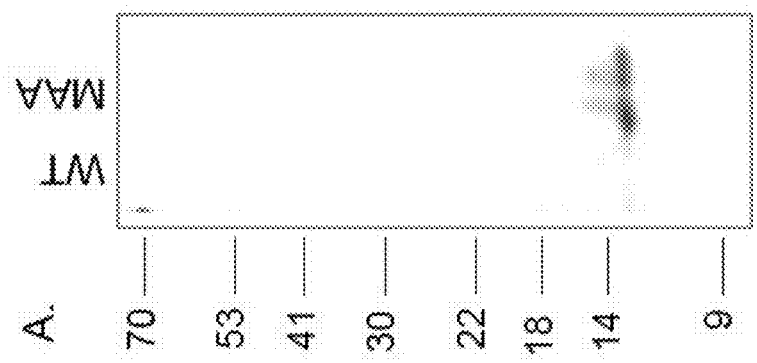
Fig. 11A-B

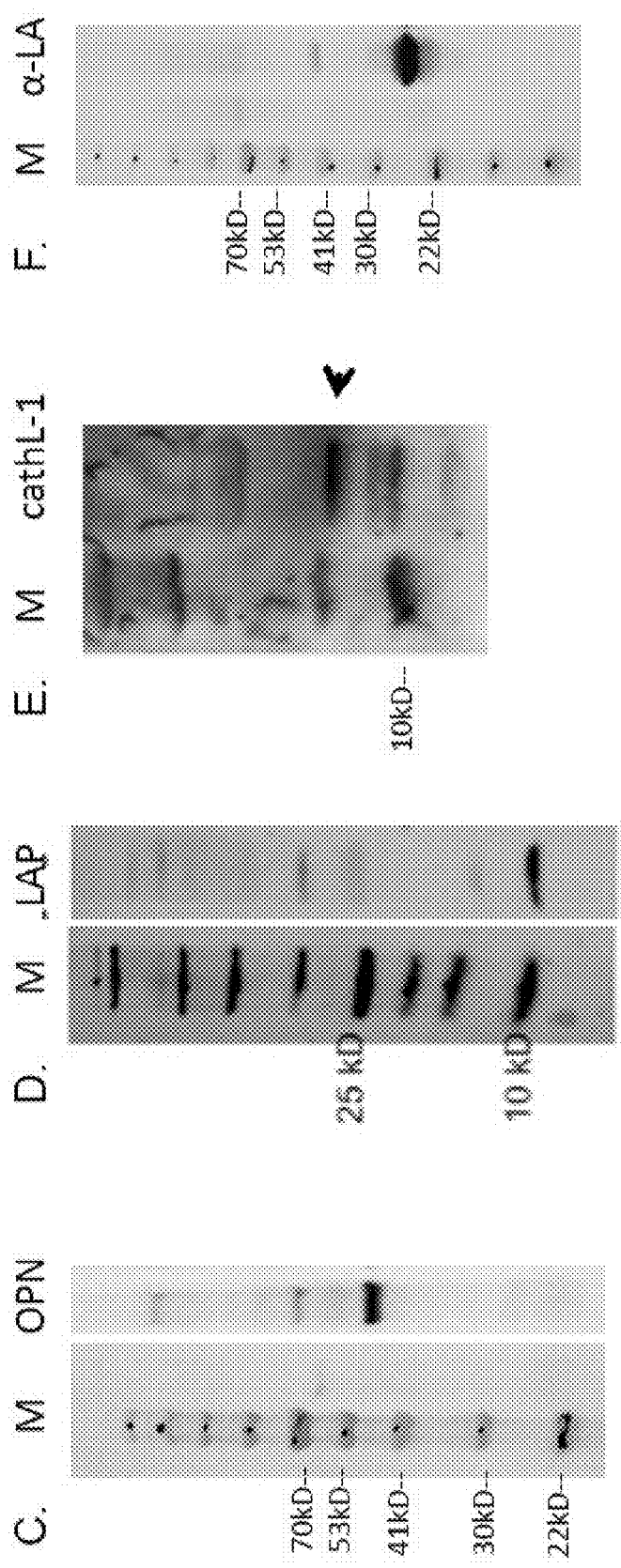
Fig. 11C-F

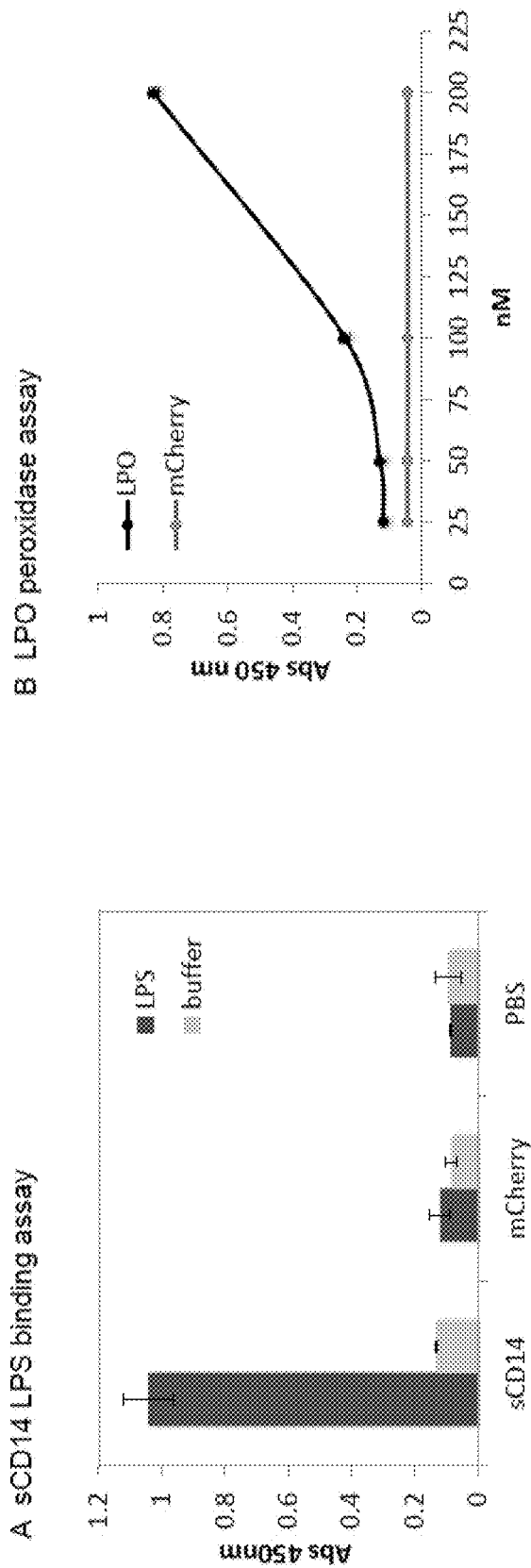
Fig. 14A-B

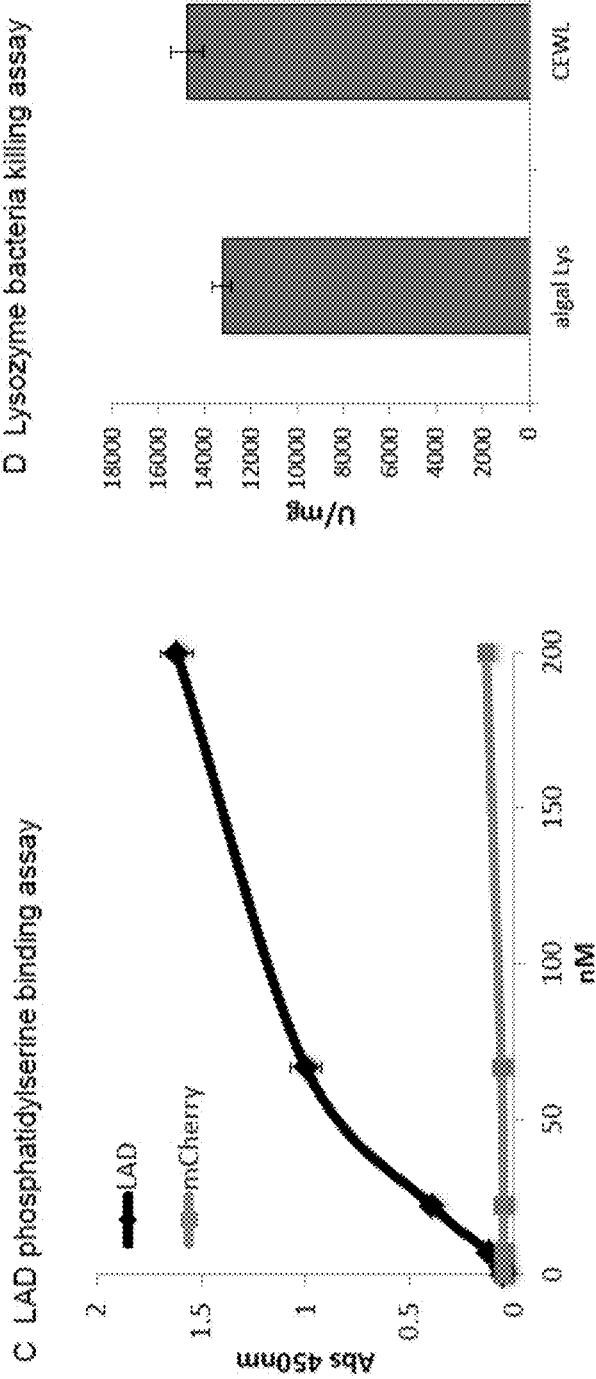
Fig. 14C-D

SEQUENCE LISTING

<160> NUMBER OF SEQ ID NOS: 65

<210> SEQ ID NO 1
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gattacaaag atgatgacga taaaagttta cctgtaaaac caacatcatc aggttcatca      60
gaagaaaaac aattaaataa taaatatcca gatgctgttg caatttggtt aaaacctgat     120
ccatcacaaa aacaaacatt tttaacacca caaaattcag tatcatcaga agaaacagat     180
gataataaac aaaatacatt accatcaaaa tcaaatgaat caccagaaca aactgatgat     240
ttagatgatg atgatgataa ttcacaagat gttaattcaa atgattcaga tgatgctgaa     300
acaacagatg atcctgatca ttcagatgaa tcacatcact cagatgaatc agatgaagtt     360
gattttccta cagatattcc aactattgct gttttttacac catttattcc tacagaatca     420
gctaatgatg gtcgtggtga ttcagtagct tatggtttaa aatcacgttc aaaaaaattt     480
cgtcgttcaa atgtacaatc accagatgct actgaagaag atttcacatc acacattgaa     540
tcagaagaaa tgcacgatgc tccaaaaaaa acttcacaat taacagatca ttcaaaagaa     600
actaattcat cagaattatc aaaagaatta acaccaaaag ctaaagataa aaataaacat     660
tcaaatttaa ttgaatcaca agaaaattca aaattatcac aagaatttca ttcattagaa     720

```
gataaattag atttagatca caaatcagaa gaagataaac atttaaaaat tcgtatttca      780
catgaattag attcagcttc atcagaagtt aat                                  813
```

<210> SEQ ID NO 2
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Tyr Lys Asp Asp Asp Lys Ser Leu Pro Val Lys Pro Thr Ser
1               5                   10                  15

Ser Gly Ser Ser Glu Glu Lys Gln Leu Asn Asn Lys Tyr Pro Asp Ala
                20                  25                  30

Val Ala Ile Trp Leu Lys Pro Asp Pro Ser Gln Lys Gln Thr Phe Leu
            35                  40                  45

Thr Pro Gln Asn Ser Val Ser Glu Glu Thr Asp Asp Asn Lys Gln
        50                  55                  60

Asn Thr Leu Pro Ser Lys Ser Asn Glu Ser Pro Glu Gln Thr Asp Asp
65                  70                  75                  80

Leu Asp Asp Asp Asp Asn Ser Gln Asp Val Asn Ser Asn Asp Ser
                    85                  90                  95

Asp Asp Ala Glu Thr Thr Asp Pro Asp His Ser Asp Glu Ser His
                100                 105                 110

His Ser Asp Glu Ser Asp Glu Val Asp Phe Pro Thr Asp Ile Pro Thr
            115                 120                 125

Ile Ala Val Phe Thr Pro Phe Ile Pro Thr Glu Ser Ala Asn Asp Gly
        130                 135                 140

Arg Gly Asp Ser Val Ala Tyr Gly Leu Lys Ser Arg Ser Lys Lys Phe
145                 150                 155                 160

Arg Arg Ser Asn Val Gln Ser Pro Asp Ala Thr Glu Glu Asp Phe Thr
                165                 170                 175

Ser His Ile Glu Ser Glu Glu Met His Asp Ala Pro Lys Lys Thr Ser
            180                 185                 190

Gln Leu Thr Asp His Ser Lys Glu Thr Asn Ser Ser Glu Leu Ser Lys
        195                 200                 205

Glu Leu Thr Pro Lys Ala Lys Asp Lys Asn Lys His Ser Asn Leu Ile
    210                 215                 220

Glu Ser Gln Glu Asn Ser Lys Leu Ser Gln Glu Phe His Ser Leu Glu
225                 230                 235                 240

Asp Lys Leu Asp Leu Asp His Lys Ser Glu Glu Asp Lys His Leu Lys
                245                 250                 255

Ile Arg Ile Ser His Glu Leu Asp Ser Ala Ser Ser Glu Val Asn
            260                 265                 270

<210> SEQ ID NO 3
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Tyr Lys Asp Asp Asp Asp Lys Ser Phe Ser Gly Asp Phe Cys Asp
1               5                   10                  15

```
Ser Ser Gln Cys Leu His Gly Gly Thr Cys Leu Leu Asn Glu Asp Arg
             20                  25                  30

Thr Pro Pro Phe Tyr Cys Leu Cys Pro Glu Gly Phe Thr Gly Leu Leu
             35                  40                  45

Cys Asn Glu Thr Glu His Gly Pro Cys Phe Pro Asn Pro Cys His Asn
 50                  55                  60

Asp Ala Glu Cys Gln Val Thr Asp Asp Ser His Arg Gly Asp Val Phe
65                   70                  75                  80

Ile Gln Tyr Ile Cys Lys Cys Pro Leu Gly Tyr Val Gly Ile His Cys
                 85                  90                  95

Glu Thr Thr Cys Thr Ser Pro Leu Gly Met Gln Thr Gly Ala Ile Ala
                100                 105                 110

Asp Ser Gln Ile Ser Ala Ser Ser Met His Leu Gly Phe Met Gly Leu
             115                 120                 125

Gln Arg Trp Ala Pro Glu Leu Ala Arg Leu His Gln Thr Gly Ile Val
130                 135                 140

Asn Ala Trp Thr Ser Gly Asn Tyr Asp Lys Asn Pro Trp Ile Gln Val
145                 150                 155                 160

Asn Leu Met Arg Lys Met Trp Val Thr Gly Val Val Thr Gln Gly Ala
                165                 170                 175

Ser Arg Ala Gly Ser Ala Glu Tyr Leu Lys Thr Phe Lys Val Ala Tyr
             180                 185                 190

Ser Thr Asp Gly Arg Gln Phe Gln Phe Ile Gln Val Ala Gly Arg Ser
         195                 200                 205

Gly Asp Lys Ile Phe Ile Gly Asn Val Asn Asn Ser Gly Leu Lys Ile
     210                 215                 220

Asn Leu Phe Asp Thr Pro Leu Glu Thr Gln Tyr Val Arg Leu Val Pro
225                 230                 235                 240

Ile Ile Cys His Arg Gly Cys Thr Leu Arg Phe Glu Leu Leu Gly Cys
                245                 250                 255

Glu Leu Asn Gly Cys Thr Glu Pro Leu Gly Leu Lys Asp Asn Thr Ile
             260                 265                 270

Pro Asn Lys Gln Ile Thr Ala Ser Ser Tyr Tyr Lys Thr Trp Gly Leu
         275                 280                 285

Ser Ala Phe Ser Trp Phe Pro Tyr Tyr Ala Arg Leu Asp Asn Gln Gly
     290                 295                 300

Lys Phe Asn Ala Trp Thr Ala Gln Thr Asn Ser Ala Ser Glu Trp Leu
305                 310                 315                 320

Gln Ile Asp Leu Gly Ser Gln Lys Arg Val Thr Gly Ile Ile Thr Gln
                325                 330                 335

Gly Ala Arg Asp Phe Gly His Ile Gln Tyr Val Ala Ala Tyr Arg Val
             340                 345                 350

Ala Tyr Gly Asp Asp Gly Val Thr Trp Thr Glu Tyr Lys Asp Pro Gly
         355                 360                 365

Ala Ser Glu Ser Lys Ile Phe Pro Gly Asn Met Asp Asn Asn Ser His
     370                 375                 380

Lys Lys Asn Ile Phe Glu Thr Pro Phe Gln Ala Arg Phe Val Arg Ile
385                 390                 395                 400

Gln Pro Val Ala Trp His Asn Arg Ile Thr Leu Arg Val Glu Leu Leu
                405                 410                 415

Gly Cys
```

<210> SEQ ID NO 4
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
aagaagttcc agcgctgcga gctggcccgc accctgaaga agctgggcct ggacggctac      60
cgcggcgtgt ccctggccaa ctgggtgtgc ctggcccgct gggagagcaa ctacaacacc     120
cgcgccacca actacaaccg cggcgacaag agcaccgact acggcatctt ccagatcaac     180
agccgctggt ggtgcaacga cggcaagacc cccaaggccg tgaacgcctg ccgcatcccc     240
tgcagcgccc tgctgaagga cgacatcacc caggccgtgg cctgcgccaa gcgcgtcgtg     300 cgcgacccc agggcatcaa ggcgtgggtg gcgtggcgca acaagtgcca gaaccgcgac     360
ctgcgcagct acgtgcaggg ctgccgcgtg ggatccgact acaaggacga cgacgacaag     420
gacgagctc                                                             429
```

<210> SEQ ID NO 5
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Lys Lys Phe Gln Arg Cys Glu Leu Ala Arg Thr Leu Lys Lys Leu Gly
  1               5                  10                  15

Leu Asp Gly Tyr Arg Gly Val Ser Leu Ala Asn Trp Val Cys Leu Ala
             20                  25                  30

Arg Trp Glu Ser Asn Tyr Asn Thr Arg Ala Thr Asn Tyr Asn Arg Gly
         35                  40                  45

Asp Lys Ser Thr Asp Tyr Gly Ile Phe Gln Ile Asn Ser Arg Trp Trp
     50                  55                  60

Cys Asn Asp Gly Lys Thr Pro Lys Ala Val Asn Ala Cys Arg Ile Pro
 65                  70                  75                  80

Cys Ser Ala Leu Leu Lys Asp Asp Ile Thr Gln Ala Val Ala Cys Ala
                 85                  90                  95

Lys Arg Val Val Arg Asp Pro Gln Gly Ile Lys Ala Trp Val Ala Trp
            100                 105                 110

Arg Asn Lys Cys Gln Asn Arg Asp Leu Arg Ser Tyr Val Gln Gly Cys
        115                 120                 125

Arg Val Gly Ser Asp Tyr Lys Asp Asp Asp Lys Asp Glu Leu
    130                 135                 140
```

<210> SEQ ID NO 6
<211> LENGTH: 1275
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ttcagcggcg acttctgcga cagcagccag tgcctgcacg gcggcacctg cctgctgaac      60
gaggaccgca ccccccccctt ctactgcctg tgccccgagg gcttcaccgg cctgctgtgc     120
```

-continued

| | |
|---|---|
| aacgagaccg agcacggccc ctgcttcccc aaccccctgcc acaacgacgc cgagtgccag | 180 |
| gtgaccgacg acagccaccg cggcgacgtg ttcatccagt acatctgcaa gtgccccctg | 240 |
| ggctacgtgg gcatccactg cgagaccacc tgcacctcgc ccctgggcat gcagaccggc | 300 |
| gcgatcgccg acagccagat cagcgccagc agcatgcacc tgggcttcat gggcctgcag | 360 |
| cgctgggccc ccgagctggc ccgcctgcac cagaccggca tcgtgaacgc ctggaccagc | 420 |
| ggcaactacg acaagaaccc gtggattcag gtgaacctga tgcgcaagat gtgggtcacc | 480 |
| ggcgtcgtga cccagggcgc cagccgcgcc ggcagcgccg agtacctgaa gaccttcaag | 540 |
| gtggcctaca gcaccgacgg ccgccagttc cagttcatcc aggtggccgg ccgcagcggc | 600 |
| gacaagatct tcatcggcaa cgtgaacaac tccggcctga gatcaacctg gttcgacacc | 660 |
| cccctggaga cccagtacgt gcgcctggtg cccatcatct gccaccgcgg ctgcaccctg | 720 |
| cgcttcgagc tgctgggctg cgagctgaac ggctgcaccg agccgctggg cctgaaggac | 780 |
| aacaccatcc ccaacaagca gatcaccgcc tccagctact acaagacctg gggcctgagc | 840 |
| gccttctcct ggttcccta ctacgcccgc ctggacaacc agggcaagtt caacgcgtgg | 900 |
| accgcccaga ccaacagcgc ctccgagtgg ctgcagatcg acctgggcag ccagaagcgc | 960 |
| gtgaccggca tcatccccca gggcgcgcgc gacttcggcc acatccagta cgtggccgcc | 1020 |
| taccgcgtgg cctacggcga cgacggcgtg acctggaccg agtacaagga ccccggcgcc | 1080 |
| agcgagagca agatcttccc gggcaacatg gacaacaaca gccacaagaa gaacatcttc | 1140 |
| gagacccct tccaggcccg cttcgtgcgc atccagcccg tggcctggca caaccgcatc | 1200 |
| accctgcgcg tggagctgct gggctgcggc ggcggaggat ccgactacaa ggacgacgac | 1260 |
| gacaaggacg agctc | 1275 |

<210> SEQ ID NO 7
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Phe Ser Gly Asp Phe Cys Asp Ser Ser Gln Cys Leu His Gly Gly Thr
1               5                   10                  15

Cys Leu Leu Asn Glu Asp Arg Thr Pro Pro Phe Tyr Cys Leu Cys Pro
                20                  25                  30

Glu Gly Phe Thr Gly Leu Leu Cys Asn Glu Thr Glu His Gly Pro Cys
            35                  40                  45

Phe Pro Asn Pro Cys His Asn Asp Ala Glu Cys Gln Val Thr Asp Asp
        50                  55                  60

Ser His Arg Gly Asp Val Phe Ile Gln Tyr Ile Cys Lys Cys Pro Leu
65                  70                  75                  80

Gly Tyr Val Gly Ile His Cys Glu Thr Thr Cys Thr Ser Pro Leu Gly
                85                  90                  95

Met Gln Thr Gly Ala Ile Ala Asp Ser Gln Ile Ser Ala Ser Ser Met
            100                 105                 110

His Leu Gly Phe Met Gly Leu Gln Arg Trp Ala Pro Glu Leu Ala Arg
        115                 120                 125

Leu His Gln Thr Gly Ile Val Asn Ala Trp Thr Ser Gly Asn Tyr Asp
    130                 135                 140

Lys Asn Pro Trp Ile Gln Val Asn Leu Met Arg Lys Met Trp Val Thr

Gly Val Val Thr Gln Gly Ala Ser Arg Ala Gly Ser Ala Glu Tyr Leu
145                 150                 155                 160

Lys Thr Phe Lys Val Ala Tyr Ser Thr Asp Gly Arg Gln Phe Gln Phe
            165                 170                 175

Ile Gln Val Ala Gly Arg Ser Asp Lys Ile Phe Ile Gly Asn Val
        180                 185                 190

Asn Asn Ser Gly Leu Lys Ile Asn Leu Phe Asp Thr Pro Leu Glu Thr
    195                 200                 205

Gln Tyr Val Arg Leu Val Pro Ile Ile Cys His Arg Gly Cys Thr Leu
210                 215                 220

Arg Phe Glu Leu Leu Gly Cys Glu Leu Asn Gly Cys Thr Glu Pro Leu
225                 230                 235                 240

Gly Leu Lys Asp Asn Thr Ile Pro Asn Lys Gln Ile Thr Ala Ser Ser
        245                 250                 255

Tyr Tyr Lys Thr Trp Gly Leu Ser Ala Phe Ser Trp Phe Pro Tyr Tyr
    260                 265                 270

Ala Arg Leu Asp Asn Gln Gly Lys Phe Asn Ala Trp Thr Ala Gln Thr
        275                 280                 285

Asn Ser Ala Ser Glu Trp Leu Gln Ile Asp Leu Gly Ser Gln Lys Arg
290                 295                 300

Val Thr Gly Ile Ile Thr Gln Gly Ala Arg Asp Phe Gly His Ile Gln
305                 310                 315                 320

Tyr Val Ala Ala Tyr Arg Val Ala Tyr Gly Asp Asp Gly Val Thr Trp
        325                 330                 335

Thr Glu Tyr Lys Asp Pro Gly Ala Ser Glu Ser Lys Ile Phe Pro Gly
    340                 345                 350

Asn Met Asp Asn Asn Ser His Lys Lys Asn Ile Phe Glu Thr Pro Phe
        355                 360                 365

Gln Ala Arg Phe Val Arg Ile Gln Pro Val Ala Trp His Asn Arg Ile
370                 375                 380

Thr Leu Arg Val Glu Leu Leu Gly Cys Gly Gly Gly Ser Asp Tyr
385                 390                 395                 400

Lys Asp Asp Asp Asp Lys Asp Glu Leu
        405                 410                 415

420                 425

<210> SEQ ID NO 8
<211> LENGTH: 834
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8
ctgcccgtga agcccaccag cagcggcagc agcgaggaga agcagctgaa caacaagtac     60
cccgacgccg tggccacctg gctgaagccc gaccccagcc agaagcagac cttcctggcc    120
ccccagaaca gcgtgtcctc cgaggagacc gacgacaaca gcagaacacc ctgcccagc    180 aagagcaacg agagccccga gcagaccgac gacctggacg acgacgacga acagccag    240 gacgtgaaca gcaacgacag cgacgacgcc gagaccaccg acgacccga ccacagcgac    300 gagagccacc actccgacga gtcggacgag gtggacttcc ccaccgacat ccccaccatc    360
gcggtgttca ccccttcat cccgaccgag agcgccaacg acggccgcgg cgacagcgtg    420
gcctacggcc tgaagtcccg cagcaagaag ttccgccgca gcaacgtgca gtcgcccgac    480

```
gccaccgagg aggacttcac ctcccacatc gagtcggagg agatgcacga cgcccccaag      540
aagaccagcc agctgaccga ccactccaag gagaccaaca gctccgagct gagcaaggag      600
ctgaccccca aggccaagga caagaacaag cacagcaacc tgatcgagag ccaggagaac      660
agcaagctgt cccaggagtt ccacagcctg gaggacaagc tggacctgga ccacaagagc      720
gaggaggaca gcacctgaa gatccgcatc agccacgagc tggacagcgc ctccagcgag      780
gtgaacggcg gcggaggatc cgactacaag gacgacgacg acaaggacga gctc            834
```

<210> SEQ ID NO 9
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Leu Pro Val Lys Pro Thr Ser Gly Ser Glu Glu Lys Gln Leu
1               5                   10                  15

Asn Asn Lys Tyr Pro Asp Ala Val Ala Thr Trp Leu Lys Pro Asp Pro
            20                  25                  30

Ser Gln Lys Gln Thr Phe Leu Ala Pro Gln Asn Ser Val Ser Ser Glu
        35                  40                  45

Glu Thr Asp Asp Asn Lys Gln Asn Thr Leu Pro Ser Lys Ser Asn Glu
    50                  55                  60

Ser Pro Glu Gln Thr Asp Asp Leu Asp Asp Asp Asp Asn Ser Gln
65                  70                  75                  80

Asp Val Asn Ser Asn Asp Ser Asp Asp Ala Glu Thr Thr Asp Pro
                85                  90                  95

Asp His Ser Asp Glu Ser His His Ser Asp Glu Ser Asp Glu Val Asp
            100                 105                 110

Phe Pro Thr Asp Ile Pro Thr Ile Ala Val Phe Thr Pro Phe Ile Pro
        115                 120                 125

Thr Glu Ser Ala Asn Asp Gly Arg Gly Asp Ser Val Ala Tyr Gly Leu
    130                 135                 140

Lys Ser Arg Ser Lys Lys Phe Arg Arg Ser Asn Val Gln Ser Pro Asp
145                 150                 155                 160

Ala Thr Glu Glu Asp Phe Thr Ser His Ile Glu Ser Glu Glu Met His
                165                 170                 175

Asp Ala Pro Lys Lys Thr Ser Gln Leu Thr Asp His Ser Lys Glu Thr
            180                 185                 190

Asn Ser Ser Glu Leu Ser Lys Glu Leu Thr Pro Lys Ala Lys Asp Lys
        195                 200                 205

Asn Lys His Ser Asn Leu Ile Glu Ser Gln Glu Asn Ser Lys Leu Ser
    210                 215                 220

Gln Glu Phe His Ser Leu Glu Asp Lys Leu Asp Leu Asp His Lys Ser
225                 230                 235                 240

Glu Glu Asp Lys His Leu Lys Ile Arg Ile Ser His Glu Leu Asp Ser
                245                 250                 255

Ala Ser Ser Glu Val Asn Gly Gly Gly Gly Ser Asp Tyr Lys Asp Asp
            260                 265                 270

Asp Asp Lys Asp Glu Leu
        275
```

<210> SEQ ID NO 10
<211> LENGTH: 417
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
gagcagctga ccaagtgcga ggtgttccgc gagctgaagg acctgaaggg ctacggcggc      60
gtgtcgctgc ccgagtgggt gtgcaccacc ttccacacca gcggctacga cacccaggcg     120
atcgtgcaga acaacgacag caccgagtac ggcctgttcc agatcaacaa caagatctgg     180
tgcaaggacg accagaaccc ccacagcagc aacatctgca catcagctg cgacaagttc     240
ctggacgacg acctgaccga cgacattatg tgcgtgaaga gatcctgga caaggtgggc     300
atcaactact ggctggccca aggccctg tgcagcgaga gctggacca gtggctgtgc      360
gagaagctgg cggcggagg atccgactac aaggacgacg acgacaagga cgagctc        417
```

<210> SEQ ID NO 11
<211> LENGTH: 139
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Glu Gln Leu Thr Lys Cys Glu Val Phe Arg Glu Leu Lys Asp Leu Lys
1               5                   10                  15
Gly Tyr Gly Gly Val Ser Leu Pro Glu Trp Val Cys Thr Thr Phe His
            20                  25                  30
Thr Ser Gly Tyr Asp Thr Gln Ala Ile Val Gln Asn Asn Asp Ser Thr
        35                  40                  45
Glu Tyr Gly Leu Phe Gln Ile Asn Asn Lys Ile Trp Cys Lys Asp Asp
    50                  55                  60
Gln Asn Pro His Ser Ser Asn Ile Cys Asn Ile Ser Cys Asp Lys Phe
65                  70                  75                  80
Leu Asp Asp Asp Leu Thr Asp Asp Ile Met Cys Val Lys Lys Ile Leu
                85                  90                  95
Asp Lys Val Gly Ile Asn Tyr Trp Leu Ala His Lys Ala Leu Cys Ser
            100                 105                 110
Glu Lys Leu Asp Gln Trp Leu Cys Glu Lys Leu Gly Gly Gly Gly Ser
        115                 120                 125
Asp Tyr Lys Asp Asp Asp Asp Lys Asp Glu Leu
    130                 135
```

<210> SEQ ID NO 12
<211> LENGTH: 426
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
caggccctga gctaccgcga ggccgtgctg cgcgccgtgg accagctgaa cgagcagagc      60
agcgagccca acatctaccg cctgctggag ctggaccagc cccccagga cgacgaggac     120
cccgacagcc ccaagcgcgt gtccttccgc gtgaaggaga ccgtgtgcag ccgcaccacc     180
```
cagcagcccc cgagcagtg cgacttcaag gagaacggcc tgctgaagcg ctgcgagggc    240
accgtgaccc tggaccaggt gcgcggcaac ttcgacatca cctgcaacaa ccaccagagc    300
atccgcatca ccaagcagcc gtgggccccc ccgcaggccg cccgcctgtg ccgcatcgtc    360
gtgatccgcg tgtgccgcgg cggcggagga tccgactaca aggacgacga cgacaaggac    420
gagctc                                                               426

<210> SEQ ID NO 13
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Ala Leu Ser Tyr Arg Glu Ala Val Leu Arg Ala Val Asp Gln Leu
1               5                   10                  15

Asn Glu Gln Ser Ser Glu Pro Asn Ile Tyr Arg Leu Leu Glu Leu Asp
            20                  25                  30

Gln Pro Pro Gln Asp Asp Glu Asp Pro Asp Ser Pro Lys Arg Val Ser
        35                  40                  45

Phe Arg Val Lys Glu Thr Val Cys Ser Arg Thr Thr Gln Gln Pro Pro
    50                  55                  60

Glu Gln Cys Asp Phe Lys Glu Asn Gly Leu Leu Lys Arg Cys Glu Gly
65                  70                  75                  80

Thr Val Thr Leu Asp Gln Val Arg Gly Asn Phe Asp Ile Thr Cys Asn
                85                  90                  95

Asn His Gln Ser Ile Arg Ile Thr Lys Gln Pro Trp Ala Pro Pro Gln
            100                 105                 110

Ala Ala Arg Leu Cys Arg Ile Val Val Ile Arg Val Cys Arg Gly Gly
        115                 120                 125

Gly Gly Ser Asp Tyr Lys Asp Asp Asp Lys Asp Glu Leu
    130                 135                 140

<210> SEQ ID NO 14
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gtgcgcaaca gccagagctg ccgccgcaac aagggcatct gcgtgcccat ccgctgcccc     60
ggcagcatgc gccagatcgg cacctgcctg ggcgcccagg tgaagtgctg ccgccgcaag    120
ggcggcggag gatccgacta caaggacgac gacgacaagg acgagctc                 168

<210> SEQ ID NO 15
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Val Arg Asn Ser Gln Ser Cys Arg Arg Asn Lys Gly Ile Cys Val Pro
1               5                   10                  15

Ile Arg Cys Pro Gly Ser Met Arg Gln Ile Gly Thr Cys Leu Gly Ala
            20                  25                  30

Gln Val Lys Cys Cys Arg Arg Lys Gly Gly Gly Ser Asp Tyr Lys
        35                  40                  45

Asp Asp Asp Asp Lys Asp Glu Leu
        50                  55

<210> SEQ ID NO 16
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

| | |
|---|---|
| gacaccaccg agccctgcga gctggacgac gacgacttcc gctgcgtgtg caacttcacc | 60 |
| gaccccaagc ccgactggtc cagcgccgtg cagtgcatgg tggccgtgga ggtggagatc | 120 |
| agcgccggcg gccgcagcct ggagcagttc ctgaagggcg cggacaccaa cccgaagcag | 180 |
| tacgccgaca ccatcaaggc gctgcgcgtg cgccgcctga gctgggcgc ggcccaggtg | 240 |
| cccgcgcagc tgctggtggc ggtgctgcgc gccctgggct actcgcgcct gaaggagctg | 300 |
| accctggagg acctggaggt gaccggcccc acccccccga ccccctgga ggccgcgggc | 360 |
| cccgccctga ccaccctgag cctgcgcaac gtgtcctgga ccaccggcgg cgcctggctg | 420 |
| ggcgagctgc agcagtggct gaagcccggc ctgcgcgtgc tgaacatcgc ccaggcccac | 480 |
| agcctggcct tcccgtgcgc gggcctgagc accttcgagg cgctgaccac cctggacctg | 540 |
| agcgacaacc cctcgctggg cgacagcggc ctgatggccg ccctgtgccc caacaagttc | 600 |
| cccgcgctga gtacctggc gctgcgcaac gccggcatgg agaccccag cggcgtgtgc | 660 |
| gccgcgctgg ccgccgcccg cgtgcagccc cagtcgctgg acctgtccca caactccctg | 720 |
| cgcgtgaccg cgcccggcgc cacccgctgc gtgtggccca cgccctgcg cagcctgaac | 780 |
| ctgagcttcg ccggcctgga gcaggtgccc aagggcctgc cccccaagct gagcgtgctg | 840 |
| gacctgagct gcaacaagct gagccgcgag ccgcgccgcg acgagctgcc cgaggtgaac | 900 |
| gacctgaccc tggacggcaa ccccttcctg gacccgggcg ccctgcagca ccagaacgac | 960 |
| cccatgatct ccggcgtggt gccgcctgc gcccgctcgg ccctgaccat gggcgtgtcg | 1020 |
| ggcgcgctgg ccctgctgca gggcgcgcgc ggcttcgccg gcggcggagg atccgactac | 1080 |
| aaggacgacg acgacaagga cgagctc | 1107 |

<210> SEQ ID NO 17
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Thr Thr Glu Pro Cys Glu Leu Asp Asp Asp Asp Phe Arg Cys Val
1               5                   10                  15

Cys Asn Phe Thr Asp Pro Lys Pro Asp Trp Ser Ser Ala Val Gln Cys
            20                  25                  30

Met Val Ala Val Glu Val Glu Ile Ser Ala Gly Gly Arg Ser Leu Glu
        35                  40                  45

Gln Phe Leu Lys Gly Ala Asp Thr Asn Pro Lys Gln Tyr Ala Asp Thr

```
                50              55              60
Ile Lys Ala Leu Arg Val Arg Arg Leu Lys Leu Gly Ala Ala Gln Val
 65                  70                  75                  80

Pro Ala Gln Leu Leu Val Ala Val Leu Arg Ala Leu Gly Tyr Ser Arg
                 85                  90                  95

Leu Lys Glu Leu Thr Leu Glu Asp Leu Glu Val Thr Gly Pro Thr Pro
            100                 105                 110

Pro Thr Pro Leu Glu Ala Ala Gly Pro Ala Leu Thr Thr Leu Ser Leu
        115                 120                 125

Arg Asn Val Ser Trp Thr Thr Gly Gly Ala Trp Leu Gly Glu Leu Gln
130                 135                 140

Gln Trp Leu Lys Pro Gly Leu Arg Val Leu Asn Ile Ala Gln Ala His
145                 150                 155                 160

Ser Leu Ala Phe Pro Cys Ala Gly Leu Ser Thr Phe Glu Ala Leu Thr
                165                 170                 175

Thr Leu Asp Leu Ser Asp Asn Pro Ser Leu Gly Asp Ser Gly Leu Met
            180                 185                 190

Ala Ala Leu Cys Pro Asn Lys Phe Pro Ala Leu Gln Tyr Leu Ala Leu
        195                 200                 205

Arg Asn Ala Gly Met Glu Thr Pro Ser Gly Val Cys Ala Ala Leu Ala
210                 215                 220

Ala Ala Arg Val Gln Pro Gln Ser Leu Asp Leu Ser His Asn Ser Leu
225                 230                 235                 240

Arg Val Thr Ala Pro Gly Ala Thr Arg Cys Val Trp Pro Ser Ala Leu
                245                 250                 255

Arg Ser Leu Asn Leu Ser Phe Ala Gly Leu Glu Gln Val Pro Lys Gly
            260                 265                 270

Leu Pro Pro Lys Leu Ser Val Leu Asp Leu Ser Cys Asn Lys Leu Ser
        275                 280                 285

Arg Glu Pro Arg Arg Asp Glu Leu Pro Glu Val Asn Asp Leu Thr Leu
290                 295                 300

Asp Gly Asn Pro Phe Leu Asp Pro Gly Ala Leu Gln His Gln Asn Asp
305                 310                 315                 320

Pro Met Ile Ser Gly Val Val Pro Ala Cys Ala Arg Ser Ala Leu Thr
                325                 330                 335

Met Gly Val Ser Gly Ala Leu Ala Leu Leu Gln Gly Ala Arg Gly Phe
            340                 345                 350

Ala Gly Gly Gly Gly Ser Asp Tyr Lys Asp Asp Asp Lys Asp Glu
        355                 360                 365

Leu
```

<210> SEQ ID NO 18
<211> LENGTH: 336
<212> TYPE: DNA
<213> ORGANISM: Unknown
<220> FEATURE:
<223> OTHER INFORMATION: Description of Unknown: Mammary associated
      serum amyloid A3 polynucleotide

<400> SEQUENCE: 18
atgtggggca ccttcctgaa ggaggcgggc cagggcgcga aggacatgtg gcgcgcctac      60
caggacatga aggaggccaa ctaccgcggc gcggacaagt acttccacgc ccgcggcaac     120
tacgacgcgg cccgccgcgg ccccggcggc cgtgggcgg cgaaggtgat cagcaacgcg     180
cgcgagacca tccagggcat caccgacccc ctgttcaagg gcatgacccg cgaccaggtg     240

```
cgcgaggaca gcaaggccga ccagttcgcg aacgagtggg gccgcagcgg caaggacccc    300
aaccacttcc gccccgcggg cctgcccgac aagtac                              336
```

<210> SEQ ID NO 19
<211> LENGTH: 112
<212> TYPE: PRT
<213> ORGANISM: Unknown
<220> FEATURE:
<223> OTHER INFORMATION: Description of Unknown: Mammary associated
      serum amyloid A3 polypeptide

<400> SEQUENCE: 19

```
Met Trp Gly Thr Phe Leu Lys Glu Ala Gly Gln Gly Ala Lys Asp Met
1               5                   10                  15

Trp Arg Ala Tyr Gln Asp Met Lys Glu Ala Asn Tyr Arg Gly Ala Asp
                20                  25                  30

Lys Tyr Phe His Ala Arg Gly Asn Tyr Asp Ala Ala Arg Arg Gly Pro
            35                  40                  45

Gly Gly Ala Trp Ala Ala Lys Val Ile Ser Asn Ala Arg Glu Thr Ile
        50                  55                  60

Gln Gly Ile Thr Asp Pro Leu Phe Lys Gly Met Thr Arg Asp Gln Val
65                  70                  75                  80

Arg Glu Asp Ser Lys Ala Asp Gln Phe Ala Asn Glu Trp Gly Arg Ser
                85                  90                  95

Gly Lys Asp Pro Asn His Phe Arg Pro Ala Gly Leu Pro Asp Lys Tyr
                100                 105                 110
```

<210> SEQ ID NO 20
<211> LENGTH: 789
<212> TYPE: DNA
<213> ORGANISM: Unknown
<220> FEATURE:
<223> OTHER INFORMATION: Description of Unknown: Osteopontin
      polynucleotide

<400> SEQUENCE: 20

```
agtttacctg taaaaccaac atcatcaggt tcatcagaag aaaaacaatt aaataataaa     60
tatccagatg ctgttgcaat ttggttaaaa cctgatccat cacaaaaaca acatttttta   120
acaccacaaa attcagtatc atcagaagaa acagatgata taaacaaaa tacattacca    180 tcaaaatcaa atgaatcacc agaacaaact gatgatttag atgatgatga tgataattca   240
caagatgtta attcaaatga ttcagatgat gctgaaacaa cagatgatcc tgatcattca   300
gatgaatcac atcactcaga tgaatcagat gaagttgatt ttcctacaga tattccaact   360
attgctgttt ttacaccatt tattcctaca gaatcagcta atgatggtcg tggtgattca   420
gtagcttatg gtttaaaatc acgttcaaaa aaatttcgtc gttcaaatgt acaatcacca   480
gatgctactg aagaagattt cacatcacac attgaatcag aagaaatgca cgatgctcca   540
aaaaaaactt cacaattaac agatcattca aaagaaacta ttcatcaga attatcaaaa    600 gaattaacac aaaagctaa agataaaaat aaacattcaa atttaattga atcacaagaa    660
aattcaaaat tatcacaaga atttcattca ttagaagata attagatttt agatcacaaa   720
tcagaagaag ataaacattt aaaaattcgt atttcacatg aattagattc agcttcatca   780
gaagttaat                                                            789
```

<210> SEQ ID NO 21
<211> LENGTH: 786

<212> TYPE: DNA
<213> ORGANISM: Unknown
<220> FEATURE:
<223> OTHER INFORMATION: Description of Unknown: Osteopontin
      polynucleotide

<400> SEQUENCE: 21

```
ctgcccgtga agcccaccag cagcggcagc agcgaggaga agcagctgaa caacaagtac      60
cccgacgccg tggccacctg gctgaagccc gaccccagcc agaagcagac cttcctggcc     120
ccccagaaca gcgtgtcctc cgaggagacc gacgacaaca gcagaacac cctgcccagc      180
aagagcaacg agagccccga gcagaccgac gacctggacg acgacgacga caacagccag     240
gacgtgaaca gcaacgacag cgacgacgcc gagaccaccg acgaccccga ccacagcgac     300
gagagccacc actccgacga gtcggacgag gtggacttcc ccaccgacat ccccaccatc     360
gcggtgttca ccccttcat cccgaccgag agcgccaacg acggccgcgg cgacagcgtg      420
gcctacggcc tgaagtcccg cagcaagaag ttccgccgca gcaacgtgca gtcgcccgac     480
gccaccgagg aggacttcac ctcccacatc gagtcggagg agatgcacga cgcccccaag     540
aagaccagcc agctgaccga ccactccaag gagaccaaca gctccgagct gagcaaggag     600
ctgacccca aggccaagga caagaacaag cacagcaacc tgatcgagag ccaggagaac      660
agcaagctgt cccaggagtt ccacagcctg gaggacaagc tggacctgga ccacaagagc     720
gaggaggaca gcaccctgaa gatccgcatc agccacgagc tggacagcgc ctccagcgag     780
gtgaac                                                                 786
```

<210> SEQ ID NO 22
<211> LENGTH: 263
<212> TYPE: PRT
<213> ORGANISM: Unknown
<220> FEATURE:
<223> OTHER INFORMATION: Description of Unknown: Osteopontin
      polypeptide
<220> FEATURE:
<221> NAME/KEY: MOD_RES
<222> LOCATION: (1)..(1)
<223> OTHER INFORMATION: May or may not be present

<400> SEQUENCE: 22

```
Met Leu Pro Val Lys Pro Thr Ser Ser Gly Ser Ser Glu Glu Lys Gln
1               5                   10                  15

Leu Asn Asn Lys Tyr Pro Asp Ala Val Ala Ile Trp Leu Lys Pro Asp
            20                  25                  30

Pro Ser Gln Lys Gln Thr Phe Leu Thr Pro Gln Asn Ser Val Ser Ser
        35                  40                  45

Glu Glu Thr Asp Asp Asn Lys Gln Asn Thr Leu Pro Ser Lys Ser Asn
    50                  55                  60

Glu Ser Pro Glu Gln Thr Asp Asp Leu Asp Asp Asp Asp Asn Ser
65                  70                  75                  80

Gln Asp Val Asn Ser Asn Asp Ser Asp Asp Ala Glu Thr Thr Asp Asp
                85                  90                  95

Pro Asp His Ser Asp Glu Ser His His Ser Asp Glu Ser Asp Glu Val
            100                 105                 110

Asp Phe Pro Thr Asp Ile Pro Thr Ile Ala Val Phe Thr Pro Phe Ile
        115                 120                 125

Pro Thr Glu Ser Ala Asn Asp Gly Arg Gly Asp Ser Val Ala Tyr Gly
    130                 135                 140

Leu Lys Ser Arg Ser Lys Lys Phe Arg Arg Ser Asn Val Gln Ser Pro
```

```
                145                 150                 155                 160
Asp Ala Thr Glu Glu Asp Phe Thr Ser His Ile Glu Ser Glu Met
                165                 170                 175

His Asp Ala Pro Lys Lys Thr Ser Gln Leu Thr Asp His Ser Lys Glu
            180                 185                 190

Thr Asn Ser Ser Glu Leu Ser Lys Glu Leu Thr Pro Lys Ala Lys Asp
        195                 200                 205

Lys Asn Lys His Ser Asn Leu Ile Glu Ser Gln Glu Asn Ser Lys Leu
    210                 215                 220

Ser Gln Glu Phe His Ser Leu Glu Asp Lys Leu Asp Leu Asp His Lys
225                 230                 235                 240

Ser Glu Glu Asp Lys His Leu Lys Ile Arg Ile Ser His Glu Leu Asp
                245                 250                 255

Ser Ala Ser Ser Glu Val Asn
            260

<210> SEQ ID NO 23
<211> LENGTH: 1227
<212> TYPE: DNA
<213> ORGANISM: Unknown
<220> FEATURE:
<223> OTHER INFORMATION: Description of Unknown: Lactadherin
      polynucleotide

<400> SEQUENCE: 23
ttcagcggcg acttctgcga cagcagccag tgcctgcacg gcggcacctg cctgctgaac      60
gaggaccgca ccccccccctt ctactgcctg tgccccgagg gcttcaccgg cctgctgtgc    120
aacgagaccg agcacggccc ctgcttcccc aacccctgcc acaacgacgc cgagtgccag    180
gtgaccgacg acagccaccg cggcgacgtg ttcatccagt acatctgcaa gtgccccctg    240
ggctacgtgg gcatccactg cgagaccacc tgcacctcgc ccctgggcat gcagaccggc    300
gcgatcgccg acagccagat cagcgccagc agcatgcacc tgggcttcat gggcctgcag    360
cgctgggccc ccgagctggc ccgcctgcac cagaccggca tcgtgaacgc ctggaccagc    420
ggcaactacg acaagaaccc gtggattcag gtgaacctga tgcgcaagat gtgggtcacc    480
ggcgtcgtga cccagggcgc cagccgcgcc ggcagcgccg agtacctgaa gaccttcaag    540
gtggcctaca gcaccgacgg ccgccagttc cagttcatcc aggtggccgg ccgcagcggc    600
gacaagatct tcatcggcaa cgtgaacaac tccggcctga gatcaacct gttcgacacc     660
cccctggaga cccagtacgt gcgcctggtg cccatcatct gccaccgcgg ctgcaccctg    720
cgcttcgagc tgctgggctg cgagctgaac ggctgcaccg agccgctggg cctgaaggac    780
aacaccatcc ccaacaagca gatcaccgcc tccagctact acaagacctg gggcctgagc    840
gccttctcct ggttccccta ctacgcccgc ctggacaacc agggcaagtt caacgcgtgg    900
accgcccaga ccaacagcgc ctccgagtgg ctgcagatcg acctgggcag ccagaagcgc    960
gtgaccggca tcatcaccca gggcgcgcgc gacttcggcc acatccagta cgtggccgcc   1020
taccgcgtgg cctacggcga cgacggcgtg acctggaccg agtacaagga ccccggcgcc   1080
agcgagagca agatcttccc gggcaacatg gacaacaaca gccacaagaa gaacatcttc    1140
gagacccccct tccaggcccg cttcgtgcgc atccagcccg tggcctggca caaccgcatc   1200
accctgcgcg tggagctgct gggctgc                                        1227

<210> SEQ ID NO 24
<211> LENGTH: 409
```

<212> TYPE: PRT
<213> ORGANISM: Unknown
<220> FEATURE:
<223> OTHER INFORMATION: Description of Unknown: Lactadherin polypeptide

<400> SEQUENCE: 24

```
Phe Ser Gly Asp Phe Cys Asp Ser Ser Gln Cys Leu His Gly Gly Thr
1               5                   10                  15
Cys Leu Leu Asn Glu Asp Arg Thr Pro Pro Phe Tyr Cys Leu Cys Pro
                20                  25                  30
Glu Gly Phe Thr Gly Leu Leu Cys Asn Glu Thr Glu His Gly Pro Cys
            35                  40                  45
Phe Pro Asn Pro Cys His Asn Asp Ala Glu Cys Gln Val Thr Asp Asp
    50                  55                  60
Ser His Arg Gly Asp Val Phe Ile Gln Tyr Ile Cys Lys Cys Pro Leu
65                  70                  75                  80
Gly Tyr Val Gly Ile His Cys Glu Thr Thr Cys Thr Ser Pro Leu Gly
                85                  90                  95
Met Gln Thr Gly Ala Ile Ala Asp Ser Gln Ile Ser Ala Ser Ser Met
                100                 105                 110
His Leu Gly Phe Met Gly Leu Gln Arg Trp Ala Pro Glu Leu Ala Arg
            115                 120                 125
Leu His Gln Thr Gly Ile Val Asn Ala Trp Thr Ser Gly Asn Tyr Asp
    130                 135                 140
Lys Asn Pro Trp Ile Gln Val Asn Leu Met Arg Lys Met Trp Val Thr
145                 150                 155                 160
Gly Val Val Thr Gln Gly Ala Ser Arg Ala Gly Ser Ala Glu Tyr Leu
                165                 170                 175
Lys Thr Phe Lys Val Ala Tyr Ser Thr Asp Gly Arg Gln Phe Gln Phe
            180                 185                 190
Ile Gln Val Ala Gly Arg Ser Gly Asp Lys Ile Phe Ile Gly Asn Val
    195                 200                 205
Asn Asn Ser Gly Leu Lys Ile Asn Leu Phe Asp Thr Pro Leu Glu Thr
210                 215                 220
Gln Tyr Val Arg Leu Val Pro Ile Ile Cys His Arg Gly Cys Thr Leu
225                 230                 235                 240
Arg Phe Glu Leu Leu Gly Cys Glu Leu Asn Gly Cys Thr Glu Pro Leu
                245                 250                 255
Gly Leu Lys Asp Asn Thr Ile Pro Asn Lys Gln Ile Thr Ala Ser Ser
            260                 265                 270
Tyr Tyr Lys Thr Trp Gly Leu Ser Ala Phe Ser Trp Phe Pro Tyr Tyr
    275                 280                 285
Ala Arg Leu Asp Asn Gln Gly Lys Phe Asn Ala Trp Thr Ala Gln Thr
    290                 295                 300
Asn Ser Ala Ser Glu Trp Leu Gln Ile Asp Leu Gly Ser Gln Lys Arg
305                 310                 315                 320
Val Thr Gly Ile Ile Thr Gln Gly Ala Arg Asp Phe Gly His Ile Gln
                325                 330                 335
Tyr Val Ala Ala Tyr Arg Val Ala Tyr Gly Asp Asp Gly Val Thr Trp
            340                 345                 350
Thr Glu Tyr Lys Asp Pro Gly Ala Ser Glu Ser Lys Ile Phe Pro Gly
    355                 360                 365
Asn Met Asp Asn Asn Ser His Lys Lys Asn Ile Phe Glu Thr Pro Phe
    370                 375                 380
```

```
Gln Ala Arg Phe Val Arg Ile Gln Pro Val Ala Trp His Asn Arg Ile
385                 390                 395                 400

Thr Leu Arg Val Glu Leu Leu Gly Cys
            405

<210> SEQ ID NO 25
<211> LENGTH: 378
<212> TYPE: DNA
<213> ORGANISM: Unknown
<220> FEATURE:
<223> OTHER INFORMATION: Description of Unknown: Cathelicidin-1
      polynucleotide

<400> SEQUENCE: 25
caggccctga gctaccgcga ggccgtgctg cgcgccgtgg accagctgaa cgagcagagc    60
agcgagccca acatctaccg cctgctggag ctggaccagc cccccagga cgacgaggac   120 cccgacagcc ccaagcgcgt gtccttccgc gtgaaggaga ccgtgtgcag ccgcaccacc   180
cagcagcccc ccgagcagtg cgacttcaag gagaacggcc tgctgaagcg ctgcgagggc   240
accgtgaccc tggaccaggt gcgcggcaac ttcgacatca cctgcaacaa ccaccagagc   300
atccgcatca ccaagcagcc gtgggccccc ccgcaggccg cccgcctgtg ccgcatcgtc   360
gtgatccgcg tgtgccgc                                                 378

<210> SEQ ID NO 26
<211> LENGTH: 126
<212> TYPE: PRT
<213> ORGANISM: Unknown
<220> FEATURE:
<223> OTHER INFORMATION: Description of Unknown: Cathelicidin-1
      polypeptide

<400> SEQUENCE: 26

Gln Ala Leu Ser Tyr Arg Glu Ala Val Leu Arg Ala Val Asp Gln Leu
1               5                   10                  15

Asn Glu Gln Ser Ser Glu Pro Asn Ile Tyr Arg Leu Leu Glu Leu Asp
            20                  25                  30

Gln Pro Pro Gln Asp Asp Glu Asp Pro Asp Ser Pro Lys Arg Val Ser
        35                  40                  45

Phe Arg Val Lys Glu Thr Val Cys Ser Arg Thr Thr Gln Gln Pro Pro
    50                  55                  60

Glu Gln Cys Asp Phe Lys Glu Asn Gly Leu Leu Lys Arg Cys Glu Gly
65                  70                  75                  80

Thr Val Thr Leu Asp Gln Val Arg Gly Asn Phe Asp Ile Thr Cys Asn
                85                  90                  95

Asn His Gln Ser Ile Arg Ile Thr Lys Gln Pro Trp Ala Pro Pro Gln
            100                 105                 110

Ala Ala Arg Leu Cys Arg Ile Val Val Ile Arg Val Cys Arg
        115                 120                 125

<210> SEQ ID NO 27
<211> LENGTH: 390
<212> TYPE: DNA
<213> ORGANISM: Unknown
<220> FEATURE:
<223> OTHER INFORMATION: Description of Unknown: Bovine milk lysozyme
      polynucleotide

<400> SEQUENCE: 27
aagaagttcc agcgctgcga gctggcccgc accctgaaga agctgggcct ggacggctac    60
```

```
cgcggcgtgt ccctggccaa ctgggtgtgc ctggcccgct gggagagcaa ctacaacacc      120
cgcgccacca actacaaccg cggcgacaag agcaccgact acggcatctt ccagatcaac      180
agccgctggt ggtgcaacga cggcaagacc cccaaggccg tgaacgcctg ccgcatcccc      240
tgcagcgccc tgctgaagga cgacatcacc caggccgtgg cctgcgccaa gcgcgtcgtg      300 cgcgacccc agggcatcaa ggcgtgggtg gcgtggcgca acaagtgcca gaaccgcgac       360
ctgcgcagct acgtgcaggg ctgccgcgtg                                      390
```

<210> SEQ ID NO 28
<211> LENGTH: 130
<212> TYPE: PRT
<213> ORGANISM: Unknown
<220> FEATURE:
<223> OTHER INFORMATION: Description of Unknown: Bovine milk lysozyme polypeptide

<400> SEQUENCE: 28

```
Lys Lys Phe Gln Arg Cys Glu Leu Ala Arg Thr Leu Lys Lys Leu Gly
 1               5                  10                  15

Leu Asp Gly Tyr Arg Gly Val Ser Leu Ala Asn Trp Val Cys Leu Ala
            20                  25                  30

Arg Trp Glu Ser Asn Tyr Asn Thr Arg Ala Thr Asn Tyr Asn Arg Gly
        35                  40                  45

Asp Lys Ser Thr Asp Tyr Gly Ile Phe Gln Ile Asn Ser Arg Trp Trp
    50                  55                  60

Cys Asn Asp Gly Lys Thr Pro Lys Ala Val Asn Ala Cys Arg Ile Pro
65                  70                  75                  80

Cys Ser Ala Leu Leu Lys Asp Asp Ile Thr Gln Ala Val Ala Cys Ala
                85                  90                  95

Lys Arg Val Val Arg Asp Pro Gln Gly Ile Lys Ala Trp Val Ala Trp
            100                 105                 110

Arg Asn Lys Cys Gln Asn Arg Asp Leu Arg Ser Tyr Val Gln Gly Cys
        115                 120                 125

Arg Val
    130
```

<210> SEQ ID NO 29
<211> LENGTH: 369
<212> TYPE: DNA
<213> ORGANISM: Unknown
<220> FEATURE:
<223> OTHER INFORMATION: Description of Unknown: Alpha-lactalbumin polynucleotide

<400> SEQUENCE: 29

```
gagcagctga ccaagtgcga ggtgttccgc gagctgaagg acctgaaggg ctacggcggc      60
gtgtcgctgc ccgagtgggt gtgcaccacc ttccacacca gcggctacga cacccaggcg     120
atcgtgcaga acaacgacag caccgagtac ggcctgttcc agatcaacaa caagatctgg     180
tgcaaggacg accagaaccc ccacagcagc aacatctgca acatcagctg cgacaagttc     240
ctggacgacg acctgaccga cgacattatg tgcgtgaaga agatcctgga caaggtgggc     300
atcaactact ggctggccca caaggccctg tgcagcgaga gctggaccca gtggctgtgc     360
gagaagctg                                                             369
```

<210> SEQ ID NO 30
<211> LENGTH: 123

<212> TYPE: PRT
<213> ORGANISM: Unknown
<220> FEATURE:
<223> OTHER INFORMATION: Description of Unknown: Alpha-lactalbumin
      polypeptide

<400> SEQUENCE: 30

Glu Gln Leu Thr Lys Cys Glu Val Phe Arg Glu Leu Lys Asp Leu Lys
1               5                   10                  15

Gly Tyr Gly Gly Val Ser Leu Pro Glu Trp Val Cys Thr Thr Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
    50                  55                  60

Gln Asn Pro His Ser Ser Asn Ile Cys Asn Ile Ser Cys Asp Lys Phe
65                  70                  75                  80

Leu Asp Asp Asp Leu Thr Asp Asp Ile Met Cys Val Lys Lys Ile Leu
                85                  90                  95

Asp Lys Val Gly Ile Asn Tyr Trp Leu Ala His Lys Ala Leu Cys Ser
            100                 105                 110

Glu Lys Leu Asp Gln Trp Leu Cys Glu Lys Leu
            115                 120

<210> SEQ ID NO 31
<211> LENGTH: 120
<212> TYPE: DNA
<213> ORGANISM: Unknown
<220> FEATURE:
<223> OTHER INFORMATION: Description of Unknown: Lingual antimicrobial
      polynucleotide

<400> SEQUENCE: 31
gtgcgcaaca gccagagctg ccgccgcaac aagggcatct gcgtgcccat ccgctgcccc     60
ggcagcatgc gccagatcgg cacctgcctg ggcgcccagg tgaagtgctg ccgccgcaag    120

<210> SEQ ID NO 32
<211> LENGTH: 40
<212> TYPE: PRT
<213> ORGANISM: Unknown
<220> FEATURE:
<223> OTHER INFORMATION: Description of Unknown: Lingual antimicrobial
      polypeptide

<400> SEQUENCE: 32

Val Arg Asn Ser Gln Ser Cys Arg Arg Asn Lys Gly Ile Cys Val Pro
1               5                   10                  15

Ile Arg Cys Pro Gly Ser Met Arg Gln Ile Gly Thr Cys Leu Gly Ala
            20                  25                  30

Gln Val Lys Cys Cys Arg Arg Lys
        35                  40

<210> SEQ ID NO 33
<211> LENGTH: 1059
<212> TYPE: DNA
<213> ORGANISM: Unknown
<220> FEATURE:
<223> OTHER INFORMATION: Description of Unknown: Soluble CD14
      polynucleotide

<400> SEQUENCE: 33
gacaccaccg agccctgcga gctggacgac gacgacttcc gctgcgtgtg caacttcacc     60

```
gaccccaagc cgactggtc cagcgccgtg cagtgcatgg tggccgtgga ggtggagatc    120
agcgccggcg gccgcagcct ggagcagttc ctgaagggcg cggacaccaa cccgaagcag    180
tacgccgaca ccatcaaggc gctgcgcgtg cgccgcctga agctgggcgc ggcccaggtg    240
cccgcgcagc tgctggtggc ggtgctgcgc gccctgggct actcgcgcct gaaggagctg    300
accctggagg acctggaggt gaccggcccc acccccccga ccccctgga ggccgcgggc    360 cccgccctga ccaccctgag cctgcgcaac gtgtcctgga ccaccggcgg cgcctggctg    420
ggcgagctgc agcagtggct gaagcccggc ctgcgcgtgc tgaacatcgc ccaggcccac    480
agcctggcct tcccgtgcgc gggcctgagc accttcgagg cgctgaccac cctggacctg    540
agcgacaacc cctcgctggg cgacagcggc ctgatggccg ccctgtgccc caacaagttc    600
cccgcgctgc agtacctggc gctgcgcaac gccggcatgg agacccccag cggcgtgtgc    660
gccgcgctgg ccgccgcccg cgtgcagccc cagtcgctgg acctgtccca caactccctg    720
cgcgtgaccg cgcccggcgc caccgcctgc gtgtggccca cgccctgcg cagcctgaac    780 ctgagcttcg ccggcctgga gcaggtgccc aagggcctgc cccccaagct gagcgtgctg    840
gacctgagct gcaacaagct gagccgcgag ccgcgccgcg acgagctgcc cgaggtgaac    900
gacctgaccc tggacggcaa ccccttcctg gacccgggcg ccctgcagca ccagaacgac    960
cccatgatct ccggcgtggt gccgccctgc gcccgctcgg ccctgaccat gggcgtgtcg   1020
ggcgcgctgg ccctgctgca gggcgcgcgc ggcttcgcc                          1059

<210> SEQ ID NO 34
<211> LENGTH: 353
<212> TYPE: PRT
<213> ORGANISM: Unknown
<220> FEATURE:
<223> OTHER INFORMATION: Description of Unknown: Soluble CD14
      polypeptide

<400> SEQUENCE: 34

Asp Thr Thr Glu Pro Cys Glu Leu Asp Asp Asp Phe Arg Cys Val
1               5                   10                  15

Cys Asn Phe Thr Asp Pro Lys Pro Asp Trp Ser Ser Ala Val Gln Cys
            20                  25                  30

Met Val Ala Val Glu Val Glu Ile Ser Ala Gly Gly Arg Ser Leu Glu
        35                  40                  45

Gln Phe Leu Lys Gly Ala Asp Thr Asn Pro Lys Gln Tyr Ala Asp Thr
    50                  55                  60

Ile Lys Ala Leu Arg Val Arg Arg Leu Lys Leu Gly Ala Ala Gln Val
65                  70                  75                  80

Pro Ala Gln Leu Leu Val Ala Val Leu Arg Ala Leu Gly Tyr Ser Arg
                85                  90                  95

Leu Lys Glu Leu Thr Leu Glu Asp Leu Glu Val Thr Gly Pro Thr Pro
            100                 105                 110

Pro Thr Pro Leu Glu Ala Ala Gly Pro Ala Leu Thr Thr Leu Ser Leu
        115                 120                 125

Arg Asn Val Ser Trp Thr Thr Gly Gly Ala Trp Leu Gly Glu Leu Gln
    130                 135                 140

Gln Trp Leu Lys Pro Gly Leu Arg Val Leu Asn Ile Ala Gln Ala His
145                 150                 155                 160

Ser Leu Ala Phe Pro Cys Ala Gly Leu Ser Thr Phe Glu Ala Leu Thr
                165                 170                 175
```

```
Thr Leu Asp Leu Ser Asp Asn Pro Ser Leu Gly Asp Ser Gly Leu Met
            180                 185                 190

Ala Ala Leu Cys Pro Asn Lys Phe Pro Ala Leu Gln Tyr Leu Ala Leu
        195                 200                 205

Arg Asn Ala Gly Met Glu Thr Pro Ser Gly Val Cys Ala Ala Leu Ala
    210                 215                 220

Ala Ala Arg Val Gln Pro Gln Ser Leu Asp Leu Ser His Asn Ser Leu
225                 230                 235                 240

Arg Val Thr Ala Pro Gly Ala Thr Arg Cys Val Trp Pro Ser Ala Leu
                245                 250                 255

Arg Ser Leu Asn Leu Ser Phe Ala Gly Leu Glu Gln Val Pro Lys Gly
            260                 265                 270

Leu Pro Pro Lys Leu Ser Val Leu Asp Leu Ser Cys Asn Lys Leu Ser
        275                 280                 285

Arg Glu Pro Arg Arg Asp Glu Leu Pro Glu Val Asn Asp Leu Thr Leu
    290                 295                 300

Asp Gly Asn Pro Phe Leu Asp Pro Gly Ala Leu Gln His Gln Asn Asp
305                 310                 315                 320

Pro Met Ile Ser Gly Val Val Pro Ala Cys Ala Arg Ser Ala Leu Thr
                325                 330                 335

Met Gly Val Ser Gly Ala Leu Ala Leu Leu Gln Gly Ala Arg Gly Phe
            340                 345                 350

Ala

<210> SEQ ID NO 35
<211> LENGTH: 112
<212> TYPE: PRT
<213> ORGANISM: Unknown
<220> FEATURE:
<223> OTHER INFORMATION: Description of Unknown: Illustrative protein
      accumulation gamma zein polypeptide

<400> SEQUENCE: 35

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

<210> SEQ ID NO 36
<211> LENGTH: 77
<212> TYPE: PRT
<213> ORGANISM: Unknown
<220> FEATURE:
<223> OTHER INFORMATION: Description of Unknown: Illustrative protein
      accumulation hydrophobin polypeptide

<400> SEQUENCE: 36

Gly Ser Ser Asn Gly Asn Gly Asn Val Cys Pro Pro Gly Leu Phe Ser
```

```
                1               5                      10                     15
            Asn Pro Gln Cys Cys Ala Thr Gln Val Leu Gly Leu Ile Gly Leu Asp
                            20                    25                    30
            Cys Lys Val Pro Ser Gln Asn Val Tyr Asp Gly Thr Asp Phe Arg Asn
                        35                    40                    45
            Val Cys Ala Lys Thr Gly Ala Gln Pro Leu Cys Cys Val Ala Pro Val
                50                    55                    60
            Ala Gly Gln Ala Leu Leu Cys Gln Thr Ala Val Gly Ala
            65                    70                    75

<210> SEQ ID NO 37
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacaccaccc tgaccaacgt gaccgacccc agcctggacc tgaccgccct gagctgggag      60
gtgggctgcg cgcccccgt gcccctggtc aagtgcgacg agaacagccc ctaccgcacc     120
atcaccggcg actgcaacaa ccgccgctcc cccgccctgg gcgccgccaa ccgcgccctg     180
gcccgctggc tgcccgccga gtacgaggac ggcctggccc tgcccttcgg ctggacccag     240
cgcaagaccc gcaacggctt ccgcgtgccg ctggcccgcg aggtgtccaa caagatcgtg     300
ggctacctgg acgaggaggg cgtgctggac cagaaccgca gcctgctgtt catgcagtgg     360
ggccagatcg tggaccacga cctggacttc gccccgaga ccgagctggg cagcaacgag     420
cacagcaaga cccagtgcga ggagtactgc atccagggcg acaactgctt ccccatcatg     480
ttccccaaga cgaccccaa gctgaagacc cagggcaagt gcatgccgtt cttccgcgcc     540
ggcttcgtgt gccccacccc cccgtaccag agcctggcgc gcgagcagat caacgccgtg     600
acctcgttcc tggacgccag cctggtgtac ggcagcgagc cctccctggc ctcccgcctg     660
cgcaacctgt ccagccccct gggcctgatg gccgtgaacc aggaggcctg ggaccacggc     720
ctggcctacc tgcccttcaa caacaagaag cccagcccct gcgagttcat caacaccacc     780
gcccgcgtgc cctgcttcct ggcgggcgac ttccgcgcgt cggagcagat cctgctggcc     840
accgcccaca ccctgctgct gcgcgagcac aaccgcctgg cccgcgagct gaagaagctg     900
aacccccact ggaacggcga gaagctgtac caggaggcgc gcaagatcct gggcgccttc     960
atccagatca tcaccttccg cgactacctg ccgatcgtgc tgggctccga gatgcagaag    1020
tggattccgc cctaccaggg ctacaacaac agcgtggacc ccgcatcag caacgtgttc    1080 accttcgcct tccgcttcgg ccacatggag gtgcccagca ccgtgtcccg cctggacgag    1140
aactaccagc cctggggccc cgaggcggag ctgcccctgc acccctgtt cttcaacacc    1200 tggcgcatca tcaaggacgg cggcatcgac cccctggtgc gcggcctgct ggcgaagaag    1260
tccaagctga tgaaccagga caagatggtc accagcgagc tgcgcaacaa gctgttccag    1320
cccacccaca gatccacgg cttcgacctg gccgccatca acctgcagcg ctgccgcgac    1380
cacggcatgc ccggctacaa ctcgtggcgc ggcttctgcg gcctgagcca gcccaagacc    1440
ctgaagggcc tgcagaccgt gctgaagaac aagatcctgg ccaagaagct gatggacctg    1500
tacaagaccc ccgacaacat cgacatctgg atcggcggca acgccgagcc catggtggag    1560
cgcggccgcg tgggcccgct gctggcctgc ctgctgggcc gccagttcca gcagatccgc    1620
```

```
gacggcgacc gcttctggtg ggagaacccc ggcgtgttca ccgagaagca gcgcgacagc    1680
ctgcagaagg tgtccttcag ccgcctgatc tgcgacaaca cccacatcac caaggtgccg    1740
ctgcacgcct tccaggccaa caactacccc cacgacttcg tggactgctc caccgtggac    1800
aagctggacc tgtccccgtg ggccagccgc gagaacggat ccgactacaa ggacgacgac    1860
gacaaggacg agctc                                                      1875

<210> SEQ ID NO 38
<211> LENGTH: 625
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Thr Thr Leu Thr Asn Val Thr Asp Pro Ser Leu Asp Leu Thr Ala
1               5                   10                  15

Leu Ser Trp Glu Val Gly Cys Gly Ala Pro Val Pro Leu Val Lys Cys
            20                  25                  30

Asp Glu Asn Ser Pro Tyr Arg Thr Ile Thr Gly Asp Cys Asn Asn Arg
        35                  40                  45

Arg Ser Pro Ala Leu Gly Ala Ala Asn Arg Ala Leu Ala Arg Trp Leu
    50                  55                  60

Pro Ala Glu Tyr Glu Asp Gly Leu Ala Leu Pro Phe Gly Trp Thr Gln
65                  70                  75                  80

Arg Lys Thr Arg Asn Gly Phe Arg Val Pro Leu Ala Arg Glu Val Ser
                85                  90                  95

Asn Lys Ile Val Gly Tyr Leu Asp Glu Glu Gly Val Leu Asp Gln Asn
            100                 105                 110

Arg Ser Leu Leu Phe Met Gln Trp Gly Gln Ile Val Asp His Asp Leu
        115                 120                 125

Asp Phe Ala Pro Glu Thr Glu Leu Gly Ser Asn Glu His Ser Lys Thr
    130                 135                 140

Gln Cys Glu Glu Tyr Cys Ile Gln Gly Asp Asn Cys Phe Pro Ile Met
145                 150                 155                 160

Phe Pro Lys Asn Asp Pro Lys Leu Lys Thr Gln Gly Lys Cys Met Pro
                165                 170                 175

Phe Phe Arg Ala Gly Phe Val Cys Pro Thr Pro Tyr Gln Ser Leu
            180                 185                 190

Ala Arg Glu Gln Ile Asn Ala Val Thr Ser Phe Leu Asp Ala Ser Leu
        195                 200                 205

Val Tyr Gly Ser Glu Pro Ser Leu Ala Ser Arg Leu Arg Asn Leu Ser
    210                 215                 220

Ser Pro Leu Gly Leu Met Ala Val Asn Gln Glu Ala Trp Asp His Gly
225                 230                 235                 240

Leu Ala Tyr Leu Pro Phe Asn Asn Lys Lys Pro Ser Pro Cys Glu Phe
                245                 250                 255

Ile Asn Thr Thr Ala Arg Val Pro Cys Phe Leu Ala Gly Asp Phe Arg
            260                 265                 270

Ala Ser Glu Gln Ile Leu Leu Ala Thr Ala His Thr Leu Leu Leu Arg
        275                 280                 285

Glu His Asn Arg Leu Ala Arg Glu Leu Lys Lys Leu Asn Pro His Trp
    290                 295                 300

Asn Gly Glu Lys Leu Tyr Gln Glu Ala Arg Lys Ile Leu Gly Ala Phe
```

```
            305                 310                 315                 320
Ile Gln Ile Ile Thr Phe Arg Asp Tyr Leu Pro Ile Val Leu Gly Ser
                    325                 330                 335

Glu Met Gln Lys Trp Ile Pro Pro Tyr Gln Gly Tyr Asn Asn Ser Val
                    340                 345                 350

Asp Pro Arg Ile Ser Asn Val Phe Thr Phe Ala Phe Arg Phe Gly His
                    355                 360                 365

Met Glu Val Pro Ser Thr Val Ser Arg Leu Asp Glu Asn Tyr Gln Pro
                    370                 375                 380

Trp Gly Pro Glu Ala Glu Leu Pro Leu His Thr Leu Phe Phe Asn Thr
385                 390                 395                 400

Trp Arg Ile Ile Lys Asp Gly Gly Ile Asp Pro Leu Val Arg Gly Leu
                    405                 410                 415

Leu Ala Lys Lys Ser Lys Leu Met Asn Gln Asp Lys Met Val Thr Ser
                    420                 425                 430

Glu Leu Arg Asn Lys Leu Phe Gln Pro Thr His Lys Ile His Gly Phe
                    435                 440                 445

Asp Leu Ala Ala Ile Asn Leu Gln Arg Cys Arg Asp His Gly Met Pro
                    450                 455                 460

Gly Tyr Asn Ser Trp Arg Gly Phe Cys Gly Leu Ser Gln Pro Lys Thr
465                 470                 475                 480

Leu Lys Gly Leu Gln Thr Val Leu Lys Asn Lys Ile Leu Ala Lys Lys
                    485                 490                 495

Leu Met Asp Leu Tyr Lys Thr Pro Asp Asn Ile Asp Ile Trp Ile Gly
                    500                 505                 510

Gly Asn Ala Glu Pro Met Val Glu Arg Gly Arg Val Gly Pro Leu Leu
                    515                 520                 525

Ala Cys Leu Leu Gly Arg Gln Phe Gln Gln Ile Arg Asp Gly Asp Arg
                    530                 535                 540

Phe Trp Trp Glu Asn Pro Gly Val Phe Thr Glu Lys Gln Arg Asp Ser
545                 550                 555                 560

Leu Gln Lys Val Ser Phe Ser Arg Leu Ile Cys Asp Asn Thr His Ile
                    565                 570                 575

Thr Lys Val Pro Leu His Ala Phe Gln Ala Asn Asn Tyr Pro His Asp
                    580                 585                 590

Phe Val Asp Cys Ser Thr Val Asp Lys Leu Asp Leu Ser Pro Trp Ala
                    595                 600                 605

Ser Arg Glu Asn Gly Ser Asp Tyr Lys Asp Asp Asp Lys Asp Glu
                    610                 615                 620

Leu
625

<210> SEQ ID NO 39
<211> LENGTH: 1836
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gacaccaccc tgaccaacgt gaccgacccc agcctggacc tgaccgccct gagctgggag      60
gtgggctgcg cgcccccgt gcccctggtc aagtgcgacg agaacagccc ctaccgcacc      120
atcaccggcg actgcaacaa ccgccgctcc cccgccctgg cgccgccaa cgcgccctg       180
```

```
gcccgctggc tgcccgccga gtacgaggac ggcctggccc tgcccttcgg ctggacccag    240
cgcaagaccc gcaacggctt ccgcgtgccg ctggcccgcg aggtgtccaa caagatcgtg    300
ggctacctgg acgaggaggg cgtgctggac cagaaccgca gcctgctgtt catgcagtgg    360
ggccagatcg tggaccacga cctggacttc gcccccgaga ccgagctggg cagcaacgag    420
cacagcaaga cccagtgcga ggagtactgc atccagggcg acaactgctt ccccatcatg    480
ttccccaaga cgaccccaa gctgaagacc cagggcaagt gcatgccgtt cttccgcgcc     540
ggcttcgtgt gccccacccc cccgtaccag agcctggcgc gcgagcagat caacgccgtg    600
acctcgttcc tggacgccag cctggtgtac ggcagcgagc cctccctggc ctcccgcctg    660
cgcaacctgt ccagcccct gggcctgatg gccgtgaacc aggaggcctg ggaccacggc     720
ctggcctacc tgcccttcaa caacaagaag cccagccct gcgagttcat caacaccacc     780
gcccgcgtgc cctgcttcct ggcgggcgac ttccgcgcgt cggagcagat cctgctggcc    840
accgcccaca ccctgctgct gcgcgagcac aaccgcctgg cccgcgagct gaagaagctg    900 aaccccccact ggaacggcga gaagctgtac caggaggcgc gcaagatcct gggcgccttc   960
atccagatca tcaccttccg cgactacctg ccgatcgtgc tgggctccga gatgcagaag    1020
tggattccgc cctaccaggg ctacaacaac agcgtggacc cccgcatcag caacgtgttc    1080
accttcgcct ccgcttcgg ccacatggag gtgcccagca ccgtgtcccg cctggacgag     1140
aactaccagc cctggggccc cgaggcggag ctgcccctgc acaccctgtt cttcaacacc    1200
tggcgcatca tcaaggacgg cggcatcgac cccctggtgc gcggcctgct ggcgaagaag    1260
tccaagctga tgaaccagga caagatggtc accagcgagc tgcgcaacaa gctgttccag    1320
cccacccaca agatccacgg cttcgacctg gccgccatca acctgcagcg ctgccgcgac    1380
cacggcatgc ccggctacaa ctcgtggcgc ggcttctgcg gcctgagcca gcccaagacc    1440
ctgaagggcc tgcagaccgt gctgaagaac aagatcctgg ccaagaagct gatggacctg    1500
tacaagaccc ccgacaacat cgacatctgg atcggcggca acgccgagcc catggtggag    1560
cgcggccgcg tgggcccgct gctggcctgc ctgctgggcc gccagttcca gcagatccgc    1620
gacggcgacc gcttctggtg ggagaacccc ggcgtgttca ccgagaagca gcgcgacagc    1680
ctgcagaagg tgtccttcag ccgcctgatc tgcgacaaca cccacatcac caaggtgccg    1740
ctgcacgcct ccaggccaa caactacccc cacgacttcg tggactgctc caccgtggac    1800
aagctggacc tgtccccgtg ggccagccgc gagaac                              1836

<210> SEQ ID NO 40
<211> LENGTH: 4
<212> TYPE: PRT
<213> ORGANISM: Unknown
<220> FEATURE:
<223> OTHER INFORMATION: Description of Unknown: "DEAD" box motif
      peptide

<400> SEQUENCE: 40

Asp Glu Ala Asp
1

<210> SEQ ID NO 41
<211> LENGTH: 6
<212> TYPE: PRT
<213> ORGANISM: Unknown
<220> FEATURE:
<223> OTHER INFORMATION: Description of Unknown: Illustrative
      endoplasmic reticulum motif peptide
```

```
<400> SEQUENCE: 41

Phe Glu His Asp Glu Leu
1               5

<210> SEQ ID NO 42
<211> LENGTH: 4
<212> TYPE: PRT
<213> ORGANISM: Unknown
<220> FEATURE:
<223> OTHER INFORMATION: Description of Unknown: Illustrative
      endoplasmic reticulum motif peptide

<400> SEQUENCE: 42

Lys Asp Glu Leu
1

<210> SEQ ID NO 43
<211> LENGTH: 4
<212> TYPE: PRT
<213> ORGANISM: Unknown
<220> FEATURE:
<223> OTHER INFORMATION: Description of Unknown: Illustrative
      endoplasmic reticulum motif peptide

<400> SEQUENCE: 43

His Asp Glu Leu
1

<210> SEQ ID NO 44
<211> LENGTH: 4
<212> TYPE: PRT
<213> ORGANISM: Unknown
<220> FEATURE:
<223> OTHER INFORMATION: Description of Unknown: Illustrative
      endoplasmic reticulum motif peptide

<400> SEQUENCE: 44

Arg Asp Glu Leu
1

<210> SEQ ID NO 45
<211> LENGTH: 30
<212> TYPE: PRT
<213> ORGANISM: Chlamydomonas reinhardtii

<400> SEQUENCE: 45

Met His Ala Arg Lys Met Gly Ala Leu Ala Val Leu Ala Val Ala Cys
1               5                   10                  15

Leu Ala Ala Val Ala Ser Val Ala His Ala Ala Asp Thr Lys
            20                  25                  30

<210> SEQ ID NO 46
<211> LENGTH: 23
<212> TYPE: PRT
<213> ORGANISM: Chlamydomonas reinhardtii

<400> SEQUENCE: 46

Met Gly Ala Leu Ala Val Phe Ala Val Ala Cys Leu Ala Ala Val Ala
1               5                   10                  15

Ser Val Ala His Ala Ala Asp
            20

<210> SEQ ID NO 47
<211> LENGTH: 34
<212> TYPE: PRT
```

<213> ORGANISM: Chlamydomonas reinhardtii

<400> SEQUENCE: 47

Met Ala Gln Trp Lys Ala Ala Val Leu Leu Ala Leu Ala Cys Ala
1               5                   10                  15

Ser Tyr Gly Phe Gly Val Trp Ala Glu Glu Lys Leu Gly Thr Val
            20                  25                  30

Ile Gly

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtcgtgtcc acgaacttcc                                              20

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cacgcggcag ccctg                                                   15

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccttgtagtc ggatccgcag cccagcagct c                                 31

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ccttgtagtc ggatccggcg aagccgcgcg c                                 31

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtgctaggta actaacgttt gattttt                                      27

<210> SEQ ID NO 53

```
<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gggggagcga ataggattag                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccgaactgag gttgggttta                                              20

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55 ggaagggag gacgtaggta cataaa                                        26

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttagaacgtg ttttgttccc aat                                          23

<210> SEQ ID NO 57
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(429)

<400> SEQUENCE: 57 aag aag ttc cag cgc tgc gag ctg gcc cgc acc ctg aag aag ctg ggc      48
Lys Lys Phe Gln Arg Cys Glu Leu Ala Arg Thr Leu Lys Lys Leu Gly
 1               5                  10                  15 ctg gac ggc tac cgc ggc gtg tcc ctg gcc aac tgg gtg tgc ctg gcc      96
Leu Asp Gly Tyr Arg Gly Val Ser Leu Ala Asn Trp Val Cys Leu Ala
             20                  25                  30 cgc tgg gag agc aac tac aac acc cgc gcc acc aac tac aac cgc ggc     144
Arg Trp Glu Ser Asn Tyr Asn Thr Arg Ala Thr Asn Tyr Asn Arg Gly
         35                  40                  45 gac aag agc acc gac tac ggc atc ttc cag atc aac agc cgc tgg tgg     192
Asp Lys Ser Thr Asp Tyr Gly Ile Phe Gln Ile Asn Ser Arg Trp Trp
     50                  55                  60
```

```
tgc aac gac ggc aag acc ccc aag gcc gtg aac gcc tgc cgc atc ccc     240
Cys Asn Asp Gly Lys Thr Pro Lys Ala Val Asn Ala Cys Arg Ile Pro
 65                  70                  75                  80 tgc agc gcc ctg ctg aag gac gac atc acc cag gcc gtg gcc tgc gcc     288
Cys Ser Ala Leu Leu Lys Asp Asp Ile Thr Gln Ala Val Ala Cys Ala
                 85                  90                  95 aag cgc gtc gtg cgc gac ccc cag ggc atc aag gcg tgg gtg gcg tgg     336
Lys Arg Val Val Arg Asp Pro Gln Gly Ile Lys Ala Trp Val Ala Trp
            100                 105                 110 cgc aac aag tgc cag aac cgc gac ctg cgc agc tac gtg cag ggc tgc     384
Arg Asn Lys Cys Gln Asn Arg Asp Leu Arg Ser Tyr Val Gln Gly Cys
        115                 120                 125 cgc gtg gga tcc gac tac aag gac gac gac gac aag gac gag ctc taa    432
Arg Val Gly Ser Asp Tyr Lys Asp Asp Asp Asp Lys Asp Glu Leu
    130                 135                 140

<210> SEQ ID NO 58
<211> LENGTH: 1278
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1275)

<400> SEQUENCE: 58 ttc agc ggc gac ttc tgc gac agc agc cag tgc ctg cac ggc ggc acc     48
Phe Ser Gly Asp Phe Cys Asp Ser Ser Gln Cys Leu His Gly Gly Thr
  1               5                  10                  15 tgc ctg ctg aac gag gac cgc acc ccc ccc ttc tac tgc ctg tgc ccc     96
Cys Leu Leu Asn Glu Asp Arg Thr Pro Pro Phe Tyr Cys Leu Cys Pro
             20                  25                  30 gag ggc ttc acc ggc ctg ctg tgc aac gag acc gag cac ggc ccc tgc    144
Glu Gly Phe Thr Gly Leu Leu Cys Asn Glu Thr Glu His Gly Pro Cys
         35                  40                  45 ttc ccc aac ccc tgc cac aac gac gcc gag tgc cag gtg acc gac gac    192
Phe Pro Asn Pro Cys His Asn Asp Ala Glu Cys Gln Val Thr Asp Asp
     50                  55                  60 agc cac cgc ggc gac gtg ttc atc cag tac atc tgc aag tgc ccc ctg    240
Ser His Arg Gly Asp Val Phe Ile Gln Tyr Ile Cys Lys Cys Pro Leu
 65                  70                  75                  80 ggc tac gtg ggc atc cac tgc gag acc acc tgc acc tcg ccc ctg ggc    288
Gly Tyr Val Gly Ile His Cys Glu Thr Thr Cys Thr Ser Pro Leu Gly
                 85                  90                  95 atg cag acc ggc gcg atc gcc gac agc cag atc agc gcc agc agc atg    336
Met Gln Thr Gly Ala Ile Ala Asp Ser Gln Ile Ser Ala Ser Ser Met
            100                 105                 110 cac ctg ggc ttc atg ggc ctg cag cgc tgg gcc ccc gag ctg gcc cgc    384
His Leu Gly Phe Met Gly Leu Gln Arg Trp Ala Pro Glu Leu Ala Arg
        115                 120                 125 ctg cac cag acc ggc atc gtg aac gcc tgg acc agc ggc aac tac gac    432
Leu His Gln Thr Gly Ile Val Asn Ala Trp Thr Ser Gly Asn Tyr Asp
    130                 135                 140 aag aac ccg tgg att cag gtg aac ctg atg cgc aag atg tgg gtc acc    480
Lys Asn Pro Trp Ile Gln Val Asn Leu Met Arg Lys Met Trp Val Thr
145                 150                 155                 160 ggc gtc gtg acc cag ggc gcc agc cgc gcc ggc agc gcc gag tac ctg    528
Gly Val Val Thr Gln Gly Ala Ser Arg Ala Gly Ser Ala Glu Tyr Leu
                165                 170                 175
```

```
aag acc ttc aag gtg gcc tac agc acc gac ggc cgc cag ttc cag ttc    576
Lys Thr Phe Lys Val Ala Tyr Ser Thr Asp Gly Arg Gln Phe Gln Phe
            180                 185                 190 atc cag gtg gcc ggc cgc agc ggc gac aag atc ttc atc ggc aac gtg    624
Ile Gln Val Ala Gly Arg Ser Gly Asp Lys Ile Phe Ile Gly Asn Val
        195                 200                 205 aac aac tcc ggc ctg aag atc aac ctg ttc gac acc ccc ctg gag acc    672
Asn Asn Ser Gly Leu Lys Ile Asn Leu Phe Asp Thr Pro Leu Glu Thr
    210                 215                 220 cag tac gtg cgc ctg gtg ccc atc atc tgc cac cgc ggc tgc acc ctg    720
Gln Tyr Val Arg Leu Val Pro Ile Ile Cys His Arg Gly Cys Thr Leu
225                 230                 235                 240 cgc ttc gag ctg ctg ggc tgc gag ctg aac ggc tgc acc gag ccg ctg    768
Arg Phe Glu Leu Leu Gly Cys Glu Leu Asn Gly Cys Thr Glu Pro Leu
                245                 250                 255 ggc ctg aag gac aac acc atc ccc aac aag cag atc acc gcc tcc agc    816
Gly Leu Lys Asp Asn Thr Ile Pro Asn Lys Gln Ile Thr Ala Ser Ser
            260                 265                 270 tac tac aag acc tgg ggc ctg agc gcc ttc tcc tgg ttc ccc tac tac    864
Tyr Tyr Lys Thr Trp Gly Leu Ser Ala Phe Ser Trp Phe Pro Tyr Tyr
        275                 280                 285 gcc cgc ctg gac aac cag ggc aag ttc aac gcg tgg acc gcc cag acc    912
Ala Arg Leu Asp Asn Gln Gly Lys Phe Asn Ala Trp Thr Ala Gln Thr
    290                 295                 300 aac agc gcc tcc gag tgg ctg cag atc gac ctg ggc agc cag aag cgc    960
Asn Ser Ala Ser Glu Trp Leu Gln Ile Asp Leu Gly Ser Gln Lys Arg
305                 310                 315                 320 gtg acc ggc atc atc acc cag ggc gcg cgc gac ttc ggc cac atc cag   1008
Val Thr Gly Ile Ile Thr Gln Gly Ala Arg Asp Phe Gly His Ile Gln
                325                 330                 335 tac gtg gcc gcc tac cgc gtg gcc tac ggc gac gac ggc gtg acc tgg   1056
Tyr Val Ala Ala Tyr Arg Val Ala Tyr Gly Asp Asp Gly Val Thr Trp
            340                 345                 350 acc gag tac aag gac ccc ggc gcc agc gag agc aag atc ttc ccg ggc   1104
Thr Glu Tyr Lys Asp Pro Gly Ala Ser Glu Ser Lys Ile Phe Pro Gly
        355                 360                 365 aac atg gac aac aac agc cac aag aag aac atc ttc gag acc ccc ttc   1152
Asn Met Asp Asn Asn Ser His Lys Lys Asn Ile Phe Glu Thr Pro Phe
    370                 375                 380 cag gcc cgc ttc gtg cgc atc cag ccc gtg gcc tgg cac aac cgc atc   1200
Gln Ala Arg Phe Val Arg Ile Gln Pro Val Ala Trp His Asn Arg Ile
385                 390                 395                 400 acc ctg cgc gtg gag ctg ctg ggc tgc ggc ggc gga gga tcc gac tac   1248
Thr Leu Arg Val Glu Leu Leu Gly Cys Gly Gly Gly Gly Ser Asp Tyr
                405                 410                 415 aag gac gac gac gac aag gac gag ctc taa                            1278
Lys Asp Asp Asp Asp Lys Asp Glu Leu
            420                 425

<210> SEQ ID NO 59
<211> LENGTH: 837
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(834)

<400> SEQUENCE: 59 ctg ccc gtg aag ccc acc agc agc ggc agc agc gag gag aag cag ctg     48
```

```
Leu Pro Val Lys Pro Thr Ser Ser Gly Ser Ser Glu Glu Lys Gln Leu
1               5                   10                  15 aac aac aag tac ccc gac gcc gtg gcc acc tgg ctg aag ccc gac ccc    96
Asn Asn Lys Tyr Pro Asp Ala Val Ala Thr Trp Leu Lys Pro Asp Pro
                20                  25                  30 agc cag aag cag acc ttc ctg gcc ccc cag aac agc gtg tcc tcc gag   144
Ser Gln Lys Gln Thr Phe Leu Ala Pro Gln Asn Ser Val Ser Ser Glu
        35                  40                  45 gag acc gac gac aac aag cag aac acc ctg ccc agc aag agc aac gag   192
Glu Thr Asp Asp Asn Lys Gln Asn Thr Leu Pro Ser Lys Ser Asn Glu
    50                  55                  60 agc ccc gag cag acc gac gac ctg gac gac gac gac aac agc cag       240
Ser Pro Glu Gln Thr Asp Asp Leu Asp Asp Asp Asp Asn Ser Gln
65                  70                  75                  80 gac gtg aac agc aac gac agc gac gac gcc gag acc acc gac gac ccc   288
Asp Val Asn Ser Asn Asp Ser Asp Asp Ala Glu Thr Thr Asp Asp Pro
                85                  90                  95 gac cac agc gac gag agc cac cac tcc gac gag tcg gac gag gtg gac   336
Asp His Ser Asp Glu Ser His His Ser Asp Glu Ser Asp Glu Val Asp
                100                 105                 110 ttc ccc acc gac atc ccc acc atc gcg gtg ttc acc ccc ttc atc ccg   384
Phe Pro Thr Asp Ile Pro Thr Ile Ala Val Phe Thr Pro Phe Ile Pro
            115                 120                 125 acc gag agc gcc aac gac ggc cgc ggc gac agc gtg gcc tac ggc ctg   432
Thr Glu Ser Ala Asn Asp Gly Arg Gly Asp Ser Val Ala Tyr Gly Leu
130                 135                 140 aag tcc cgc agc aag aag ttc cgc cgc agc aac gtg cag tcg ccc gac   480
Lys Ser Arg Ser Lys Lys Phe Arg Arg Ser Asn Val Gln Ser Pro Asp
145                 150                 155                 160 gcc acc gag gag gac ttc acc tcc cac atc gag tcg gag gag atg cac   528
Ala Thr Glu Glu Asp Phe Thr Ser His Ile Glu Ser Glu Glu Met His
                165                 170                 175 gac gcc ccc aag aag acc agc cag ctg acc gac cac tcc aag gag acc   576
Asp Ala Pro Lys Lys Thr Ser Gln Leu Thr Asp His Ser Lys Glu Thr
            180                 185                 190 aac agc tcc gag ctg agc aag gag ctg acc ccc aag gcc aag gac aag   624
Asn Ser Ser Glu Leu Ser Lys Glu Leu Thr Pro Lys Ala Lys Asp Lys
        195                 200                 205 aac aag cac agc aac ctg atc gag agc cag gag aac agc aag ctg tcc   672
Asn Lys His Ser Asn Leu Ile Glu Ser Gln Glu Asn Ser Lys Leu Ser
    210                 215                 220 cag gag ttc cac agc ctg gag gac aag ctg gac ctg gac cac aag agc   720
Gln Glu Phe His Ser Leu Glu Asp Lys Leu Asp Leu Asp His Lys Ser
225                 230                 235                 240 gag gag gac aag cac ctg aag atc cgc atc agc cac gag ctg gac agc   768
Glu Glu Asp Lys His Leu Lys Ile Arg Ile Ser His Glu Leu Asp Ser
                245                 250                 255 gcc tcc agc gag gtg aac ggc ggc gga tcc gac tac aag gac gac       816
Ala Ser Ser Glu Val Asn Gly Gly Gly Ser Asp Tyr Lys Asp Asp
                260                 265                 270 gac gac aag gac gag ctc taa                                       837
Asp Asp Lys Asp Glu Leu
        275

<210> SEQ ID NO 60
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<220> FEATURE:
<221> NAME/KEY: CDS
<222> LOCATION: (1)..(417)

<400> SEQUENCE: 60 gag cag ctg acc aag tgc gag gtg ttc cgc gag ctg aag gac ctg aag       48
Glu Gln Leu Thr Lys Cys Glu Val Phe Arg Glu Leu Lys Asp Leu Lys
1               5                   10                  15 ggc tac ggc ggc gtg tcg ctg ccc gag tgg gtg tgc acc acc ttc cac       96
Gly Tyr Gly Gly Val Ser Leu Pro Glu Trp Val Cys Thr Thr Phe His
            20                  25                  30 acc agc ggc tac gac acc cag gcg atc gtg cag aac aac gac agc acc      144
Thr Ser Gly Tyr Asp Thr Gln Ala Ile Val Gln Asn Asn Asp Ser Thr
        35                  40                  45 gag tac ggc ctg ttc cag atc aac aac aag atc tgg tgc aag gac gac      192
Glu Tyr Gly Leu Phe Gln Ile Asn Asn Lys Ile Trp Cys Lys Asp Asp
    50                  55                  60 cag aac ccc cac agc agc aac atc tgc aac atc agc tgc gac aag ttc      240
Gln Asn Pro His Ser Ser Asn Ile Cys Asn Ile Ser Cys Asp Lys Phe
65                  70                  75                  80 ctg gac gac gac ctg acc gac gac att atg tgc gtg aag aag atc ctg      288
Leu Asp Asp Asp Leu Thr Asp Asp Ile Met Cys Val Lys Lys Ile Leu
                85                  90                  95 gac aag gtg ggc atc aac tac tgg ctg gcc cac aag gcc ctg tgc agc      336
Asp Lys Val Gly Ile Asn Tyr Trp Leu Ala His Lys Ala Leu Cys Ser
            100                 105                 110 gag aag ctg gac cag tgg ctg tgc gag aag ctg ggc ggc gga gga tcc      384
Glu Lys Leu Asp Gln Trp Leu Cys Glu Lys Leu Gly Gly Gly Gly Ser
        115                 120                 125 gac tac aag gac gac gac gac aag gac gag ctc taa                      420
Asp Tyr Lys Asp Asp Asp Asp Lys Asp Glu Leu
        130                 135

<210> SEQ ID NO 61
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(426)

<400> SEQUENCE: 61 cag gcc ctg agc tac cgc gag gcc gtg ctg cgc gcc gtg gac cag ctg       48
Gln Ala Leu Ser Tyr Arg Glu Ala Val Leu Arg Ala Val Asp Gln Leu
1               5                   10                  15 aac gag cag agc agc gag ccc aac atc tac cgc ctg ctg gag ctg gac       96
Asn Glu Gln Ser Ser Glu Pro Asn Ile Tyr Arg Leu Leu Glu Leu Asp
            20                  25                  30 cag ccc ccc cag gac gac gag gac ccc gac agc ccc aag cgc gtg tcc      144
Gln Pro Pro Gln Asp Asp Glu Asp Pro Asp Ser Pro Lys Arg Val Ser
        35                  40                  45 ttc cgc gtg aag gag acc gtg tgc agc cgc acc acc cag cag ccc ccc      192
Phe Arg Val Lys Glu Thr Val Cys Ser Arg Thr Thr Gln Gln Pro Pro
    50                  55                  60 gag cag tgc gac ttc aag gag aac ggc ctg ctg aag cgc tgc gag ggc      240
Glu Gln Cys Asp Phe Lys Glu Asn Gly Leu Leu Lys Arg Cys Glu Gly
65                  70                  75                  80 acc gtg acc ctg gac cag gtg cgc ggc aac ttc gac atc acc tgc aac      288
Thr Val Thr Leu Asp Gln Val Arg Gly Asn Phe Asp Ile Thr Cys Asn
                85                  90                  95
```

```
aac cac cag agc atc cgc atc acc aag cag ccg tgg gcc ccc ccg cag      336
Asn His Gln Ser Ile Arg Ile Thr Lys Gln Pro Trp Ala Pro Pro Gln
        100                 105                 110 gcc gcc cgc ctg tgc cgc atc gtc gtg atc cgc gtg tgc cgc ggc ggc      384
Ala Ala Arg Leu Cys Arg Ile Val Val Ile Arg Val Cys Arg Gly Gly
            115                 120                 125 gga gga tcc gac tac aag gac gac gac aag gac gag ctc taa              429
Gly Gly Ser Asp Tyr Lys Asp Asp Asp Lys Asp Glu Leu
        130                 135                 140

<210> SEQ ID NO 62
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(168)

<400> SEQUENCE: 62 gtg cgc aac agc cag agc tgc cgc cgc aac aag ggc atc tgc gtg ccc       48
Val Arg Asn Ser Gln Ser Cys Arg Arg Asn Lys Gly Ile Cys Val Pro
1               5                   10                  15 atc cgc tgc ccc ggc agc atg cgc cag atc ggc acc tgc ctg ggc gcc       96
Ile Arg Cys Pro Gly Ser Met Arg Gln Ile Gly Thr Cys Leu Gly Ala
            20                  25                  30 cag gtg aag tgc tgc cgc cgc aag ggc ggc gga gga tcc gac tac aag      144
Gln Val Lys Cys Cys Arg Arg Lys Gly Gly Gly Gly Ser Asp Tyr Lys
        35                  40                  45 gac gac gac gac aag gac gag ctc taa                                  171
Asp Asp Asp Asp Lys Asp Glu Leu
        50                  55

<210> SEQ ID NO 63
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1107)

<400> SEQUENCE: 63 gac acc acc gag ccc tgc gag ctg gac gac gac gac ttc cgc tgc gtg       48
Asp Thr Thr Glu Pro Cys Glu Leu Asp Asp Asp Asp Phe Arg Cys Val
1               5                   10                  15 tgc aac ttc acc gac ccc aag ccc gac tgg tcc agc gcc gtg cag tgc       96
Cys Asn Phe Thr Asp Pro Lys Pro Asp Trp Ser Ser Ala Val Gln Cys
            20                  25                  30 atg gtg gcc gtg gag gtg gag atc agc gcc ggc ggc cgc agc ctg gag      144
Met Val Ala Val Glu Val Glu Ile Ser Ala Gly Gly Arg Ser Leu Glu
        35                  40                  45 cag ttc ctg aag ggc gcg gac acc aac ccg aag cag tac gcc gac acc      192
Gln Phe Leu Lys Gly Ala Asp Thr Asn Pro Lys Gln Tyr Ala Asp Thr
    50                  55                  60 atc aag gcg ctg cgc gtg cgc cgc ctg aag ctg ggc gcg gcc cag gtg      240
Ile Lys Ala Leu Arg Val Arg Arg Leu Lys Leu Gly Ala Ala Gln Val
65                  70                  75                  80 ccc gcg cag ctg ctg gtg gcg gtg ctg cgc gcc ctg ggc tac tcg cgc      288
Pro Ala Gln Leu Leu Val Ala Val Leu Arg Ala Leu Gly Tyr Ser Arg
```

|  |  |  |  |  |  |  |  |  |  |  |  |  |  |  |  |
|---|---|---|---|---|---|---|---|---|---|---|---|---|---|---|---|
|  |  |  |  | 85 |  |  |  |  | 90 |  |  |  |  | 95 |  |
| ctg | aag | gag | ctg | acc | ctg | gag | gac | ctg | gag | gtg | acc | ggc | ccc | acc | ccc |
| Leu | Lys | Glu | Leu | Thr | Leu | Glu | Asp | Leu | Glu | Val | Thr | Gly | Pro | Thr | Pro |
|  |  |  | 100 |  |  |  |  | 105 |  |  |  |  | 110 |  |  |

336 ccg acc ccc ctg gag gcc gcg ggc ccc gcc ctg acc acc ctg agc ctg        384
Pro Thr Pro Leu Glu Ala Ala Gly Pro Ala Leu Thr Thr Leu Ser Leu
            115                 120                 125 cgc aac gtg tcc tgg acc acc ggc ggc gcc tgg ctg ggc gag ctg cag        432
Arg Asn Val Ser Trp Thr Thr Gly Gly Ala Trp Leu Gly Glu Leu Gln
130                 135                 140 cag tgg ctg aag ccc ggc ctg cgc gtg ctg aac atc gcc cag gcc cac        480
Gln Trp Leu Lys Pro Gly Leu Arg Val Leu Asn Ile Ala Gln Ala His
145                 150                 155                 160 agc ctg gcc ttc ccg tgc gcg ggc ctg agc acc ttc gag gcg ctg acc        528
Ser Leu Ala Phe Pro Cys Ala Gly Leu Ser Thr Phe Glu Ala Leu Thr
            165                 170                 175 acc ctg gac ctg agc gac aac ccc tcg ctg ggc gac agc ggc ctg atg        576
Thr Leu Asp Leu Ser Asp Asn Pro Ser Leu Gly Asp Ser Gly Leu Met
            180                 185                 190 gcc gcc ctg tgc ccc aac aag ttc ccc gcg ctg cag tac ctg gcg ctg        624
Ala Ala Leu Cys Pro Asn Lys Phe Pro Ala Leu Gln Tyr Leu Ala Leu
            195                 200                 205 cgc aac gcc ggc atg gag acc ccc agc ggc gtg tgc gcg gcg ctg gcc        672
Arg Asn Ala Gly Met Glu Thr Pro Ser Gly Val Cys Ala Ala Leu Ala
210                 215                 220 gcc gcc cgc gtg cag ccc cag tcg ctg gac ctg tcc cac aac tcc ctg        720
Ala Ala Arg Val Gln Pro Gln Ser Leu Asp Leu Ser His Asn Ser Leu
225                 230                 235                 240 cgc gtg acc gcg ccc ggc gcc acc cgc tgc gtg tgg ccc agc gcc ctg        768
Arg Val Thr Ala Pro Gly Ala Thr Arg Cys Val Trp Pro Ser Ala Leu
            245                 250                 255 cgc agc ctg aac ctg agc ttc gcc ggc ctg gag cag gtg ccc aag ggc        816
Arg Ser Leu Asn Leu Ser Phe Ala Gly Leu Glu Gln Val Pro Lys Gly
            260                 265                 270 ctg ccc ccc aag ctg agc gtg ctg gac ctg agc tgc aac aag ctg agc        864
Leu Pro Pro Lys Leu Ser Val Leu Asp Leu Ser Cys Asn Lys Leu Ser
            275                 280                 285 cgc gag ccg cgc cgc gac gag ctg ccc gag gtg aac gac ctg acc ctg        912
Arg Glu Pro Arg Arg Asp Glu Leu Pro Glu Val Asn Asp Leu Thr Leu
            290                 295                 300 gac ggc aac ccc ttc ctg gac ccg ggc gcc ctg cag cac cag aac gac        960
Asp Gly Asn Pro Phe Leu Asp Pro Gly Ala Leu Gln His Gln Asn Asp
305                 310                 315                 320 ccc atg atc tcc ggc gtg gtg ccc gcc tgc gcc cgc tcg gcc ctg acc       1008
Pro Met Ile Ser Gly Val Val Pro Ala Cys Ala Arg Ser Ala Leu Thr
            325                 330                 335 atg ggc gtg tcg ggc gcg ctg gcc ctg ctg cag ggc gcg cgc ggc ttc       1056
Met Gly Val Ser Gly Ala Leu Ala Leu Leu Gln Gly Ala Arg Gly Phe
            340                 345                 350 gcc ggc ggc gga gga tcc gac tac aag gac gac gac gac aag gac gag       1104
Ala Gly Gly Gly Gly Ser Asp Tyr Lys Asp Asp Asp Asp Lys Asp Glu
            355                 360                 365 ctc taa                                                                1110
Leu

<210> SEQ ID NO 64
<211> LENGTH: 1878
<212> TYPE: DNA
<213> ORGANISM: Artificial Sequence
<220> FEATURE:

<223> OTHER INFORMATION: Description of Artificial Sequence: Synthetic polynucleotide
<220> FEATURE:
<221> NAME/KEY: CDS
<222> LOCATION: (1)..(1875)

<400> SEQUENCE: 64

```
gac acc acc ctg acc aac gtg acc gac ccc agc ctg gac ctg acc gcc      48
Asp Thr Thr Leu Thr Asn Val Thr Asp Pro Ser Leu Asp Leu Thr Ala
1               5                   10                  15 ctg agc tgg gag gtg ggc tgc ggc gcc ccc gtg ccc ctg gtc aag tgc      96
Leu Ser Trp Glu Val Gly Cys Gly Ala Pro Val Pro Leu Val Lys Cys
            20                  25                  30 gac gag aac agc ccc tac cgc acc atc acc ggc gac tgc aac aac cgc     144
Asp Glu Asn Ser Pro Tyr Arg Thr Ile Thr Gly Asp Cys Asn Asn Arg
        35                  40                  45 cgc tcc ccc gcc ctg ggc gcc gcc aac cgc gcc ctg gcc cgc tgg ctg     192
Arg Ser Pro Ala Leu Gly Ala Ala Asn Arg Ala Leu Ala Arg Trp Leu
    50                  55                  60 ccc gcc gag tac gag gac ggc ctg gcc ctg ccc ttc ggc tgg acc cag     240
Pro Ala Glu Tyr Glu Asp Gly Leu Ala Leu Pro Phe Gly Trp Thr Gln
65                  70                  75                  80 cgc aag acc cgc aac ggc ttc cgc gtg ccg ctg gcc cgc gag gtg tcc     288
Arg Lys Thr Arg Asn Gly Phe Arg Val Pro Leu Ala Arg Glu Val Ser
                85                  90                  95 aac aag atc gtg ggc tac ctg gac gag gag ggc gtg ctg gac cag aac     336
Asn Lys Ile Val Gly Tyr Leu Asp Glu Glu Gly Val Leu Asp Gln Asn
            100                 105                 110 cgc agc ctg ctg ttc atg cag tgg ggc cag atc gtg gac cac gac ctg     384
Arg Ser Leu Leu Phe Met Gln Trp Gly Gln Ile Val Asp His Asp Leu
        115                 120                 125 gac ttc gcc ccc gag acc gag ctg ggc agc aac gag cac agc aag acc     432
Asp Phe Ala Pro Glu Thr Glu Leu Gly Ser Asn Glu His Ser Lys Thr
    130                 135                 140 cag tgc gag gag tac tgc atc cag ggc gac aac tgc ttc ccc atc atg     480
Gln Cys Glu Glu Tyr Cys Ile Gln Gly Asp Asn Cys Phe Pro Ile Met
145                 150                 155                 160 ttc ccc aag aac gac ccc aag ctg aag acc cag ggc aag tgc atg ccg     528
Phe Pro Lys Asn Asp Pro Lys Leu Lys Thr Gln Gly Lys Cys Met Pro
                165                 170                 175 ttc ttc cgc gcc ggc ttc gtg tgc ccc acc ccc ccg tac cag agc ctg     576
Phe Phe Arg Ala Gly Phe Val Cys Pro Thr Pro Pro Tyr Gln Ser Leu
            180                 185                 190 gcg cgc gag cag atc aac gcc gtg acc tcg ttc ctg gac gcc agc ctg     624
Ala Arg Glu Gln Ile Asn Ala Val Thr Ser Phe Leu Asp Ala Ser Leu
        195                 200                 205 gtg tac ggc agc gag ccc tcc ctg gcc tcc cgc ctg cgc aac ctg tcc     672
Val Tyr Gly Ser Glu Pro Ser Leu Ala Ser Arg Leu Arg Asn Leu Ser
    210                 215                 220 agc ccc ctg ggc ctg atg gcc gtg aac cag gag gcc tgg gac cac ggc     720
Ser Pro Leu Gly Leu Met Ala Val Asn Gln Glu Ala Trp Asp His Gly
225                 230                 235                 240 ctg gcc tac ctg ccc ttc aac aac aag aag ccc agc ccc tgc gag ttc     768
Leu Ala Tyr Leu Pro Phe Asn Asn Lys Lys Pro Ser Pro Cys Glu Phe
                245                 250                 255 atc aac acc acc gcc cgc gtg ccc tgc ttc ctg gcg ggc gac ttc cgc     816
Ile Asn Thr Thr Ala Arg Val Pro Cys Phe Leu Ala Gly Asp Phe Arg
            260                 265                 270 gcg tcg gag cag atc ctg ctg gcc acc gcc cac acc ctg ctg ctg cgc     864
Ala Ser Glu Gln Ile Leu Leu Ala Thr Ala His Thr Leu Leu Leu Arg
        275                 280                 285
```

```
gag cac aac cgc ctg gcc cgc gag ctg aag aag ctg aac ccc cac tgg      912
Glu His Asn Arg Leu Ala Arg Glu Leu Lys Lys Leu Asn Pro His Trp
    290                 295                 300 aac ggc gag aag ctg tac cag gag gcg cgc aag atc ctg ggc gcc ttc      960
Asn Gly Glu Lys Leu Tyr Gln Glu Ala Arg Lys Ile Leu Gly Ala Phe
305                 310                 315                 320 atc cag atc atc acc ttc cgc gac tac ctg ccg atc gtg ctg ggc tcc     1008
Ile Gln Ile Ile Thr Phe Arg Asp Tyr Leu Pro Ile Val Leu Gly Ser
                325                 330                 335 gag atg cag aag tgg att ccg ccc tac cag ggc tac aac aac agc gtg     1056
Glu Met Gln Lys Trp Ile Pro Pro Tyr Gln Gly Tyr Asn Asn Ser Val
340                 345                 350 gac ccc cgc atc agc aac gtg ttc acc ttc gcc ttc cgc ttc ggc cac     1104
Asp Pro Arg Ile Ser Asn Val Phe Thr Phe Ala Phe Arg Phe Gly His
                355                 360                 365 atg gag gtg ccc agc acc gtg tcc cgc ctg gac gag aac tac cag ccc     1152
Met Glu Val Pro Ser Thr Val Ser Arg Leu Asp Glu Asn Tyr Gln Pro
370                 375                 380 tgg ggc ccc gag gcg gag ctg ccc ctg cac acc ctg ttc ttc aac acc     1200
Trp Gly Pro Glu Ala Glu Leu Pro Leu His Thr Leu Phe Phe Asn Thr
385                 390                 395                 400 tgg cgc atc atc aag gac ggc ggc atc gac ccc ctg gtg cgc ggc ctg     1248
Trp Arg Ile Ile Lys Asp Gly Gly Ile Asp Pro Leu Val Arg Gly Leu
                405                 410                 415 ctg gcg aag aag tcc aag ctg atg aac cag gac aag atg gtc acc agc     1296
Leu Ala Lys Lys Ser Lys Leu Met Asn Gln Asp Lys Met Val Thr Ser
            420                 425                 430 gag ctg cgc aac aag ctg ttc cag ccc acc cac aag atc cac ggc ttc     1344
Glu Leu Arg Asn Lys Leu Phe Gln Pro Thr His Lys Ile His Gly Phe
        435                 440                 445 gac ctg gcc gcc atc aac ctg cag cgc tgc cgc gac cac ggc atg ccc     1392
Asp Leu Ala Ala Ile Asn Leu Gln Arg Cys Arg Asp His Gly Met Pro
    450                 455                 460 ggc tac aac tcg tgg cgc ggc ttc tgc ggc ctg agc cag ccc aag acc     1440
Gly Tyr Asn Ser Trp Arg Gly Phe Cys Gly Leu Ser Gln Pro Lys Thr
465                 470                 475                 480 ctg aag ggc ctg cag acc gtg ctg aag aac aag atc ctg gcc aag aag     1488
Leu Lys Gly Leu Gln Thr Val Leu Lys Asn Lys Ile Leu Ala Lys Lys
                485                 490                 495 ctg atg gac ctg tac aag acc ccc gac aac atc gac atc tgg atc ggc     1536
Leu Met Asp Leu Tyr Lys Thr Pro Asp Asn Ile Asp Ile Trp Ile Gly
            500                 505                 510 ggc aac gcc gag ccc atg gtg gag cgc ggc cgc gtg ggc ccg ctg ctg     1584
Gly Asn Ala Glu Pro Met Val Glu Arg Gly Arg Val Gly Pro Leu Leu
        515                 520                 525 gcc tgc ctg ctg ggc cgc cag ttc cag cag atc cgc gac ggc gac cgc     1632
Ala Cys Leu Leu Gly Arg Gln Phe Gln Gln Ile Arg Asp Gly Asp Arg
    530                 535                 540 ttc tgg tgg gag aac ccc ggc gtg ttc acc gag aag cag cgc gac agc     1680
Phe Trp Trp Glu Asn Pro Gly Val Phe Thr Glu Lys Gln Arg Asp Ser
545                 550                 555                 560 ctg cag aag gtg tcc ttc agc cgc ctg atc tgc gac aac acc cac atc     1728
Leu Gln Lys Val Ser Phe Ser Arg Leu Ile Cys Asp Asn Thr His Ile
                565                 570                 575 acc aag gtg ccg ctg cac gcc ttc cag gcc aac aac tac ccc cac gac     1776
Thr Lys Val Pro Leu His Ala Phe Gln Ala Asn Asn Tyr Pro His Asp
            580                 585                 590 ttc gtg gac tgc tcc acc gtg gac aag ctg gac ctg tcc ccg tgg gcc     1824
Phe Val Asp Cys Ser Thr Val Asp Lys Leu Asp Leu Ser Pro Trp Ala
```

```
                    595                 600                 605
agc cgc gag aac gga tcc gac tac aag gac gac gac gac aag gac gag     1872
Ser Arg Glu Asn Gly Ser Asp Tyr Lys Asp Asp Asp Asp Lys Asp Glu
    610                 615                 620 ctc taa                                                              1878
Leu
625

<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 65 atg tgg ggc acc ttc ctg aag gag gcg ggc cag ggc gcg aag gac atg      48
Met Trp Gly Thr Phe Leu Lys Glu Ala Gly Gln Gly Ala Lys Asp Met
1               5                   10                  15 tgg cgc gcc tac cag gac atg aag gag gcc aac tac cgc ggc gcg gac      96
Trp Arg Ala Tyr Gln Asp Met Lys Glu Ala Asn Tyr Arg Gly Ala Asp
                20                  25                  30 aag tac ttc cac gcc cgc ggc aac tac gac gcg gcc cgc cgc ggc ccc     144
Lys Tyr Phe His Ala Arg Gly Asn Tyr Asp Ala Ala Arg Arg Gly Pro
            35                  40                  45 ggc ggc gcg tgg gcg gcg aag gtg atc agc aac gcg cgc gag acc atc     192
Gly Gly Ala Trp Ala Ala Lys Val Ile Ser Asn Ala Arg Glu Thr Ile
        50                  55                  60 cag ggc atc acc gac ccc ctg ttc aag ggc atg acc cgc gac cag gtg     240
Gln Gly Ile Thr Asp Pro Leu Phe Lys Gly Met Thr Arg Asp Gln Val
65                  70                  75                  80 cgc gag gac agc aag gcc gac cag ttc gcg aac gag tgg ggc cgc agc     288
Arg Glu Asp Ser Lys Ala Asp Gln Phe Ala Asn Glu Trp Gly Arg Ser
                85                  90                  95 ggc aag gac ccc aac cac ttc cgc ccc gcg ggc ctg ccc gac aag tac     336
Gly Lys Asp Pro Asn His Phe Arg Pro Ala Gly Leu Pro Asp Lys Tyr
            100                 105                 110 tag                                                                  339
```

COLOSTRUM/MILK PROTEIN COMPOSITIONS

CROSS-REFERENCE TO RELATED APPLICATIONS

This application is the U.S. National Phase under 35 U.S.C. § 371 of Intl. Appl. No. PCT/US2015/016596, filed on Feb. 19, 2015, which claims the benefit under 35 U.S.C. § 119(e) of U.S. Provisional Application No. 61/942,024, filed on Feb. 19, 2014, which are hereby incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Mar. 23, 2015, is named UCSDP033AWO_SL.txt and is 103 kilobytes in size.

FIELD

Provided are colostrum and milk polypeptides recombinantly expressed in photosynthetic organisms, compositions comprising such organisms and methods for producing such organisms.

BACKGROUND

Colostrum or milk bioactive proteins have only been available from the natural source (e.g., human and bovine colostrum or milk); because natural sources are in very limited supply, so too are the associated bioactives contained in them. Tailored combinations of colostrum and milk bioactives have never been available. Bioactive colostrum and milk proteins require both polypeptide accumulation and correct protein folding and post-translational modification.

SUMMARY

The invention provides a solution to drawbacks associated with conventional recombinant protein production methods. For example, the methods feature photosynthetic organisms such as the *Chlamydomonas reinhardtii*, a single-cell green alga, engineered to contain nucleic acids encoding a milk or colostrum protein in the nucleus. As a result, the organism produces recombinant biologically active mammalian proteins in the nucleus. Algae's ability to fold, assemble and accumulate multiple domain proteins as soluble molecules with appropriate post-translational modification, e.g. glycosylation or phosphorylation, to preserve biological activity, offers significant advantages. The organisms, isolated cells, and/or sub-cellular organelles, or secreted from the cell, are useful to produce proteins, which are rare or non-existent in the plant genome/proteome. The proteins produced can be delivered without purification, compared to conventional bioreactor systems, e.g., CHO, bacteria, or yeast, to yield bioactive compounds useful in an edible delivery system.

Accordingly provided are photosynthetic organisms, e.g., algae, as well as cells purified from populations of such organisms and/or sub-cellular organelles, e.g., nuclei, purified or obtained from such organism of a photosynthetic organism. In one aspect, provided is a nucleus or nuclear genome comprising one or more polynucleotides encoding one or more mammalian milk or colostrum polypeptides selected from soluble CD14 (sCD14), lactadherin, lactoperoxidase, milk lysozyme, osteopontin, cathelicidin-1, lingual antimicrobial peptide (LAP) and alpha-lactalbumin. In varying embodiments, the nucleus or nuclear genome is from a vascular plant. In varying embodiments the nucleus or nuclear genome is from a non-vascular photosynthetic eukaryotic organism. In varying embodiments, the nucleus or nuclear genome is from a photosynthetic unicellular organism. In varying embodiments, the nucleus or nuclear genome is from a microalgae. In some embodiments, the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae). In some embodiments, the photosynthetic organism is selected from the group consisting of *Chlamydomonas reinhardtii, Dunaliella salina, Haematococcus pluvialis, Chlorella vulgaris, Acutodesmus obliquus,* and *Scenedesmus dimorphus*. In some embodiments, the nucleus or nuclear genome is a Chlorophyta (green algae) nucleus or nuclear genome. In some embodiments, the green alga is selected from the group consisting of *Chlamydomonas, Dunaliella, Haematococcus, Chlorella*, and Scenedesmaceae. In some embodiments, the *Chlamydomonas* is a *Chlamydomonas reinhardtii*. In varying embodiments, the green algae can be a Chlorophycean, a *Chlamydomonas, C. reinhardtii, C. reinhardtii* cc1690, or a psbA deficient *C. reinhardtii* strain. In varying embodiments, the nucleus or nuclear genome is from a higher plant selected from Brassicaceae, Solanaceae, Phaseoleae, *Zea* and Oryzeae. In some embodiments, the one or more mammalian polypeptides further comprises one or more mammalian milk or colostrum polypeptides selected from immunoglobulins (e.g., IgG1, IgG2, IgA, IgM, IgD), lactoferrin, mammary associated serum amyloid A3 (MAA), proline rich polypeptide (PRP), growth factors (e.g., transforming growth factor (TGF)-β1, TGF-β2, insulin-like growth factor 1 (somatomedin C) (IGF-1), IGF-2, epidermal growth factor, heparin-binding epidermal growth factor-like growth factor, betacellulin), cytokines (e.g., IL-6, IL-1β, IL 1ra) serum albumin, glycomacropeptide, casein proteins (e.g., β-casein, κ-casein, αs1 casein, αs2-casein and γ-casein), enzymes (e.g., superoxide dismutase, lactoperoxidase, alkaline phosphatase, platelet-activating factor-acetylhydroxylase, lysozyme), 14-3-3 protein zeta chain, 5-oxoprolinase (ATP-hydrolyzing), actin, cytoplasmic 1 (beta-actin), adipose differentiation-related protein, albumin (precursor), aldehyde dehydrogenase (NAD) 2 precursor, ankyrin 3, node of Ranvier (ankyrin G), annexin 1, annexin A2, apolipoprotein A-I, apolipoprotein B, ARP3 (actin-related protein 3, yeast) homolog, ATP synthase, H+ transporting, mitochondrial, F1 complex, alpha subunit, beta-2-microglobulin precursor (lactollin); butyrophilin, subfamily 1, member A1; capping protein (actin filament); muscle Z-line, alpha 1; casein kinase 1, alpha 1; coronin, actin binding protein, 1A; CD36 antigen [collagen type I receptor, thrombospondin receptor]; Chitinase-like protein 1 (CLP-1); DEAD (Asp-Glu-Ala-Asp) box (SEQ ID NO: 40) polypeptide 54; deleted in malignant brain tumors 1; diacylglycerol kinase kappa; endoplasmin precursor (GRP94/GP96); enolase 1; eukaryotic translation initiation factor 4, gamma 2;

fatty acid binding protein, heart-type (MDGI); fetuin; fibrinogen alpha chain; fibrinogen beta chain precursor; fibrinogen gamma-B chain precursor; gene model 440, (NCBI); glucose regulated protein 58 kD; glutamate receptor, ionotropic, delta 1; glutathione S-transferase, mu 1; glyceraldehyde-3-phosphate; dehydrogenase (GAPDH); glycerol-3-phosphate dehydrogenase 2; glycoprotein antigen MGP57/53 (Lactadherin/bP47 protein); glycosylation-dependent cell adhesion molecule 1 (lactophorin/PP3); guanine nucleotide binding protein, beta 2; H3 histone, family 3A; heat shock 70 kDa protein 8; heat shock 70 kD protein 5 (glucose-regulated protein); heat shock protein 27; heat shock protein 70 kDa protein 1A; histone 2, H2ab; zinc finger protein 668; hypothetical/unnamed protein L0051063; IRTA2; isocitrate dehydrogenase 1 (NADP+), soluble; keratin 9; keratin complex 2, basic, gene 6a; keratin, type I cytoskeletal 10; and KIAA1586 protein. In varying embodiments, the one or more mammalian polypeptides are bioactive. In some embodiments, the nucleus or nuclear genome comprises at least two (e.g., at least 3, 4, 5, 6, 7, 8, 9 or 10) polynucleotides encoding at least two mammalian milk or colostrum polypeptides. In some embodiments, the at least two mammalian milk or colostrum polypeptides comprise lysozyme and mammary associated serum amyloid A3 (MAA). In some embodiments, the at least two mammalian milk or colostrum polypeptides comprise osteopontin and mammary associated serum amyloid A3 (MAA). In some embodiments, i) the polynucleotide encoding mammary associated serum amyloid A3 (MAA) is integrated into the nuclear genome, and the expressed protein is targeted to the cytoplasm; and ii) the polynucleotide encoding osteopontin is integrated into the nuclear genome, and the expressed protein is targeted to the endoplasmic reticulum; or iii) the polynucleotide encoding osteopontin is integrated into the nuclear genome, and the expressed protein is targeted to a plastid (e.g., chloroplast, leucoplast, amyloplast, etc.). In some embodiments, one or more polynucleotides encoding the one or more mammalian polypeptides is integrated into the nuclear genome. In some embodiments, one or more nucleic acids encoding the one or more mammalian polypeptides selected from osteopontin, mammary associated serum amyloid A3 (MAA), lactoperoxidase, alpha-lactalbumin, lysozyme, soluble CD14, lingual antimicrobial peptide (LAP), cathelicidin-1, and lactadherin is integrated into the nuclear genome. In some embodiments, the one or more mammalian polypeptides are human milk or colostrum polypeptides. In some embodiments, the one or more polypeptides are milk or colostrum polypeptides from a mammal selected from the group consisting of canine, feline, bovine, porcine, ovine and caprine. In some embodiments, the nucleic acid encoding lysozyme comprises a polynucleotide having at least about 60% sequence identity, e.g., at least about 65%, 70%, 75%, 80%, 85%, 90%, 95%, 98% or 99% sequence identity, to SEQ ID NO:27. In some embodiments, the nucleic acid encoding soluble CD14 comprises a polynucleotide having at least about 60% sequence identity, e.g., at least about 65%, 70%, 75%, 80%, 85%, 90%, 95%, 98% or 99% sequence identity, to SEQ ID NO:33. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:23. In some embodiments, the nucleic acid encoding alpha-lactalbumin comprises a polynucleotide having at least about 60% sequence identity, e.g., at least about 65%, 70%, 75%, 80%, 85%, 90%, 95%, 98% or 99% sequence identity, to SEQ ID NO:29. In some embodiments, the nucleic acid encoding lingual antimicrobial peptide comprises a polynucleotide having at least about 60% sequence identity, e.g., at least about 65%, 70%, 75%, 80%, 85%, 90%, 95%, 98% or 99% sequence identity, to SEQ ID NO:31.

In some embodiments, the nucleic acid encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:25. In some embodiments, the nucleic acid encoding lactoperoxidase comprises a polynucleotide having at least about 60% sequence identity, e.g., at least about 65%, 70%, 75%, 80%, 85%, 90%, 95%, 98% or 99% sequence identity, to SEQ ID NO:39. In some embodiments, the nucleic acid encoding mammary associated serum amyloid A3 (MAA) comprises a polynucleotide having at least about 60% sequence identity, e.g., at least about 65%, 70%, 75%, 80%, 85%, 90%, 95%, 98% or 99% sequence identity, to SEQ ID NO:18. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:21. In some embodiments, the one or more mammalian polypeptides are glycosylated. For example, proteins produced in the nuclei of photosynthetic organisms (e.g., algae) are post-translationally modified by glycosylation with a high level of fidelity compared to the same protein produced in other recombinant production systems. In varying embodiments, colostrum/milk polypeptides produced in the nuclei of photosynthetic organisms (e.g., algae) are characterized by at least 50%, 75%, 85%, 90%, 95% 98%, 99% and even up to 100% of the level of bioactivity of the natural colostrum-derived counterpart protein. In some embodiments, the one or more mammalian polypeptides comprise an amino acid sequence that promotes retention in the endoplasmic reticulum. In some embodiments, the one or more mammalian polypeptides comprise an amino acid sequence that promotes secretion from the cell. In some embodiments, the one or more mammalian polypeptides comprise an amino acid sequence that promotes retention on the plasma membrane of a cell. In some embodiments, the one or more mammalian polypeptides comprise an amino acid sequence that promotes protein accumulation.

In a further aspect, provided are cells from a photosynthetic organism, the cells comprising one or more polynucleotides encoding one or more mammalian milk or colostrum polypeptides selected from soluble CD14 (sCD14), lactadherin, lactoperoxidase, milk lysozyme, osteopontin, cathelicidin-1, lingual antimicrobial peptide and alpha-lactalbumin. In varying embodiments, the cell is from a non-vascular photosynthetic eukaryotic organism. In varying embodiments, the cell is from a photosynthetic unicellular organism. In varying embodiments, the cell is from a microalgae. In varying embodiments, the cell is from a cyanobacteria. In some embodiments, the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae). In some embodiments, the photosynthetic organism is selected from the group consisting of *Chlamydomonas reinhardtii, Dunaliella salina, Haematococcus pluvialis, Chlorella vulgaris, Acutodesmus obliquus, Scenedesmus dimorphus, Arthrospira platensis, Arthrospira maxima, Anabaena* sp. PCC7120, *Leptolyngbya* sp, *Synechocystis* sp, and *Synechococcus* elongates PCC7942. In some embodiments, the cell is a Chlorophyta (green algae) cell. In some embodiments, the green alga is selected from the group consisting of *Chlamydomonas, Dunaliella, Haematococcus, Chlorella*, and *Scenedesmaceae*. In some embodiments, the *Chlamydomonas* is a *Chlamydomonas reinhardtii*. In varying embodiments, the green algae can be a *Chlorophycean*, a *Chlamydomonas, C. reinhardtii, C. reinhardtii* 137c, *C. reinhardtii* cc1690 or a psbA deficient *C. reinhardtii* strain. In varying embodiments, the cell is from a higher plant selected from Brassicaceae, Solanaceae, Phaseoleae, *Zea* and Oryzeae. In some embodiments, the cell comprises at least two (e.g., at least 3, 4, 5, 6, 7, 8, 9 or 10) polynucleotides encoding at least two mammalian milk or colostrum polypeptides. In some embodiments, the at least two mammalian milk or colostrum polypeptides comprise osteopontin and mammary associated serum amyloid A3 (MAA). In some embodiments, i) the polynucleotide encoding mammary associated serum amyloid A3 (MAA) is integrated into the nuclear genome, and the expressed protein is targeted to the cytoplasm; and ii) the polynucleotide encoding osteopontin is integrated into the nuclear genome, and the expressed protein is targeted to the endoplasmic reticulum; iii) the polynucleotide encoding osteopontin is integrated into the nuclear genome, and the expressed protein is targeted to a plastid (e.g., chloroplast, leucoplast, amyloplast, etc.); or iv) the polynucleotide encoding osteopontin is integrated into a plastid genome. In some embodiments, the at least two mammalian milk or colostrum polypeptides comprise lysozyme and mammary associated serum amyloid A3 (MAA). In some embodiments, the one or more mammalian polypeptides further comprises one or more mammalian milk or colostrum polypeptides selected from immunoglobulins (e.g., IgG1, IgG2, IgA, IgM, IgD), lactoferrin, mammary associated serum amyloid A3 (MAA), proline rich polypeptide (PRP), growth factors (e.g., transforming growth factor (TGF)-β1, TGF-β2, insulin-like growth factor 1 (somatomedin C) (IGF-1), IGF-2, epidermal growth factor, heparin-binding epidermal growth factor-like growth factor, betacellulin), cytokines (e.g., IL-6, IL-1β, IL 1ra) serum albumin, glycomacropeptide, casein proteins (e.g., β-casein, κ-casein, αs1 casein, αs2-casein and γ-casein), enzymes (e.g., superoxide dismutase, lactoperoxidase, alkaline phosphatase, platelet-activating factor-acetylhydroxylase, lysozyme), 14-3-3 protein zeta chain, 5-oxoprolinase (ATP-hydrolyzing), actin, cytoplasmic 1 (beta-actin), adipose differentiation-related protein, albumin (precursor), aldehyde dehydrogenase (NAD) 2 precursor, ankyrin 3, node of Ranvier (ankyrin G), annexin 1, annexin A2, apolipoprotein A-I, apolipoprotein B, ARP3 (actin-related protein 3, yeast) homolog, ATP synthase, H+ transporting, mitochondrial, F1 complex, alpha subunit, beta-2-microglobulin precursor (lactollin); butyrophilin, subfamily 1, member A1; capping protein (actin filament); muscle Z-line, alpha 1; casein kinase 1, alpha 1; coronin, actin binding protein, 1A; CD36 antigen [collagen type I receptor, thrombospondin receptor]; Chitinase-like protein 1 (CLP-1); DEAD (Asp-Glu-Ala-Asp) box (SEQ ID NO: 40) polypeptide 54; deleted in malignant brain tumors 1; diacylglycerol kinase kappa; endoplasmin precursor (GRP94/GP96); enolase 1; eukaryotic translation initiation factor 4, gamma 2; fatty acid binding protein, heart-type (MDGI); fetuin; fibrinogen alpha chain; fibrinogen beta chain precursor; fibrinogen gamma-B chain precursor; gene model 440, (NCBI); glucose regulated protein 58 kD; glutamate receptor, ionotropic, delta 1; glutathione S-transferase, mu 1; glyceraldehyde-3-phosphate; dehydrogenase (GAPDH); glycerol-3-phosphate dehydrogenase 2; glycoprotein antigen MGP57/53 (Lactadherin/bP47 protein); glycosylation-dependent cell adhesion molecule 1 (lactophorin/PP3); guanine nucleotide binding protein, beta 2; H3 histone, family 3A; heat shock 70 kDa protein 8; heat shock 70 kD protein 5 (glucose-regulated protein); heat shock protein 27; heat shock protein 70 kDa protein 1A; histone 2, H2ab; zinc finger protein 668; hypothetical/unnamed protein L0051063; IRTA2; isocitrate dehydrogenase 1 (NADP+), soluble; keratin 9; keratin complex 2, basic, gene 6a; keratin, type I cytoskeletal 10; and KIAA1586 protein. In varying embodiments, the one or more mammalian polypeptides are bioactive. In some embodiments, one or more polynucleotides encoding the one or more mammalian polypeptides is integrated into the chloroplast genome or the nuclear genome of the cell, or a cyanobacterial genome, or on a cyanobacterial plasmid. In some embodiments, the one or more mammalian polypeptides are human milk or colostrum polypeptides. In some embodiments, the one or more polypeptides are milk or colostrum polypeptides from a mammal selected from the group consisting of canine, feline, bovine, porcine, ovine and caprine. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:21. In some embodiments, the nucleic acid encoding lactoperoxidase comprises a polynucleotide having at least about 60% sequence identity, e.g., at least about 65%, 70%, 75%, 80%, 85%, 90%, 95%, 98% or 99% sequence identity, to SEQ ID NO:39. In some embodiments, the polynucleotide encoding lysozyme comprises a polynucleotide having at least about 60% sequence identity, e.g., at least about 65%, 70%, 75%, 80%, 85%, 90%, 95%, 98% or 99% sequence identity, to SEQ ID NO:27. In some embodiments, the nucleic acid encoding soluble CD14 comprises a polynucleotide having at least about 60% sequence identity, e.g., at least about 65%, 70%, 75%, 80%, 85%, 90%, 95%, 98% or 99% sequence identity, to SEQ ID NO:33. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:23. In some embodiments, the nucleic acid encoding alpha-lactalbumin comprises a polynucleotide having at least about 60% sequence identity, e.g., at least about 65%, 70%, 75%, 80%, 85%, 90%, 95%, 98% or 99% sequence identity, to SEQ ID NO:29. In some embodiments, the nucleic acid encoding lingual antimicrobial peptide comprises a polynucleotide having at least about 60% sequence identity, e.g., at least about 65%, 70%, 75%, 80%, 85%, 90%, 95%, 98% or 99% sequence identity, to SEQ ID NO:31. In some embodiments, the nucleic acid encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:25. In some embodiments, the nucleic acid encoding mammary associated serum amyloid A3 (MAA) comprises a polynucleotide having at least about 60% sequence identity, e.g., at least about 65%, 70%, 75%, 80%, 85%, 90%, 95%, 98% or 99% sequence identity, to SEQ ID NO:18. In some embodiments, one or more nucleic acids encoding the one or more mammalian polypeptides selected from osteopontin, mammary associated serum amyloid A3 (MAA), lactoperoxidase, alpha-lactalbumin, lysozyme, soluble CD14, lingual antimicrobial peptide (LAP), cathelicidin-1, and lactadherin is integrated into the nuclear genome of the cell. In some embodiments, the one or more mammalian polypeptides are glycosylated. In some embodiments, the one or more mammalian polypeptides comprise an amino acid sequence that promotes retention in the endoplasmic reticulum. In some embodiments, the one or more mammalian polypeptides comprise an amino acid sequence that promotes secretion from the cell. In some embodiments, the one or more mammalian polypeptides comprise an amino acid sequence that promotes retention on the plasma membrane of a cell. In some embodiments, the one or more mammalian polypeptides comprise an amino acid sequence that promotes protein accumulation. In some embodiments, the cell is intact. In some embodiments, the cell is freeze-dried. In varying embodiments, the one or more colostrum/milk polypeptides are not purified or isolated from the cell.

In another aspect, provided is a photosynthetic organism comprising one or more polynucleotides encoding one or more mammalian colostrum or milk proteins is selected from the group consisting of soluble CD14 (sCD14), lactadherin, lactoperoxidase, milk lysozyme, osteopontin, cathelicidin-1, lingual antimicrobial peptide and alpha-lactalbumin. In varying embodiments, the photosynthetic organism is a non-vascular photosynthetic eukaryotic organism. In varying embodiments, the photosynthetic organism is a photosynthetic unicellular organism. In varying embodiments, the photosynthetic organism is a cyanobacteria. In some embodiments, the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae). In some embodiments, the photosynthetic organism is selected from the group consisting of *Chlamydomonas reinhardtii, Dunaliella salina, Haematococcus pluvialis, Chlorella vulgaris, Acutodesmus obliquus*, and *Scenedesmus dimorphus*. In some embodiments, the organism is a Chlorophyta (green algae). In some embodiments, the green alga is selected from the group consisting of *Chlamydomonas, Dunaliella, Haematococcus, Chlorella*, and Scenedesmaceae. In some embodiments, the *Chlamydomonas* is a *Chlamydomonas reinhardtii*. In varying embodiments, the green algae can be a *Chlorophycean*, a *Chlamydomonas, C. reinhardtii, C. reinhardtii* 137c, or a psbA deficient *C. reinhardtii* strain. In varying embodiments, the photosynthetic organism is a higher plant selected from Brassicaceae, Solanaceae, Phaseoleae, *Zea* and Oryzeae. In some embodiments, the cell comprises at least two (e.g., at least 3, 4, 5, 6, 7, 8, 9 or 10) polynucleotides encoding at least two mammalian milk or colostrum polypeptides. In some embodiments, the at least two mammalian milk or colostrum polypeptides comprise osteopontin and mammary associated serum amyloid A3 (MAA). In some embodiments, i) the polynucleotide encoding mammary associated serum amyloid A3 (MAA) is integrated into the nuclear genome, and the expressed protein is targeted to the cytoplasm; and ii) the polynucleotide encoding osteopontin is integrated into the nuclear genome, and the expressed protein is targeted to the endoplasmic reticulum; iii) the polynucleotide encoding osteopontin is integrated into the nuclear genome, and the expressed protein is targeted to a plastid (e.g., chloroplast, leucoplast, amyloplast, etc.); or iv) the polynucleotide encoding osteopontin is integrated into a plastid genome. In some embodiments, the at least two mammalian milk or colostrum polypeptides comprise lysozyme and mammary associated serum amyloid A3 (MAA). In some embodiments, the one or more mammalian polypeptides further comprises one or more mammalian milk or colostrum polypeptides selected from immunoglobulins (e.g., IgG1, IgG2, IgA, IgM, IgD), lactoferrin, mammary associated serum amyloid A3 (MAA), proline rich polypeptide (PRP), growth factors (e.g., transforming growth factor (TGF)-β1, TGF-β2, insulin-like growth factor 1 (somatomedin C) (IGF-1), IGF-2, epidermal growth factor, heparin-binding epidermal growth factor-like growth factor, betacellulin), cytokines (e.g., IL-6, IL-1β, IL 1ra) serum albumin, glycomacropeptide, casein proteins (e.g., β-casein, κ-casein, αs1 casein, αs2-casein and γ-casein), enzymes (e.g., superoxide dismutase, lactoperoxidase, alkaline phosphatase, platelet-activating factor-acetylhydroxylase, lysozyme), 14-3-3 protein zeta chain, 5-oxoprolinase (ATP-hydrolyzing), actin, cytoplasmic 1 (beta-actin), adipose differentiation-related protein, albumin (precursor), aldehyde dehydrogenase (NAD) 2 precursor, ankyrin 3, node of Ranvier (ankyrin G), annexin 1, annexin A2, apolipoprotein A-I, apolipoprotein B, ARP3 (actin-related protein 3, yeast) homolog, ATP synthase, H+ transporting, mitochondrial, F1 complex, alpha subunit, beta-2-microglobulin precursor (lactollin); butyrophilin, subfamily 1, member A1; capping protein (actin filament); muscle Z-line, alpha 1; casein kinase 1, alpha 1; coronin, actin binding protein, 1A; CD36 antigen [collagen type I receptor, thrombospondin receptor]; Chitinase-like protein 1 (CLP-1); DEAD (Asp-Glu-Ala-Asp) box (SEQ ID NO: 40) polypeptide 54; deleted in malignant brain tumors 1; diacylglycerol kinase kappa; endoplasmin precursor (GRP94/GP96); enolase 1; eukaryotic translation initiation factor 4, gamma 2; fatty acid binding protein, heart-type (MDGI); fetuin; fibrinogen alpha chain; fibrinogen beta chain precursor; fibrinogen gamma-B chain precursor; gene model 440, (NCBI); glucose regulated protein 58 kD; glutamate receptor, ionotropic, delta 1; glutathione S-transferase, mu 1; glyceraldehyde-3-phosphate; dehydrogenase (GAPDH); glycerol-3-phosphate dehydrogenase 2; glycoprotein antigen MGP57/53 (Lactadherin/bP47 protein); glycosylation-dependent cell adhesion molecule 1 (lactophorin/PP3); guanine nucleotide binding protein, beta 2; H3 histone, family 3A; heat shock 70 kDa protein 8; heat shock 70 kD protein 5 (glucose-regulated protein); heat shock protein 27; heat shock protein 70 kDa protein 1A; histone 2, H2ab; zinc finger protein 668; hypothetical/unnamed protein L0051063; IRTA2; isocitrate dehydrogenase 1 (NADP+), soluble; keratin 9; keratin complex 2, basic, gene 6a; keratin, type I cytoskeletal 10; and KIAA1586 protein. In varying embodiments, the one or more mammalian polypeptides are bioactive. In some embodiments, one or more polynucleotides encoding the one or more mammalian polypeptides is integrated into the chloroplast genome of the organism. In some embodiments, the one or more polynucleotides encoding the one or more mammalian polypeptides is operably linked to a promoter that promotes expression in the chloroplast. In some embodiments, the one or more mammalian polypeptides are retained or sequestered in the chloroplast of the organism. In some embodiments, one or more polynucleotides encoding the one or more mammalian polypeptides is integrated into the nuclear genome of the organism. In some embodiments, the one or more mammalian polypeptides are human milk or colostrum polypeptides. In some embodiments, the one or more mammalian polypeptides are bovine milk or colostrum polypeptides. In some embodiments, the polynucleotide encoding lysozyme comprises a polynucleotide having at least about 60% sequence identity, e.g., at least about 65%, 70%, 75%, 80%, 85%, 90%, 95%, 98% or 99% sequence identity, to SEQ ID NO:27. In some embodiments, the nucleic acid encoding soluble CD14 comprises a polynucleotide having at least about 60% sequence identity, e.g., at least about 65%, 70%, 75%, 80%, 85%, 90%, 95%, 98% or 99% sequence identity, to SEQ ID NO:33. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:23. In some embodiments, the nucleic acid encoding alpha-lactalbumin comprises a polynucleotide having at least about 60% sequence identity, e.g., at least about 65%, 70%, 75%, 80%, 85%, 90%, 95%, 98% or 99% sequence identity, to SEQ ID NO:29. In some embodiments, the nucleic acid encoding lingual antimicrobial peptide comprises a polynucleotide having at least about 60% sequence identity, e.g., at least about 65%, 70%, 75%, 80%, 85%, 90%, 95%, 98% or 99% sequence identity, to SEQ ID NO:31. In some embodiments, the nucleic acid encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:25. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:21. In some embodiments, the nucleic acid encoding lactoperoxidase comprises a polynucleotide having at least about 60% sequence identity, e.g., at least about 65%, 70%, 75%, 80%, 85%, 90%, 95%, 98% or 99% sequence identity, to SEQ ID NO:39. In some embodiments, the nucleic acid encoding mammary associated serum amyloid A3 (MAA) comprises a polynucleotide having at least about 60% sequence identity, e.g., at least about 65%, 70%, 75%, 80%, 85%, 90%, 95%, 98% or 99% sequence identity, to SEQ ID NO:18. In some embodiments, one or more nucleic acids encoding the one or more mammalian polypeptides selected from lysozyme, osteopontin, lactoperoxidase, lingual antimicrobial peptide (LAP), cathelicidin, alpha-lactalbumin, soluble CD14 and lactadherin is integrated into the nuclear genome of the organism. In some embodiments, the one or more mammalian polypeptides are glycosylated. In some embodiments, the one or more mammalian polypeptides comprise an amino acid sequence that promotes retention in the endoplasmic reticulum. In some embodiments, the one or more mammalian polypeptides comprise an amino acid sequence that promotes secretion from a cell. In some embodiments, the one or more mammalian polypeptides comprise an amino acid sequence that promotes retention on the plasma membrane of a cell. In some embodiments, the one or more mammalian polypeptides comprise an amino acid sequence that promotes protein accumulation. In some embodiments, the one or more mammalian polypeptides do not disrupt photosynthetic activity of said organism.

In another aspect, provided is a photosynthetic organism comprising one or more polynucleotides encoding one or more mammalian colostrum or milk proteins is selected from the group consisting of soluble CD14 (sCD14), lactadherin, lactoperoxidase, milk lysozyme, osteopontin, cathelicidin-1, lingual antimicrobial peptide and alpha-lactalbumin. In varying embodiments, the photosynthetic organism is a non-vascular photosynthetic eukaryotic organism. In varying embodiments, the photosynthetic organism is a photosynthetic unicellular organism. In varying embodiments, the photosynthetic organism is a cyanobacteria. In some embodiments, the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae). In some embodiments, the photosynthetic organism is selected from the group consisting of *Chlamydomonas reinhardtii, Dunaliella salina, Haematococcus pluvialis, Chlorella vulgaris, Acutodesmus obliquus,* and *Scenedesmus dimorphus*. In some embodiments, the organism is a Chlorophyta (green algae). In some embodiments, the green alga is selected from the group consisting of *Chlamydomonas, Dunaliella, Haematococcus, Chlorella,* and Scenedesmaceae. In some embodiments, the *Chlamydomonas* is a *Chlamydomonas reinhardtii*. In varying embodiments, the green algae can be a *Chlorophycean*, a *Chlamydomonas, C. reinhardtii, C. reinhardtii* 137c, or a psbA deficient *C. reinhardtii* strain. In varying embodiments, the photosynthetic organism is a higher plant selected from Brassicaceae, Solanaceae, Phaseoleae, *Zea* and Oryzeae. In some embodiments, the cell comprises at least two (e.g., at least 3, 4, 5, 6, 7, 8, 9 or 10) polynucleotides encoding at least two mammalian milk or colostrum polypeptides. In some embodiments, the at least two mammalian milk or colostrum polypeptides comprise osteopontin and mammary associated serum amyloid A3 (MAA). In some embodiments, i) the polynucleotide encoding mammary associated serum amyloid A3 (MAA) is integrated into the nuclear genome, and the expressed protein is targeted to the cytoplasm; and ii) the polynucleotide encoding osteopontin is integrated into the nuclear genome, and the expressed protein is targeted to the endoplasmic reticulum; iii) the polynucleotide encoding osteopontin is integrated into the nuclear genome, and the expressed protein is targeted to a plastid (e.g., chloroplast, leucoplast, amyloplast, etc.); or iv) the polynucleotide encoding osteopontin is integrated into a plastid genome. In some embodiments, the at least two mammalian milk or colostrum polypeptides comprise lysozyme and mammary associated serum amyloid A3 (MAA). In some embodiments, the one or more mammalian polypeptides further comprises one or more mammalian milk or colostrum polypeptides selected from immunoglobulins (e.g., IgG1, IgG2, IgA, IgM, IgD), lactoferrin, mammary associated serum amyloid A3 (MAA), proline rich polypeptide (PRP), growth factors (e.g., transforming growth factor (TGF)-β1, TGF-β2, insulin-like growth factor 1 (somatomedin C) (IGF-1), IGF-2, epidermal growth factor, heparin-binding epidermal growth factor-like growth factor, betacellulin), cytokines (e.g., IL-6, IL-1β, IL 1ra) serum albumin, glycomacropeptide, casein proteins (e.g., β-casein, κ-casein, αs1 casein, αs2-casein and γ-casein), enzymes (e.g., superoxide dismutase, lactoperoxidase, alkaline phosphatase, platelet-activating factor-acetylhydroxylase, lysozyme), 14-3-3 protein zeta chain, 5-oxoprolinase (ATP-hydrolyzing), actin, cytoplasmic 1 (beta-actin), adipose differentiation-related protein, albumin (precursor), aldehyde dehydrogenase (NAD) 2 precursor, ankyrin 3, node of Ranvier (ankyrin G), annexin 1, annexin A2, apolipoprotein A-I, apolipoprotein B, ARP3 (actin-related protein 3, yeast) homolog, ATP synthase, H+ transporting, mitochondrial, F1 complex, alpha subunit, beta-2-microglobulin precursor (lactollin); butyrophilin, subfamily 1, member A1; capping protein (actin filament); muscle Z-line, alpha 1; casein kinase 1, alpha 1; coronin, actin binding protein, 1A; CD36 antigen [collagen type I receptor, thrombospondin receptor]; Chitinase-like protein 1 (CLP-1); DEAD (Asp-Glu-Ala-Asp) box polypeptide 54; deleted in malignant brain tumors 1; diacylglycerol kinase kappa; endoplasmin precursor (GRP94/GP96); enolase 1; eukaryotic translation initiation factor 4, gamma 2; fatty acid binding protein, heart-type (MDGI); fetuin; fibrinogen alpha chain; fibrinogen beta chain precursor; fibrinogen gamma-B chain precursor; gene model 440, (NCBI); glucose regulated protein 58 kD; glutamate receptor, ionotropic, delta 1; glutathione S-transferase, mu 1; glyceraldehyde-3-phosphate; dehydrogenase (GAPDH); glycerol-3-phosphate dehydrogenase 2; glycoprotein antigen MGP57/53 (Lactadherin/bP47 protein); glycosylation-dependent cell adhesion molecule 1 (lactophorin/PP3); guanine nucleotide binding protein, beta 2; H3 histone, family 3A; heat shock 70 kDa protein 8; heat shock 70 kD protein 5 (glucose-regulated protein); heat shock protein 27; heat shock protein 70 kDa protein 1A; histone 2, H2ab; zinc finger protein 668; hypothetical/unnamed protein LOC51063; IRTA2; isocitrate dehydrogenase 1 (NADP+), soluble; keratin 9; keratin complex 2, basic, gene 6a; keratin, type I cytoskeletal 10; and KIAA1586 protein. In varying embodiments, the one or more mammalian polypeptides are bioactive. In some embodiments, one or more polynucleotides encoding the one or more mammalian polypeptides is integrated into the chloroplast genome of the organism. In some embodiments, the one or more polynucleotides encoding the one or more mammalian polypeptides is operably linked to a promoter that promotes expression in the chloroplast. In some embodiments, the one or more mammalian polypeptides are retained or sequestered in the chloroplast of the organism. In some embodiments, one or more polynucleotides encoding the one or more mammalian polypeptides is integrated into the nuclear genome of the organism. In some embodiments, the one or more mammalian polypeptides are human milk or colostrum polypeptides. In some embodiments, the one or more mammalian polypeptides are bovine milk or colostrum polypeptides. In some embodiments, the polynucleotide encoding lysozyme comprises a polynucleotide having at least about 60% sequence identity, e.g., at least about 65%, 70%, 75%, 80%, 85%, 90%, 95%, 98% or 99% sequence identity, to SEQ ID NO:27. In some embodiments, the nucleic acid encoding soluble CD14 comprises a polynucleotide having at least about 60% sequence identity, e.g., at least about 65%, 70%, 75%, 80%, 85%, 90%, 95%, 98% or 99% sequence identity, to SEQ ID NO:33. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:23. In some embodiments, the nucleic acid encoding alpha-lactalbumin comprises a polynucleotide having at least about 60% sequence identity, e.g., at least about 65%, 70%, 75%, 80%, 85%, 90%, 95%, 98% or 99% sequence identity, to SEQ ID NO:29. In some embodiments, the nucleic acid encoding lingual antimicrobial peptide comprises a polynucleotide having at least about 60% sequence identity, e.g., at least about 65%, 70%, 75%, 80%, 85%, 90%, 95%, 98% or 99% sequence identity, to SEQ ID NO:31. In some embodiments, the nucleic acid encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:25. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:21. In some embodiments, the nucleic acid encoding lactoperoxidase comprises a polynucleotide having at least about 60% sequence identity, e.g., at least about 65%, 70%, 75%, 80%, 85%, 90%, 95%, 98% or 99% sequence identity, to SEQ ID NO:39. In some embodiments, the nucleic acid encoding mammary associated serum amyloid A3 (MAA) comprises a polynucleotide having at least about 60% sequence identity, e.g., at least about 65%, 70%, 75%, 80%, 85%, 90%, 95%, 98% or 99% sequence identity, to SEQ ID NO:18. In some embodiments, one or more nucleic acids encoding the one or more mammalian polypeptides selected from lysozyme, osteopontin, lactoperoxidase, lingual antimicrobial peptide (LAP), cathelicidin, alpha-lactalbumin, soluble CD14 and lactadherin is integrated into the nuclear genome of the organism. In some embodiments, the one or more mammalian polypeptides are glycosylated. In some embodiments, the one or more mammalian polypeptides comprise an amino acid sequence that promotes retention in the endoplasmic reticulum. In some embodiments, the one or more mammalian polypeptides comprise an amino acid sequence that promotes secretion from a cell. In some embodiments, the one or more mammalian polypeptides comprise an amino acid sequence that promotes retention on the plasma membrane of a cell. In some embodiments, the one or more mammalian polypeptides comprise an amino acid sequence that promotes protein accumulation. In some embodiments, the one or more mammalian polypeptides do not disrupt photosynthetic activity of said organism.

Further provided are polynucleotides, e.g., for the expression of mammalian milk/colostrum proteins in the nucleus or nuclear genome of a photosynthetic organism. In some embodiments, the nucleic acid encoding lysozyme comprises a polynucleotide having at least about 60% sequence identity, e.g., at least about 65%, 70%, 75%, 80%, 85%, 90%, 95%, 98% or 99% sequence identity, to SEQ ID NO:27. In some embodiments, the nucleic acid encoding soluble CD14 comprises a polynucleotide having at least about 60% sequence identity, e.g., at least about 65%, 70%, 75%, 80%, 85%, 90%, 95%, 98% or 99% sequence identity, to SEQ ID NO:33. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:23. In some embodiments, the nucleic acid encoding alpha-lactalbumin comprises a polynucleotide having at least about 60% sequence identity, e.g., at least about 65%, 70%, 75%, 80%, 85%, 90%, 95%, 98% or 99% sequence identity, to SEQ ID NO:29. In some embodiments, the nucleic acid encoding lingual antimicrobial peptide comprises a polynucleotide having at least about 60% sequence identity, e.g., at least about 65%, 70%, 75%, 80%, 85%, 90%, 95%, 98% or 99% sequence identity, to SEQ ID NO:31. In some embodiments, the nucleic acid encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:25. In some embodiments, the nucleic acid encoding lactoperoxidase comprises a polynucleotide having at least about 60% sequence identity, e.g., at least about 65%, 70%, 75%, 80%, 85%, 90%, 95%, 98% or 99% sequence identity, to SEQ ID NO:39. In some embodiments, the nucleic acid encoding mammary associated serum amyloid A3 (MAA) comprises a polynucleotide having at least about 60% sequence identity, e.g., at least about 65%, 70%, 75%, 80%, 85%, 90%, 95%, 98% or 99% sequence identity, to SEQ ID NO:18. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:21.

Further provided are methods for producing one or more mammalian colostrum or milk proteins, comprising culturing a cell or an organism as described above and herein. In some embodiments, the cell or the organism is grown in the absence of light and in the presence of an organic carbon source.

Further provided are compositions edible by a mammal comprising one or more populations of cells or one or more populations of organisms as described above and herein. In some embodiments, the composition is selected from a liquid or beverage (e.g., infant formula), a food, a feed, a food supplement, a nutraceutical (e.g., a pill). In some embodiments, the composition is selected from the group consisting of a compressed algal cake, an algal paste and an algal powder. In varying embodiments, the compositions are lyophilized or spray dried. In some embodiments, the photosynthetic organisms (e.g., algae) are lyophilized or spray-dried prior to the addition to an edible composition, e.g., a food, beverage or tablet consumable by a mammal, e.g., a human, a canine, a feline. In some embodiments, the photosynthetic organisms (e.g., algae) are formulated into a wet paste prior to the addition to an edible composition, e.g., a food, beverage or tablet consumable by a mammal, e.g., a human, a canine, a feline. In some embodiments, the photosynthetic organisms (e.g., algae) are formulated into a powder to be sprinkled onto or into an edible composition, e.g., a food, beverage or tablet consumable by a mammal, e.g., a human, a canine, a feline. In some embodiments the photosynthetic organisms (e.g., algae) are blended or mixed into an edible composition, e.g., a food, beverage or tablet consumable by a mammal, e.g., a human, a canine, a feline.

Further provided are methods of producing a such compositions edible by a mammal. In varying embodiments, the methods comprise combining two or more populations of cells or two or more populations of organisms as described above and herein.

Definitions

The term "non-vascular photosynthetic eukaryotic organism" refers to an organism of the kingdom Planta that does not have xylem or phloem. These include all species of algae and mosses as well as other photosynthetic organisms like liverworts.

The term "bioactive" refers to detectable biological activity of a polypeptide, using any assay known in the art to detect the biological activity. The biological activities of the polypeptides described herein and assays for detecting their biological activity are known in the art. For example, the bioactivity of osteopontin can be measured by the ability of osteopontin to adhere to human embryonic 293 cells when in the presence of the divalent cations, $Mg^{2+}$ or $Mn^{2+}$ but not $Ca^{2+}$ (Hu, et al, *J Biol Chem*. (1995) 270(17):9917-25). The bioactivity of mammary-associated serum amyloid (MAA) protein can be determined by the purified proteins ability to stimulate muc3 production from HT29 cells (Manuell et al., *Plant Biotechnol J*. (2007) 5(3):402-12). The bioactivity of lactadherin can be determined by its ability to bind to phosphatidylserine (Otzen, et al., *Biochim Biophys Acta*. (2012) 1818(4):1019-27). Cathelicidin-1 activity can be determined using an antimicrobial assay and measuring luminescence. See, e.g., Sue, et al. *Infect Immun*. 2000 68(5) 2748-2755.

The terms "identical" or percent "identity," and variants thereof in the context of two or more polynucleotide or two or more amino acid sequences, refer to two or more sequences or subsequences that are the same. Sequences are "substantially identical" if they have a specified percentage of nucleic acid residues or amino acid residues that are the same (i.e., at least 60% identity, optionally at least 65%, 70%, 75%, 80%, 85%, 90%, 95%, 96%, 97%, 98%, or 99% identity to a reference sequence (e.g., SEQ ID NOs. 1-39) over a specified region (or the whole reference sequence when not specified)), when compared and aligned for maximum correspondence over a comparison window, or designated region as measured using any sequence comparison algorithm known in the art (GAP, BESTFIT, BLAST, Align, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990) set to default settings, or by manual alignment and visual inspection (see, e.g., Ausubel et al., Current Protocols in Molecular Biology (1995-2014). Provided are polynucleotides improved for expression in photosynthetic (e.g., algal) host cells that are substantially identical to the polynucleotides of SEQ ID NOs: 1, 3, 4, 6, 8, 10, 12, 14, 16, 18, 20, 21, 23, 25, 27, 29, 31, 33, 37 and 39. Optionally, the identity exists over a region that is at least about 50, 100, 150, 200, 250, 300 amino acids in length, or more preferably over a region that is 100, 200, 300, 400, 500, 600, 800, 1000, or more, nucleic acids in length, or over the full-length of the sequence.

The term "conservatively modified variations" refers to individual substitutions, deletions or additions which alter, add or delete a single amino acid or a small percentage of amino acids (typically less than 5%, more typically less than 1%) in an encoded sequence, where the alterations result in the substitution of an amino acid with a chemically similar amino acid; and the alterations, deletions or additions do not alter the structure, function and/or immunogenicity of the sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

BRIEF DESCRIPTION OF THE DRAWINGS

FIG. 2 illustrates a polynucleotide sequence (SEQ ID NO: 57) with altered codons for improved expression of milk lysozyme from the nuclear genome and the corresponding amino acid sequence (SEQ ID NO: 5).

FIG. 3A-B illustrate a polynucleotide sequence (SEQ ID NO: 58) with altered codons for improved expression of lactadherin from the nuclear genome and the corresponding amino acid sequence (SEQ ID NO: 7).

FIG. 4 illustrates a polynucleotide sequence (SEQ ID NO: 59) with altered codons for improved expression of osteopontin from the nuclear genome and the corresponding amino acid sequence (SEQ ID NO: 9).

FIG. 5 illustrates a polynucleotide sequence (SEQ ID NO: 60) with altered codons for improved expression of alpha-lactalbumin from the nuclear genome and the corresponding amino acid sequence (SEQ ID NO: 11).

FIG. 6 illustrates a polynucleotide sequence (SEQ ID NO: 61) with altered codons for improved expression of cathelicidin-1 from the nuclear genome and the corresponding amino acid sequence (SEQ ID NO: 13).

FIG. 7 illustrates a polynucleotide sequence (SEQ ID NO: 62) with altered codons for improved expression of lingual antimicrobial peptide (LAP) from the nuclear genome and the corresponding amino acid sequence (SEQ ID NO: 15).

FIG. 8 illustrates a polynucleotide sequence (SEQ ID NO: 63) with altered codons for improved expression of soluble CD14 from the nuclear genome and the corresponding amino acid sequence (SEQ ID NO: 17).

FIGS. 9A-B illustrate a polynucleotide sequence (SEQ ID NO: 64) with altered codons for improved expression of lactoperoxidase from the nuclear genome and the corresponding amino acid sequence (SEQ ID NO: 38).

FIG. 10 illustrates a polynucleotide sequence (SEQ ID NO: 65) with altered codons for improved expression of mammary associated serum amyloid A3 (MAA) from the nuclear genome and the corresponding amino acid sequence (SEQ ID NO: 19).

FIG. 10 illustrates a polynucleotide sequence with altered codons for improved expression of mammary associated serum amyloid A3 (MAA) from the nuclear genome and the corresponding amino acid sequence.

FIGS. 11A-F illustrate protein expression in algae of mammary-associated serum amyloid A3 (MAA), soluble CD14 (sCD14), alpha-lactalbumin (aLA), lactadherin (LAD), lysozyme, osteopontin (OPN), lactoperoxidase (LPO), cathelicidin-1 (CathL) and lingual antimicrobial peptide (LAP). (A) Immunoblot analysis of 30 µg of total protein isolated from cc1690 (WT) and a transgenic line transformed with ble2A-MAA. B Immunoblot analysis of 50 µg of total soluble protein fractions from strains expressing four ER targeted colostrum/milk proteins. The asterisks (*) marks a nonspecific, cross-reacting band detected with the anti-FLAG antibody. Molecular weight markers (kDa) are indicated. C-F. Immunoprecipitations of (C) osteopontin (OPN), (D) lingual antimicrobial peptide (LAP), (E) cathelicidin-1 (CathL-1), and (F) alpha-lactalbumin (a-LA). Protein markers (M) are shown for each immunoprecipitation. Blots were probed with anti-FLAG antibody.

FIGS. 14A-D illustrate that algal-expressed milk proteins are bioactive. Affinity purified milk proteins show in vitro bioactivity. A) A modified sandwich ELISA was performed to demonstrate sCD14 binds LPS. sCD14, mCherry, or buffer (PBS) was bound to microtiter plates. Biotinylated LPS or buffer alone, in the presence of bovine serum, was incubated with the immobilized proteins, washed, and detected using streptavidin-HRP. B) A dilution series of purified LPO or mCherry was added to a microtiter plate. One step Ultra TMB peroxidase substrate was added to illustrate LPO has functional peroxidase activity. C) Purified LAD or mCherry was added to a phosphatidylserine (PS)-coated microtiter plate. A modified ELISA protocol was followed to reveal algal-expressed LAD binds PS in a concentration dependent fashion. D) *Micrococcus lysodiekitcus* Gram-positive bacteria was incubated with affinity purified algal-expressed lysozyme or commercial chicken egg white lysozyme (CEWL). Cell lysis was measured as a decrease in absorbance at 450 nm over time. Lysozyme activity unit (U) was defined as a drop in absorbance of 0.001 per minute at pH 6.2. Units were calculated by averaging the change in absorbance over the first four minutes where the decrease in absorbance is most linear. Units were normalized to the amount of protein added to give a U/mg readout. The date shows algal-expressed LysC has comparable activity (U/mg) to commercially produced CEWL. A-D. Data points represent averages of triplicate measurements with error bars representing ±one standard deviation (SD).

DETAILED DESCRIPTION

1. Introduction

Figure 12:
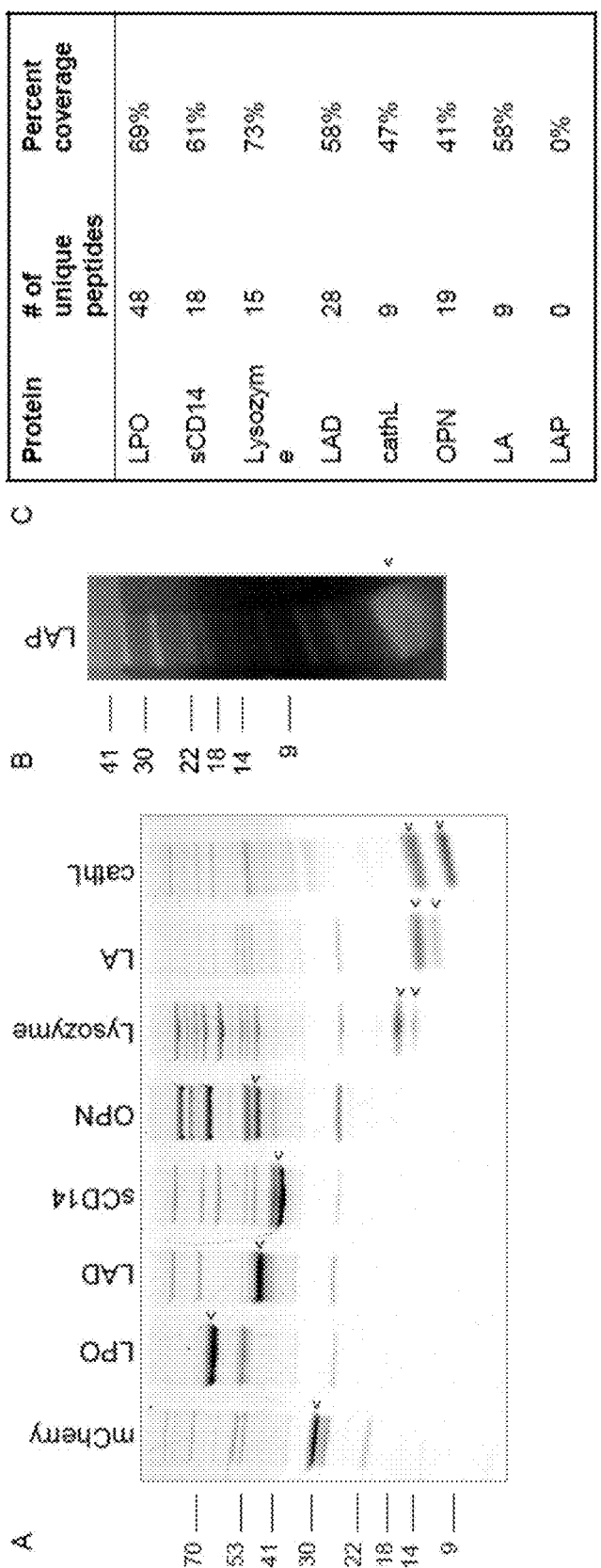
FIGS. 12A-C illustrate protein purification and validation by mass spectrometry. A) Coomassie stained SDS-PAGE gel of the purified milk/colostrum proteins expressed in *C. reinhardtii*. B) Purified algal-expressed lingual antimicrobial peptide (LAP) was detected with Oriole Fluorescence SDS-PAGE gel stain. Arrowhead indicates purified protein. Molecular weight markers (kDa) are indicated. C) Purified proteins were digested with trypsin and validated by mass spectrometry. Number of unique peptides and percent coverage are given for each algal-expressed protein.
Figure 13:
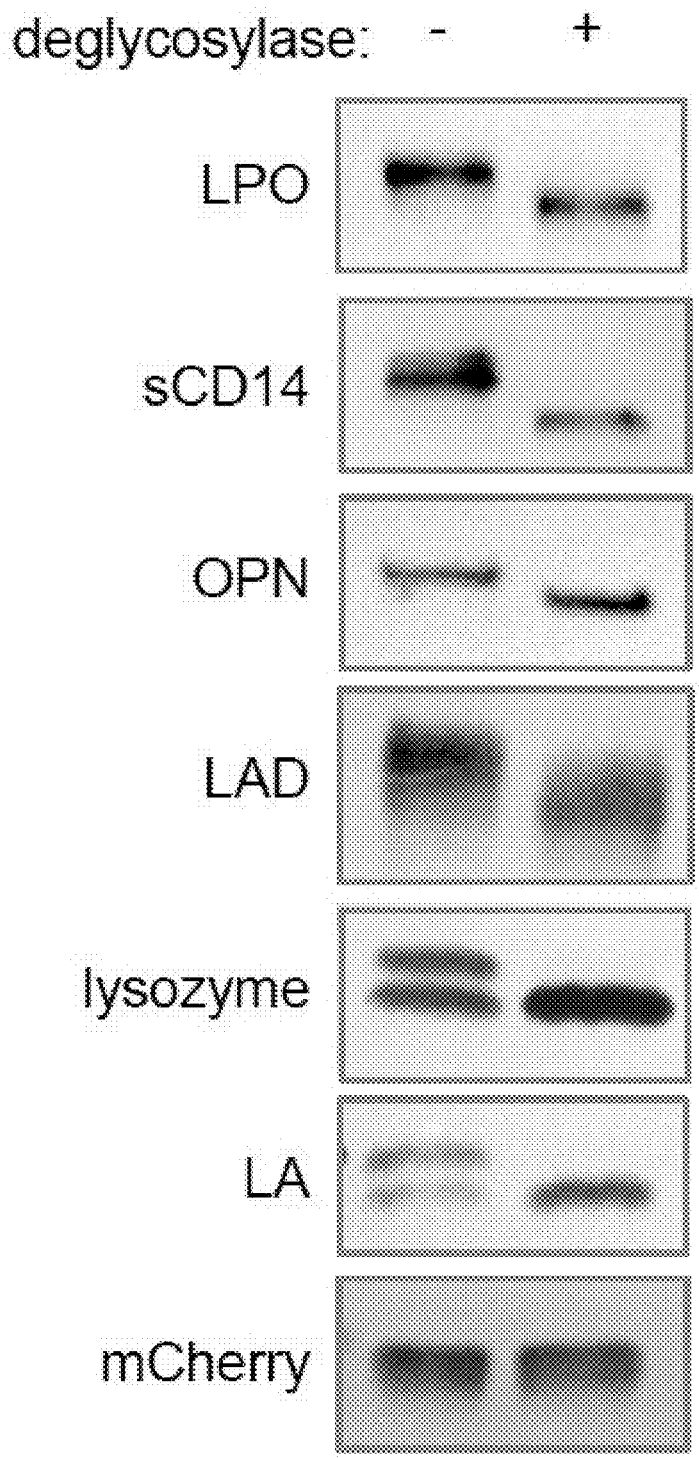
FIG. 13 illustrates that milk glycoproteins are glycosylated in *C. reinhardtii*. Algal-expressed purified milk proteins were treated with a deglycosylase cocktail (+) and analyzed by immunoblotting with anti-FLAG-AP. A change in electrophoretic mobility on SDS-PAGE compared to the untreated control (–) indicates the removable of glycans. ER-targeted mCherry—a naturally aglycosylated protein—is shown as a negative control.

Described herein are compositions and processes to produce bioactive colostrum and/or milk proteins for health and nutrition purposes using engineering of the nuclear genome of photosynthetic organisms (e.g., algae) as both a production and delivery vehicle. The organisms and processes described herein provide an alternative system and organisms for lower cost and large-scale production of singular and/or tailored mixtures/combinations of orally active colostrum and milk bioactives in an orally available form (e.g., edible algae). Two or more colostrum/milk polypeptides can be expressed in the same organism, e.g., from the nuclear genome, from the chloroplast genome, or from both the nuclear and chloroplast genome.

Genes encoding bioactive colostrum/milk proteins have altered codons for expression from the nuclear or chloroplast genomes of edible photosynthetic organisms (e.g., for example, higher plants, algae, microalgae, including Chlorophyta, e.g., *Chlamydomonas reinhardtii*) or from the genome or plasmid of cyanobacteria). Illustrative colostrum/milk proteins include without limitation soluble CD14 (sCD14), lactadherin, lactoperoxidase, milk lysozyme, osteopontin, cathelicidin-1, lingual antimicrobial peptide (LAP), alpha-lactalbumin, and mammary associated serum amyloid A3 (MAA) (FIG. 1). The colostrum/milk genes can be integrated into and expressed from nuclear or chloroplast genomes of photosynthetic organisms. Expression and bioactivity can be confirmed using methods known in the art.

Production and/or delivery of colostrum/milk polypeptides in edible photosynthetic organisms finds use, e.g., in human and mammal health and nutrition; prophylaxis and treatment for enteric infection; prophylaxis and/or treatment of gastric, intestinal, or bowel inflammation; improving nutrient uptake efficiency; improving bone strength; food preservation and processing; cosmetics preservation; odor treatment and neutralization; oral hygiene; acne treatment; and topical and oral antibacterial, antiviral, and/or antimicrobial therapy.

2. Colostrum/Milk Polynucleotides and Polypeptides

Photosynthetic eukaryotic organisms have one or more polynucleotides encoding one or more mammalian colostrum/milk polypeptides are integrated into the nuclear and/or chloroplast genome. In varying embodiments, 2, 3, 4, 5, 6, 7, 8, 9, 10, or more, polynucleotides encoding mammalian colostrum/milk polypeptides are independently integrated into the nuclear and/or chloroplast genome of a photosynthetic organism.

Illustrative mammalian colostrum/milk polypeptides for expression in photosynthetic organisms (e.g. chlorophyta, e.g., *Chlamydomonas*), and the nuclei and cells thereof, are described above and herein. See, e.g., Smolenski, et al., *J Proteome Res.* 2007 January; 6(1):207-15; Boudry and Thewis, Bulletin UASVM Animal Science and Biotechnologies (2009) 66 (1-2); Chatterton, et al., *Intl Journal of Biochemistry & Cell Biology* 45 (2013) 1730-1747; Lis, et al., *Postepy Hig Med Dosw* (2013) 67: 529-547; and Artym, et al., *Postepy Hig Med Dosw* (2013) 67: 800-816. In varying embodiments, the one or more colostrum/milk polypeptides are whey proteins (e.g., alpha-lactalbumim, beta-lactoglobulin, osteopontin, lactoferrin and/or immunoglobulins). The expressed mammalian colostrum/milk polypeptides, and chloroplasts, cells and photosynthetic organisms comprising the polypeptides, can be used as and in compositions edible by a mammal (e.g., having both nutritional and therapeutic value).

In varying embodiments, the milk/colostrum polypeptides are human, non-human primate, bovinae (e.g., cow, bison), ovine, caprine, camelid, human, canine, feline, equine, marsupial, or from any other mammal of interest. The polynucleotide and polypeptide sequences of mammalian homologs of milk/colostrum polypeptides are known in the art. For example, the GenBank Ref. Seq. Accession Nos. for osteopontin polypeptide homologs are NP_000573.1 (human), XP_003434072.1 (canine), XP_003985233.1 (feline), and NP_776612.1 (bovine). For example, mammalian milk/colostrum proteins (e.g., osteopontin, e.g., from a human, canine, or feline) can be produced in a photosynthetic organism (e.g., algae) and subsequently lyophilized and sprinkled onto a food or into a beverage consumable by the mammal (e.g., human, canine, or feline, respectively). In another example, mammalian milk/colostrum proteins (e.g., from a human, canine, feline or equine) produced in a photosynthetic organism (e.g., algae) can be formulated into a wet paste and delivered orally to the mammal (e.g., to the human, canine, feline or equine), e.g., using a syringe. In another example, lyophilized, freeze-dried or spray-dried photosynthetic organisms (e.g., algae) comprising mammalian milk/colostrum polypeptides can be resuspended in water for oral delivery to the mammal (e.g., to the human, canine, feline or equine), e.g., using a syringe. In another example, lyophilized, freeze-dried, spray-dried or powdered photosynthetic organisms (e.g., algae) comprising mammalian milk/colostrum polypeptides can be sprayed onto or mixed or blended into a food, feed or beverage edible by a mammal (e.g., to the human, canine, feline or equine), e.g., sprayed onto kibble for a non-human mammal.

Polynucleotides encoding one or more milk/colostrum polypeptides, or immunogenic fragments thereof, can be altered for improved expression in a photosynthetic (e.g., algal) host cells. For example, codons in the wild-type polynucleotides encoding one or more milk/colostrum polypeptides rarely used by the photosynthetic (e.g., algal) host cell can be replaced with a codon coding for the same or a similar amino acid residue that is more commonly used by the photosynthetic (e.g., algal) host cell (i.e., employing algal chloroplast codon bias), thereby allowing for more efficient expression of the milk/colostrum polypeptide and higher yields of the expressed milk/colostrum polypeptide in the photosynthetic host, in comparison to expression of the milk/colostrum polypeptide from the wild-type polynucleotide. Methods for altering polynucleotides for improved expression in a photosynthetic (e.g., algal) host cell, particularly in a *Chlamydomonas reinhardtii* host cell, are known in the art and described in, e.g., Franklin et at (2002) *Plant J* 30:733-744; Fletcher, et al., *Adv Exp Med Biol.* (2007) 616:90-8; Heitzer, et al., *Adv Exp Med Biol.* (2007) 616:46-53; Rasala and Mayfield, *Bioeng Bugs.* (2011) 2(1): 50-4; Rasala, et al, *Plant Biotechnol J.* (2010) 8(6):719-33; Wu, et al., *Bioresour Technol.* (2011) 102(3):2610-6; Morton, *J Mol Evol.* (1993) 37(3):273-80; Morton, *J Mol Evol.* (1996) 43(1):28-31; and Morton, *J Mol Evol.* (1998) 46(4): 449-59.

In various embodiments, polynucleotide sequences encoding milk/colostrum polypeptides can be improved for expression in photosynthetic organisms (e.g., algae) by changing codons that are not common in the algae host cell (e.g., used less than ~20% of the time). A codon usage database of use is found at kazusa.or.jp/codon/. For improved expression of polynucleotide sequences encoding milk/colostrum polypeptides in *C. reinhardtii* host cells, codons rare or not common to the nuclear genome of *C. reinhardtii* in the native milk/colostrum nucleic acid sequences are reduced or eliminated. A representative codon table summarizing codon usage in the *C. reinhardtii* chloroplast is found on the internet at kazusa.or.jp/codon/cgi-bin/showcodon.cgi?species=3055.chloroplast. In various embodiments, preferred or more common codons for amino acid residues in *C. reinhardtii* are as follows:

| Amino Acid Residue | Preferred codons for improved expression in algae |
|---|---|
| Ala | GCG, GCC |
| Arg | CGC |
| Asn | AAC |
| Asp | GAC |
| Cys | TGC |
| Gln | CAG |
| Glu | GAG |
| Gly | GGC |
| Ile | ATC |
| His | CAC |
| Leu | CTG |
| Lys | AAG |
| Met | ATG |
| Phe | TTC |

-continued

| Amino Acid Residue | Preferred codons for improved expression in algae |
|---|---|
| Pro | CCC, CCG |
| Ser | TCC, TCG |
| Thr | ACC |
| Trp | TGG |
| Tyr | TAC |
| Val | GTG |
| STOP | TAA |

In varying embodiments, the polypeptides are glycosylated. In varying embodiments for expression from the nuclear genome, the polynucleotide sequences encoding the mammalian milk/colostrum polypeptides can further encode an endoplasmic reticulum (ER) retention sequence. Illustrative ER retention sequences are known in the art and include without limitation FEHDEL (SEQ ID NO: 41), KDEL (SEQ ID NO: 42), HDEL (SEQ ID NO: 43) and RDEL (SEQ ID NO: 44).

In varying embodiments, the polynucleotide sequences encoding the mammalian milk/colostrum polypeptides can further encode an amino acid sequence that promotes secretion from the cell (e.g., signal peptides). Illustrative amino acid sequences that promote secretion from the cell include without limitation the secretion signal peptides from *Chlamydomonas reinhardtii* ars1 (MHARKMGALAVLAVAC-LAAVASVAHAADTK) (SEQ ID NO: 45), ars2 (MGALA-VFAVACLAAVASVAHAAD) (SEQ ID NO: 46) and the ER insertion signal from *C. reinhardtii* Bip1 (MAQWKAAV-LLLALACASYGFGVWAEEEKLGTVIG) (SEQ ID NO: 47). In some embodiments, the one or more mammalian polypeptides comprise an amino acid sequence that promotes retention on the surface of a cell. Illustrative amino acid sequences that promote retention on the surface (e.g., plasma membrane) of a cell include without limitation a glycosylphosphatidylinositol anchor (GPI-anchor), protein fusions to full-length or domains of cell wall components including hydroxyproline-rich glycoproteins, protein fusions to full-length or domains of agglutinins, or protein fusions to full-length or domains of outer plasma membrane proteins. In varying embodiments, the polynucleotide sequences encoding the mammalian milk/colostrum polypeptides can further encode a sequence that promotes protein accumulation. Protein accumulation amino acid sequences are known in the art and find use. Illustrative protein accumulation amino acid sequences include:
gamma zein (Zera) (SEQ ID NO:35):
MRVLLVALALLALAASATSTHTSGGCGCQPPPPVHLPPPVHLPPPVHLPPPVHLPPPVHLPPPVHLPPPVHLPPPVHVPPPVHLPPPPCHYPTQPPRPQPHPQPHPCPCQQPHPSPCQ
hydrophobin (HBN1) (SEQ ID NO:36):
GSSNGNGNVCPPGLFSNPQCCATQVLGLIGLDCKVP-SQNVYDGTDFRNVCAKTGAQPLCCVA PVAGQALLC-QTAVGA In varying embodiments, the polynucleotide sequences encoding the mammalian milk/colostrum polypeptides can further encode an amino acid sequence that promotes secretion from the cell (e.g., signal peptides). Illustrative amino acid sequences that promote secretion from the cell include without limitation the secretion signal peptides from *Chlamydomonas reinhardtii* ars1 (MHARKMGALAVLAVAC-LAAVASVAHAADTK), ars2 (MGALAVFAVACLAAVAS-VAHAAD) and the ER insertion signal from *C. reinhardtii* Bip1 (MAQWKAAVLLLALACASYGFGVWAEEEKL-GTVIG). In some embodiments, the one or more mammalian polypeptides comprise an amino acid sequence that promotes retention on the surface of a cell. Illustrative amino acid sequences that promote retention on the surface (e.g., plasma membrane) of a cell include without limitation a glycosylphosphatidylinositol anchor (GPI-anchor), protein fusions to full-length or domains of cell wall components including hydroxyproline-rich glycoproteins, protein fusions to full-length or domains of agglutinins, or protein fusions to full-length or domains of outer plasma membrane proteins. In varying embodiments, the polynucleotide sequences encoding the mammalian milk/colostrum polypeptides can further encode a sequence that promotes protein accumulation. Protein accumulation amino acid sequences are known in the art and find use. Illustrative protein accumulation amino acid sequences include:

```
gamma zein (Zera)(SEQ ID NO: 35):
MRVLLVALALLLALAASATSTHTSGGCGCQPPPPVHLPPPVHLPPPVHLPP

PVHLPPPVHLPPPVHLPPPVHVPPPVHLPPPPCHYPTQPPRPQPHPQPHP

CPCQQPHPSPCQ hydrophobin (HBN1)(SEQ ID NO: 36):
GSSNGNGNVCPPGLFSNPQCCATQVLGLIGLDCKVPSQNVYDGTDFRNVC

AKTGAQPLCCVAPVAGQALLCQTAVGA
```

In varying embodiments, the chloroplasts of photosynthetic (e.g., algal) host cells are transformed, e.g., by homologous recombination techniques, to contain and stably express one or more polynucleotides encoding one or more milk/colostrum polypeptides, as described herein, integrated into the chloroplast genome.

Transformation of the chloroplasts of photosynthetic (e.g., algal) host cells can be carried out according to techniques well known to those persons skilled in the art. Examples of such techniques include without limitation electroporation, particle bombardment, cytoplasmic or nuclear microinjection, gene gun. See, e.g., FIG. 2 of WO 2012/170125.

3. Photosynthetic Organisms

The colostrum/milk polypeptides can be integrated into and expressed from the chloroplast genome or the nuclear genome of a eukaryotic photosynthetic organism. The colostrum/milk polypeptides can be integrated into the genome or expressed from a plasmid of cyanobacteria. Photosynthetic organisms useful for the expression of colostrum/milk polypeptides include, without limitation, higher plants, algae (including microalgae), and cyanobacteria. In varying embodiments, the photosynthetic organism can be eukaryotic (e.g., higher plants and algae, including microalgae) or prokaryotic (e.g., cyanobacteria). Plants of interest include vascular plant (e.g., a *brassica* plant, corn, soybean, tobacco, etc), and non-vascular plants (e.g., algae, including microalgae, and mosses). Embodiments of photosynthetic organisms are described above and herein.

In varying embodiments, the chloroplast, nucleus, cell and/or organism is a microalgae. Illustrative and additional microalgae species of interest include without limitation, *Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia* hooglandii, Borodinella sp., Botryococcus braunii, Botryococcus sudeticus, Carteria, Chaetoceros gracilis, Chaetoceros muelleri, Chaetoceros muelleri subsalsum, Chaetoceros sp., Chlamydomonas sp., Chlamydomonas reinhardtii, Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca var. vacuolata, Chlorella glucotropha, Chlorella infusionum, Chlorella infusionum var. actophila, Chlorella infusionum var. auxenophila, Chlorella kessleri, Chlorella lobophora (strain SAG 37.88), Chlorella luteoviridis, Chlorella luteoviridis var. aureoviridis, Chlorella luteoviridis var. lutescens, Chlorella miniata, Chlorella minutissima, Chlorella mutabilis, Chlorella nocturna, Chlorella parva, Chlorella photophila, Chlorella pringsheimii, Chlorella protothecoides, Chlorella protothecoides var. acidicola, Chlorella regularis, Chlorella regularis var. minima, Chlorella regularis var. umbricata, Chlorella reisiglii, Chlorella saccharophila, Chlorella saccharophila var. ellipsoidea, Chlorella salina, Chlorella simplex, Chlorella sorokiniana, Chlorella sp., Chlorella sphaerica, Chlorella stigmatophora, Chlorella vanniellii, Chlorella vulgaris, Chlorella vulgaris, Chlorella vulgaris f. tertia, Chlorella vulgaris var. autotrophica, Chlorella vulgaris var. viridis, Chlorella vulgaris var. vulgaris, Chlorella vulgaris var. vulgaris f. tertia, Chlorella vulgaris var. vulgaris f. viridis, Chlorella xanthella, Chlorella zofingiensis, Chlorella trebouxioides, Chlorella vulgaris, Chlorococcum infusionum, Chlorococcum sp., Chlorogonium, Chroomonas sp., Chrysosphaera sp., Cricosphaera sp., Crypthecodinium cohnii, Cryptomonas sp., Cyclotella cryptica, Cyclotella meneghiniana, Cyclotella sp., Dunaliella sp., Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera sp., Ellipsoidon sp., Euglena, Franceia sp., Fragilaria crotonensis, Fragilaria sp., Gleocapsa sp., Gloeothamnion sp., Hymenomonas sp., Isochrysis aff. galbana, Isochrysis galbana, Lepocinclis, Micractinium, Micractinium (UTEX LB 2614), Monoraphidium minutum, Monoraphidium sp., Nannochloris sp., Nannochloropsis salina, Nannochloropsis sp., Navicula acceptata, Navicula biskanterae, Navicula pseudotenelloides, Navicula pelliculosa, Navicula saprophila, Navicula sp., Nephrochloris sp., Nephroselmis sp., Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia sp., Ochromonas sp., Oocystis parva, Oocystis pusilla, Oocystis sp., Oscillatoria limnetica, Oscillatoria sp., Oscillatoria subbrevis, Pascheria acidophila, Pavlova sp., Phagus, Phormidium, Platymonas sp., Pleurochrysis carterae, Pleurochrysis dentate, Pleurochrysis sp., Prototheca wickerhamii, Prototheca stagnora, Prototheca portoricensis, Prototheca moriformis, Prototheca zopfii, Pyramimonas sp., Pyrobotrys, Sarcinoid chrysophyte, Scenedesmus armatus, Schizochytrium, Spirogyra, Spirulina platensis, Stichococcus sp., Synechococcus sp., Tetraedron, Tetraselmis sp., Tetraselmis suecica, Thalassiosira weissflogii, and Viridiella fridericiana.

In varying embodiments, the chloroplast, nucleus, cell and/or organism is from a higher plant or vascularized plant. Illustrative and additional plant species of interest include without limitation, Brassicaceae (broccoli, cabbage, cauliflower, kale), Solanaceae (e.g., tomato, potato, tobacco), Phaseoleae (e.g., soybean), Zea (e.g., corn) and Oryzeae (e.g., rice).

4. Methods of Producing

Recombinant expression of proteins from heterologous polynucleotides incorporated into the nuclear and/or chloroplast genome of a photosynthetic (e.g., algal) host cell, particularly a Chlorophyta (green algae) host cell of the genus Chlamydomonas, in particular Chlamydomonas reinhardtii, is known in the art, finds use, and is described in numerous publications, including, e.g., in Rasala and Mayfield, Bioeng Bugs. (2011) 2(1):50-4; Rasala, et al., Plant Biotechnol J. (2011) May 2, PMID 21535358; Coragliotti, et al., Mol Biotechnol. (2011) 48(1):60-75; Specht, et al., Biotechnol Lett. (2010) 32(10):1373-83; Rasala, et al., Plant Biotechnol J. (2010) 8(6):719-33; Mulo, et al., Biochim Biophys Acta. (2011) May 2, PMID:21565160; and Bonente, et al., Photosynth Res. (2011) May 6, PMID:21547493; U.S. Patent Publication No. 2012/0309939; U.S. Patent Publication No. 2010/0129394; and Intl. Publication No. WO 2012/170125. All of the foregoing references are incorporated herein by reference in their entirety for all purposes.

a. Culturing of Cells or Organisms

The photosynthetic organism containing the recombinant polynucleotides encoding one or more colostrum/milk polypeptides can be grown under conditions which permit photosynthesis, however, this is not a requirement (e.g., a host organism may be grown in the absence of light). In some instances, the host organism may be genetically modified in such a way that its photosynthetic capability is diminished or destroyed. In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or an organism-specific requirement. Organic carbon sources include any source of carbon which the host organism is able to metabolize including, but not limited to, acetate, simple carbohydrates (e.g., glucose, sucrose, and lactose), complex carbohydrates (e.g., starch and glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

Organisms can be grown on a defined minimal medium (for example, high salt medium (HSM), modified artificial sea water medium (MASM), or F/2 medium) with light as the sole energy source. In other instances, the organism can be grown in a medium (for example, tris acetate phosphate (TAP) medium), and supplemented with an organic carbon source.

Organisms, such as algae, can grow naturally in fresh water or marine water. Culture media for freshwater algae can be, for example, synthetic media, enriched media, soil water media, and solidified media, such as agar. Various culture media have been developed and used for the isolation and cultivation of fresh water algae and are described in Watanabe, M. W. (2005). Freshwater Culture Media. In R. A. Andersen (Ed.), Algal Culturing Techniques (pp. 13-20).

Elsevier Academic Press, 2005. Culture media for marine algae can be, for example, artificial seawater media or natural seawater media. Guidelines for the preparation of media are described in Harrison, P. J. and Berges, J. A. (2005). Marine Culture Media. In R. A. Andersen (Ed.), Algal Culturing Techniques (pp. 21-33). Elsevier Academic Press, 2005.

Culturing techniques for algae are well known to one of skill in the art and are described, for example, in Freshwater Culture Media. In R. A. Andersen (Ed.), Algal Culturing Techniques. Elsevier Academic Press, 2005. See also, Richmond and Hu, Handbook of Microalgal Culture: Applied Phycology and Biotechnology, Wiley-Blackwell; 2nd edition (Jun. 4, 2013). In varying embodiments, algae can be grown in a bioreactor or a fermenter using either sunlight or reduced carbon as an energy source.

*Chlamydomonas* sp., *Scenedesmus* sp., and *Chlorella* sp. are illustrative algae that can be cultured as described herein and can grow under a wide array of conditions.

One organism that can be cultured as described herein is a commonly used laboratory species *C. reinhardtii*. Cells of this species are haploid, and can grow on a simple medium of inorganic salts, using photosynthesis to provide energy. This organism can also grow in total darkness if acetate is provided as a carbon source. *C. reinhardtii* can be readily grown at room temperature under standard fluorescent lights. In addition, the cells can be synchronized by placing them on a light-dark cycle. Other methods of culturing *C. reinhardtii* cells are known to one of skill in the art.

b. Introduction of Polynucleotide into a Host Organism or Cell

To generate a genetically modified host cell, a polynucleotide, or a polynucleotide cloned into a vector, is introduced stably or transiently into a host cell, using established techniques, including, but not limited to, electroporation, biolistic, calcium phosphate precipitation, DEAE-dextran mediated transfection, and liposome-mediated transfection. For transformation, a polynucleotide of the present disclosure will generally further include a selectable marker, e.g., any of several well-known selectable markers such as restoration of photosynthesis, or kanamycin resistance or spectinomycin resistance. Additional selectable markers of use include without limitation neomycin resistance, ampicillin resistance, tetracycline resistance, chloramphenicol resistance, zeocin resistance, hygromycin resistance and paromomycin resistance.

A polynucleotide or recombinant nucleic acid molecule described herein, can be introduced into a cell (e.g., alga cell) using any method known in the art. A polynucleotide can be introduced into a cell by a variety of methods, which are well known in the art and selected, in part, based on the particular host cell. For example, the polynucleotide can be introduced into a cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (for example, as described in Potrykus, Ann. Rev. Plant. Physiol. Plant Mol. Biol. 42:205-225, 1991).

As discussed above, microprojectile mediated transformation can be used to introduce a polynucleotide into a cell (for example, as described in Klein et al., Nature 327:70-73, 1987). This method utilizes microprojectiles such as gold or tungsten, which are coated with the desired polynucleotide by precipitation with calcium chloride, spermidine or poly-ethylene glycol. The microprojectile particles are accelerated at high speed, into a cell using a device such as the BIOLISTIC PD-1000 particle gun (BioRad; Hercules Calif.). Methods for the transformation using biolistic methods are well known in the art (for example, as described in Christou, Trends in Plant Science 1:423-431, 1996). Microprojectile mediated transformation has been used, for example, to generate a variety of transgenic plant species, including cotton, tobacco, corn, hybrid poplar and *papaya*. Important cereal crops such as wheat, oat, barley, sorghum and rice also have been transformed using microprojectile mediated delivery (for example, as described in Duan et al., Nature Biotech. 14:494-498, 1996; and Shimamoto, Curr. Opin. Biotech. 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, and the glass bead agitation method.

The basic techniques used for transformation and expression in photosynthetic microorganisms are similar to those commonly used for *E. coli, Saccharomyces cerevisiae* and other species. Transformation methods customized for photosynthetic microorganisms, e.g., into the nuclear genome of a strain of algae, are known in the art. These methods have been described in a number of texts for standard molecular biological manipulation (see Packer & Glaser, 1988, "Cyanobacteria", Meth. Enzymol., Vol. 167; Weissbach & Weissbach, 1988, "Methods for plant molecular biology," Academic Press, New York, Green and Sambrook, Molecular Cloning, A Laboratory Manual, 4th Ed., Cold Spring Harbor Press, (2012); and Clark M S, 1997, Plant Molecular Biology, Springer, N.Y.). These methods include, for example, biolistic devices (See, for example, Sanford, Trends In Biotech. (1988).delta.: 299-302, U.S. Pat. No. 4,945,050; electroporation (Fromm et al., Proc. Nat'l. Acad. Sci. (USA) (1985) 82: 5824-5828); use of a laser beam, electroporation, microinjection or any other method capable of introducing DNA into a host cell.

When nuclear transformation is utilized, the protein can be modified for ER targeting by employing plant cell nuclear transformation constructs wherein DNA coding sequences of interest are fused to any of the available transit peptide sequences capable of facilitating transport of the encoded proteins into plant ER, and driving expression by employing an appropriate promoter. Targeting of the protein can be achieved by fusing DNA encoding ER localization to the 5' end of the DNA and aan ER retention sequence to the 3' end of the DNA encoding the protein. The sequences that encode a ER signal sequence can be obtained, for example, from plant nuclear-encoded ER or secreted proteins, such as ars1, ars2, or BiP. The encoding sequence for signal sequence effective in transport to the ER can include all or a portion of the encoding sequence for a particular transit peptide, and may also contain portions of the mature protein encoding sequence associated with a particular transit peptide. Numerous examples of transit peptides that can be used to deliver target proteins into the ER exist, and the particular transit peptide encoding sequences useful in the present disclosure are not critical as long as delivery into the ER is obtained. Proteolytic processing within the ER then produces the mature protein.

In some embodiments, an alga is transformed with one or more polynucleotides which encode one or more milk/colostrum polypeptides, as described herein.

In one embodiment, a transformation may introduce a nucleic acid into a nuclear genome of the host alga. In another embodiment, a transformation may introduce a nucleic acid into the nuclear genome of the host alga. In still another embodiment, a transformation may introduce nucleic acids into both the nuclear genome and into a plastid.

Plastid transformation is a routine and well known method for introducing a polynucleotide into a plant cell chloroplast (see U.S. Pat. Nos. 5,451,513, 5,545,817, and 5,545,818; WO 95/16783; McBride et al., Proc. Natl. Acad. Sci., USA 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation (Svab et al., Proc. Natl. Acad. Sci., USA 87:8526-8530, 1990), and can result in stable homoplasmic transformants, at a frequency of approximately one per 100 bombardments of target leaves.

Transformed cells can be plated on selective media following introduction of exogenous nucleic acids. This method may also comprise several steps for screening. A screen of primary transformants can be conducted to determine which clones have proper insertion of the exogenous nucleic acids. Clones which show the proper integration may be propagated and re-screened to ensure genetic stability. Such methodology ensures that the transformants contain the genes of interest. In many instances, such screening is performed by polymerase chain reaction (PCR); however, any other appropriate technique known in the art may be utilized. Many different methods of PCR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells to which (which chelates magnesium) is added to chelate toxic metals. Following the screening for clones with the proper integration of exogenous nucleic acids, clones can be screened for the presence of the encoded protein(s) and/or products. Protein expression screening can be performed by Western blot analysis and/or enzyme activity assays. Product screening may be performed by any method known in the art, for example mass spectrometry, SDS PAGE protein gels, or HPLC or FPLC chromatography.

The expression of the colostrum/milk protein can be accomplished by inserting a polynucleotide sequence (gene) encoding the protein or enzyme into the chloroplast or nuclear genome of a microalgae. The modified strain of microalgae can be made homoplasmic to ensure that the polynucleotide will be stably maintained in the chloroplast genome of all descendents. A microalga is homoplasmic for a gene when the inserted gene is present in all copies of the chloroplast genome, for example. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% or more of the total soluble plant protein. The process of determining the plasmic state of an organism of the present disclosure involves screening transformants for the presence of exogenous nucleic acids and the absence of wild-type nucleic acids at a given locus of interest.

c. Vectors

Numerous suitable expression vectors are known to those of skill in the art. The following vectors are provided by way of example; for bacterial host cells: pQE vectors (Qiagen), pBluescript plasmids, pNH vectors, lambda-ZAP vectors (Stratagene), pTrc99a, pKK223-3, pDR540, and pRIT2T (Pharmacia); for eukaryotic host cells: pXT1, pSG5 (Stratagene), pSVK3, pBPV, pMSG, pET21a-d(+) vectors (Novagen), and pSVLSV40 (Pharmacia). However, any other plasmid or other vector may be used so long as it is compatible with the host cell. For example, illustrative vectors including without limitation, hsp70/rbcs2 fusion promoter driving ble-2a-GOI (gene of interest); targeted to the cytoplasm (Rasala, et al, PLoS One. (2012) 7(8): e43349); hsp70/rbcs2 fusion promoter driving ble-2a-GOI, targeted to the ER (Rasala, et al., PLoS One. (2014) 9(4): e94028); and hsp70/rbcs2 fusion promoter driving ble-2a-GOI, targeted to the chloroplast (Rasala, et al., PLoS One. (2014) 9(4):e94028).

Knowledge of the chloroplast or nuclear genome of the host organism, for example, *C. reinhardtii*, is useful in the construction of vectors for use in the disclosed embodiments. Chloroplast vectors and methods for selecting regions of a chloroplast genome for use as a vector are well known (see, for example, Bock, J. Mol. Biol. 312:425-438, 2001; Staub and Maliga, Plant Cell 4:39-45, 1992; and Kavanagh et al., Genetics 152:1111-1122, 1999, each of which is incorporated herein by reference). The entire chloroplast genome of *C. reinhardtii* is available to the public on the world wide web, at the URL "biology.duke.edu/chlamy_genome/-chloro.html" (see "view complete genome as text file" link and "maps of the chloroplast genome" link; J. Maul, J. W. Lilly, and D. B. Stern, unpublished results; revised Jan. 28, 2002; to be published as GenBank Ace. No. AF396929; and Maul, J. E., et al. (2002) The Plant Cell, Vol. 14 (2659-2679)). Generally, the nucleotide sequence of the chloroplast genomic DNA that is selected for use is not a portion of a gene, including a regulatory sequence or coding sequence. For example, the selected sequence is not a gene that if disrupted, due to the homologous recombination event, would produce a deleterious effect with respect to the chloroplast. For example, a deleterious effect on the replication of the chloroplast genome or to a plant cell containing the chloroplast. In this respect, the website containing the *C. reinhardtii* chloroplast genome sequence also provides maps showing coding and non-coding regions of the chloroplast genome, thus facilitating selection of a sequence useful for constructing a vector (also described in Maul, I. E., et al. (2002) The Plant Cell, Vol. 14 (2659-2679)). For example, the chloroplast vector, p322, is a clone extending from the Eco (Eco RI) site at about position 143.1 kb to the Xho (Xho I) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlam-y/chloro/chloro140.html").

In addition, the entire nuclear genome of *C. reinhardtii* is described in Merchant, S. S., et al., Science (2007), 318

(5848):245-250, thus facilitating one of skill in the art to select a sequence or sequences useful for constructing a vector.

For expression of the colostrum/milk polypeptide in a host, an expression cassette or vector may be employed. The expression vector will comprise a transcriptional and translational initiation region, which may be inducible or constitutive, where the coding region is operably linked under the transcriptional control of the transcriptional initiation region, and a transcriptional and translational termination region. These control regions may be native to the gene, or may be derived from an exogenous source. Expression vectors generally have convenient restriction sites located near the promoter sequence to provide for the insertion of nucleic acid sequences encoding exogenous proteins. A selectable marker operative in the expression host may be present in the vector.

The nucleotide sequences disclosed herein may be inserted into a vector by a variety of methods. In the most common method the sequences are inserted into an appropriate restriction endonuclease site(s) using procedures commonly known to those skilled in the art and detailed in, for example, Green and Sambrook, Molecular Cloning, A Laboratory Manual, 4th Ed., Cold Spring Harbor Press, (2012) and Ausubel et al., Current Protocols in Molecular Biology, John Wiley & Sons (through 2013).

Further provided are host cells that can be transformed with vectors. One of skill in the art will recognize that such transformation includes transformation with circular vectors, linearized vectors, linearized portions of a vector, or any combination of the above. Thus, a host cell comprising a vector may contain the entire vector in the cell (in either circular or linear form), or may contain a linearized portion of a vector of the present disclosure.

d. Colostrum/Milk Protein Expression

To determine percent total soluble protein, immunoblot signals from known amounts of purified protein can be compared to that of a known amount of total soluble protein lysate. Other techniques for measuring percent total soluble protein are known to one of skill in the art. For example, an ELISA assay or protein mass spectrometry (for example, as described in Varghese, R. S. and Ressom, H. W., Methods Mol. Bio. (2010) 694:139-150) can also be used to determine percent total soluble protein.

In some embodiments, the one or more colostrum/milk polypeptides are produced in a genetically modified host cell at a level that is at least about 0.5%, at least about 1%, at least about 1.5%, at least about 2%, at least about 2.5%, at least about 3%, at least about 3.5%, at least about 4%, at least about 4.5%, or at least about 5% of the total soluble protein produced by the cell. In other embodiments, the colostrum/milk compound is produced in a genetically modified host cell at a level that is at least about 0.15%, at least about 0.1%, or at least about 1% of the total soluble protein produced by the cell. In other embodiments, the colostrum/milk compound is produced in a genetically modified host cell at a level that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, or at least about 70% of the total soluble protein produced by the cell.

Expression of the milk/colostrum polypeptides in the photosynthetic (e.g., algal) host cell can be detected using any method known in the art, e.g., including immunoassays (ELISA, Western Blot) and/or nucleic acid assays (RT-PCR). Sequences of expressed polypeptides can be confirmed using any method known in the art (e.g., mass spectrometry).

Milk/colostrum polypeptides expressed in a photosynthetic (e.g., algal) host cell are generally properly folded without performing denaturation and refolding. Furthermore, the polypeptides expressed in the chloroplast genome are not glycosylated, so coding sequences do not need to be altered to remove glycosylation sites and glycosylated moieties do not need to be removed post-translationally.

e. Colostrum/Milk Protein Bioactivity

The bioactivity of the expressed colostrum milk polypeptides can be determined using any method known in the art. For example, lysozyme bioactivity can be measured by determining the activity of cell lysates or purified polypeptide to effect killing of gram positive bacteria (e.g., *micrococcus* cells). See, e.g., Ito, et al., *Chem Pharm Bull* (Tokyo). 1992 June; 40(6):1523-6 and Morsky, et al., *Anal Biochem.* 1983 January; 128(1):77-85. Lactadherin bioactivity can be determined by measuring binding to phosphatidylserine. See, e.g., Otzen, et al., *Biochim Biophys Acta.* (2012) 1818(4):1019-27; Hou, et al., *Vox Sang.* 2011 February; 100(2):187-95 and Dasgupta, et al., *Transl Res.* 2006 July; 148(1):19-25. The bioactivity of osteopontin can be measured by the ability of osteopontin to adhere to human embryonic 293 cells when in the presence of the divalent cations, $Mg^{2+}$ or $Mn^{2+}$ but not $Ca^{2+}$. See, e.g., Hu, et al, *J Biol Chem*. (1995) 270(17):9917-25; and Agnihotri, et al., *J Biol Chem* (2001) 276:28261-28267. CD14 bioactivity can be determined by measuring binding to lipopolysaccharide (LPS). See, e.g., Wright, et al., *Science*. 1990 Sep. 21; 249(4975):1431-3. Cathelicidin-1 activity can be determined using an antimicrobial assay and measuring luminescence. See, e.g., Sue, et al. *Infect Immun.* 2000 May; 68(5) 2748-2755. MAA bioactivity can be determined by measuring the induction of mucin3 expression by intestinal epithelial cells. See, e.g. Manuell. et al., *Plant Biotechnology J*, 2007 May; 5(3):402-12. Lingual antimicrobial peptide (LAP) and cathelicidin-1 bioactivity can be determined by measuring bactericidial activity. See, Tomasinsig, et al., *J Pept Sci.* 2012 February; 18(2):105-13. Alpha-lactalbumin bioactivity can be determined by measuring lactase synthase activity. See, Fitzgerald, et al., *Anal Biochem.* 1970 July; 36(1):43-61. The bioactivity of a polypeptide is determined in a test assay known in the art and the bioactivity of the test polypeptide can be compared to a positive control (e.g., a known bioactive polypeptide or a native polypeptide) and a negative control (e.g., no peptide or a known biologically inactive polypeptide). In varying embodiments, colostrum/milk polypeptides produced in the nuclei of photosynthetic organisms are characterized by at least 50%, 75%, 85%, 90%, 95% 98%, 99% and even up to 100% of the level of bioactivity of the natural colostrum-derived counterpart protein.

5. Compositions

Further provided are compositions comprising the one or more colostrum/milk polypeptides. Generally, the colostrum/milk polypeptides need not be purified or isolated from the host cell. A distinct advantage of the compositions and methods described herein is that administration of the bioactive protein-expressing organism, without purification or isolation, to a patient, e.g., a human or non-human mammal, confers a clinical or nutritional benefit. For example, administration of photosynthetic organisms comprising nuclear-expressed milk/colostrum polypeptides, e.g. osteopontin, to the gastrointestinal tract, e.g., orally, and is efficiently absorbed and assimilated into bodily tissues such as bone and immune cells. Accordingly, in varying embodiments, the compositions comprise the photosynthetic (e.g., algal) host cells which have been engineered to express one or more colostrum/milk polypeptides. In varying embodiments, the compositions are edible by a mammal. The edible compositions can take the form of a liquid or beverage (e.g., infant formula), a food, a feed, a food supplement, a nutraceutical (e.g., a pill). In varying embodiments, the compositions comprise a compressed algal cake (e.g., a compressed solid mass of algal cells), algal paste and/or algal powder. In varying embodiments, the compositions are lyophilized or spray dried. In some embodiments, the photosynthetic organisms (e.g., algae) are lyophilized or spray-dried prior to the addition to an edible composition, e.g., a food, beverage or tablet consumable by a mammal, e.g., a human, a canine, a feline. In some embodiments, the photosynthetic organisms (e.g., algae) are formulated into a wet paste prior to the addition to an edible composition, e.g., a food, beverage or tablet consumable by a mammal, e.g., a human, a canine, a feline. In some embodiments, the photosynthetic organisms (e.g., algae) are formulated into a powder to be sprinkled onto or into an edible composition, e.g., a food, beverage or tablet consumable by a mammal, e.g., a human, a canine, a feline. In some embodiments the photosynthetic organisms (e.g., algae) are blended or mixed into an edible composition, e.g., a food, beverage or tablet consumable by a mammal, e.g., a human, a canine, a feline.

EXAMPLES

The following examples are offered to illustrate, but not to limit the claimed invention.

Example 1: Nuclear-Expressed Bovine Milk Lysozyme

The cDNA encoding for bovine milk Lysozyme was codon-optimized and synthesized to match the codon usage of genes expressed from the nuclear genome of C. reinhardtii (FIG. 2). The cDNA was cloned into a transformation vector designed for integration and expression from the nuclear genome of C. reinhardtii, containing endogenous promoters and untranslated regions. The transformation vector was electroporated as follows: C. reinhardtii strain cc1690 was grown to $3-6 \times 10^6$ cells/ml in TAP (Tris-acetate-phosphate) medium at 23° C. under constant illumination of 5000 lux on a rotary shaker. Cells were harvested by centrifugation and resuspended in TAP medium supplemented with 40 mM sucrose at a concentration of $3 \times 10^8$ cells/ml. 250 µLs of cells were incubated with 300-1000 ng of digested transformation plasmid for 5-10 minutes on ice in a 4 mm cuvette. An exponential electric pulse of 2000 V/cm was applied to the sample using a GenePulser XCell™ (BioRad, Hercules, Calif.) electroporation apparatus. The capacitance was set at 25 µF and no shunt resistor was used. Cells were recovered for 18 hours in 10 mls of TAP/40 mM sucrose and then plated to two TAP/agar plates supplemented with 5-10 µg/ml of zeocin. Selection plates were placed at 23° C. in 5000 lux for one week to allow for untransformed cells to clear and transformed colonies to appear.

Colonies were patched to TAP/zeocin plates and stable integration of lysozyme was determined by PCR analysis of cell lysates. Cells were resuspended in TrisEDTA solution and heated to 95° C. for 10 min. The cell lysate was then used as a template for PCR under standard conditions for 40 cycles using the Phusion enzyme (NEB, Ipswich, Mass.) in the presence of GC buffer (NEB, Ipswich, Mass.) and 1M betaine. The oligonucleotides 5'-GGTCGTGTCCAC-GAACTTCC-3' (SEQ ID NO: 48) and 5'-CACGCGGCA-GCCCTG-3' (SEQ ID NO: 49) were used.

Ten individual gene-positive clones were chosen for protein expression analysis. Cells were struck onto TAP/zeocin plates and incubated at 23° C. in 5000 lux for 3 4 days. Biomass was then scraped from the plates into lysis buffer (50 mM Tris pH 7.9, 150 mM NaCl, 0.1% Triton) and sonicated at 4° C., 10% power for 1 second on, 1 second off for 30 total seconds on. Soluble protein extract was incubated with 40 µLs of FLAG-resin (Sigma) for 1 hour at 4° C. The resin was collected by centrifugation and bound protein was eluted by boiling the resin in 1× Laemmli sample buffer. Samples were analyzed using SDS-PAGE Western blotting, probing the membranes with and anti-FLAG antibody conjugated to alkaline phosphatase (Sigma). Of the ten lysozyme gene-positive clones analyzed, seven expressed detectible levels of lysozyme FLAG-tagged protein.

A single clone was grown in liquid TAP in a 20-liter bioreactor for lysozyme protein purification and analysis. 20 liters of TAP was inoculated with a saturated 250 ml culture and grown for 4-5 days at 23° C. in 5000 lux of light with bubbling air. Biomass was collected and soluble protein extracts were prepared as described above. 1 ml of FLAG-resin was used for lysozyme protein purification (0.6 mg binding capacity). Resin and algae protein extract were incubated for 1 hour at 4° C. in batch. The resin was washed 3-4 times with PBS in batch and eluted with 5×1 ml of 0.1 M glycine, 400 mM NaCl pH 3.5. Elutions were analyzed for the presence of lysozyme by Western blotting with an anti-FLAG antibody. Elutions containing lysozyme were collected and buffer exchanged into PBS. Protein was concentrated, quantitated, and frozen in aliquots at −20° C.

Purified protein was analyzed by Coomassie staining and Western blotting to verify presence and purity of protein (FIG. 11). To confirm the presence of lysozyme, mass spectrometry was performed.

To determine whether algal-expressed lysozyme is bioactive, an activity assay was performed with purified algal-produced lysozyme. Lysozyme is a glycan hydrolase with antibacterial properties (Irwin, J. Mol. Evol. 41, 299-312 (1995)). It damages the cell wall of gram-positive bacteria and causes cell lysis. We incubated algae-expressed purified lysozyme with the gram-positive bacterium Micrococcus sp. Algal-produced lysozyme activity—bacterial cell lysis—was measured as a drop in bacterial cell absorbance at 450 nm (FIG. 14D). A negative control (buffer only) and a positive control (commercially available purified lysozyme) were also included. This data indicate that algae-expressed lysozyme can induce bacterial cell lysis and is therefore bioactive.

FIG. 14D illustrates lysozyme bioactivity in the presence algal protein extracts (non-purified) against Micrococcus sp. Transgenic algae lysate containing lysozyme was incubated with the gram-positive bacterium Micrococcus sp. Lysozyme activity—bacterial cell killing—was measured as a drop in bacterial cell absorbance at 450 nm (FIG. 14D). Wild-type algae lysate was also included and did not display antibacterial activity. This data indicate that transgenic algae cell lysates containing algae-expressed and non-purified/non-enriched lysozyme displays antimicrobial activity.

Example 2: Nuclear-Expressed Lactadherin

The cDNA encoding for bovine lactadherin/MFG-E8 was codon-optimized and synthesized to match the codon usage of genes expressed from the nuclear genome of *C. reinhardtii* (FIG. 3). The cDNA was cloned into a transformation vector designed for integration and expression from the nuclear genome of *C. reinhardtii*, containing endogenous promoters and untranslated regions. The transformation vector was electroporated as follows: *C. reinhardtii* strain cc1690 was grown to 3-6×10$^6$ cells/ml in TAP (Tris-acetate-phosphate) medium at 23° C. under constant illumination of 5000 lux on a rotary shaker. Cells were harvested by centrifugation and resuspended in TAP medium supplemented with 40 mM sucrose at a concentration of 3×10$^8$ cells/ml. 250 µLs of cells were incubated with 300-1000 ng of digested transformation plasmid for 5-10 minutes on ice in a 4 mm cuvette. An exponential electric pulse of 2000 V/cm was applied to the sample using a GenePulser XCell™ (BioRad, Hercules, Calif.) electroporation apparatus. The capacitance was set at 25 µF and no shunt resistor was used. Cells were recovered for 18 hours in 10 mLs of TAP/40 mM sucrose and then plated to two TAP/agar plates supplemented with 5-10 µg/M of zeocin. Selection plates were placed at 23° C. in 5000 lux for one week to allow for untransformed cells to clear and transformed colonies to appear.

Colonies were patched to TAP/zeocin plates and stable integration of lactadherin was determined by PCR analysis of cell lysates. Cells were resuspended in TrisEDTA solution and heated to 95° C. for 10 min. The cell lysate was then used as a template for PCR under standard conditions for 40 cycles using the Phusion enzyme (NEB, Ipswich, Mass.) in the presence of GC buffer (NEB, Ipswich, Mass.) and 1M betaine. The oligonucleotides 5'-GGTCGTGTCCAC-GAACTTCC-3' (SEQ ID NO: 48) and 5' CCTTGTAGTCg-gatccGCAGCCCAGCAGCTC-3' (SEQ ID NO: 50) were used.

Five individual gene-positive clones were chosen for protein expression analysis. Cells were struck onto TAP/zeocin plates and incubated at 23° C. in 5000 lux for 3-4 days. Biomass was then scraped from the plates into lysis buffer (50 mM Tris pH 7.9, 150 mM NaCl, 0.1% Triton) and sonicated at 4° C., 10% power for 1 second on, 1 second off for 30 total seconds on. Soluble protein extract was incubated with 40 µLs of FLAG-resin (Sigma) for 1 hour at 4° C. The resin was collected by centrifugation and bound protein was eluted by boiling the resin in 1× Laemmli sample buffer. Samples were analyzed using SDS-PAGE Western blotting, probing the membranes with and anti-FLAG antibody conjugated to alkaline phosphatase (Sigma). Of the five lactadherin gene-positive clones analyzed, two expressed detectible levels of lactadherin FLAG-tagged protein.

A single clone was grown in liquid TAP in a 20-liter bioreactor for lactadherin protein purification and analysis. 20 liters of TAP was inoculated with a saturated 250 ml culture and grown for 4-5 days at 23° C. in 5000 lux of light with bubbling air. Biomass was collected and soluble protein extracts were prepared as described above. 1 ml of FLAG-resin was used for lactadherin protein purification (0.6 mg binding capacity). Resin and algae protein extract were incubated for 1 hour at 4° C. in batch. The resin was washed 3-4 times with PBS in batch and eluted with 5×1 ml of 0.1 M glycine, 400 mM NaCl pH 3.5. Elutions were analyzed for the presence of lactadherin by Western blotting with an anti-FLAG antibody. Elutions containing lactadherin were collected and buffer exchanged into PBS. Protein was concentrated, quantitated, and frozen in aliquots at −20° C.

Purified protein was analyzed by Coomassie staining and Western blotting to verify presence and purity of protein (FIG. 11). To confirm the presence of lactadherin, mass spectrometry was performed.

To determine whether algal-expressed lactadherin is bioactive, an activity assay was performed with purified algal-produced lactadherin. Lactadherin functions in a range of activities including phagocytosis of apoptotic lymphocytes and other apoptotic cells, adhesion between sperm and the egg coat, repair of intestinal mucosa, mammary gland branching morphogenesis, angiogenesis, among others (Raymond, *J. Cell. Biochem.* 106, 957-66 (2009)). Lactadherin contains a phosphatidylserine-binding domain is required for the protein's function in cell adhesion. FIG. 14C illustrates bioactivity of lactadherin expressed from the nuclear genome in binding to phosphatidylserine. Microtiter plates were coated with 3 µg/ml of phosphatidyl-L-serine. 600 nM of lactadherin-FLAG or a negative control protein (MSD1-FLAG) was incubated with immobilized phosphatidyl-L-serine. After washing unbound protein from the wells, the amount of bound FLAG-tagged protein was quantitated using anti-FLAG antibodies conjugated to horseradish peroxidase (HRP). Lactadherin binds to phosphatidylserine, indicating that algae-expressed lactadherin is bioactive.

Example 3: Nuclear-Expressed Soluble CD14

The cDNA encoding for bovine soluble CD14 (sCD14) was codon-optimized and synthesized to match the codon usage of genes expressed from the nuclear genome of *C. reinhardtii* (FIG. 8). The cDNA was cloned into a transformation vector designed for integration and expression from the nuclear genome of *C. reinhardtii*, containing endogenous promoters and untranslated regions. The transformation vector was electroporated as follows: *C. reinhardtii* strain cc1690 was grown to 3-6×10$^6$ cells/ml in TAP (Tris-acetate-phosphate) medium at 23° C. under constant illumination of 5000 lux on a rotary shaker. Cells were harvested by centrifugation and resuspended in TAP medium supplemented with 40 mM sucrose at a concentration of 3×10$^8$ cells/ml. 250 µLs of cells were incubated with 300-1000 ng of digested transformation plasmid for 5-10 minutes on ice in a 4 mm cuvette. An exponential electric pulse of 2000 V/cm was applied to the sample using a GenePulser XCell™ (BioRad, Hercules, Calif.) electroporation apparatus. The capacitance was set at 25 µF and no shunt resistor was used. Cells were recovered for 18 hours in 10 mls of TAP/40 mM sucrose and then plated to two TAP/agar plates supplemented with 5-10 µg/ml of zeocin. Selection plates were placed at 23° C. in 5000 lux for one week to allow for untransformed cells to clear and transformed colonies to appear.

Colonies were patched to TAP/zeocin plates and stable integration of sCD14 was determined by PCR analysis of cell lysates. Cells were resuspended in Tris-EDTA solution and heated to 95° C. for 10 min. The cell lysate was then used as a template for PCR under standard conditions for 40 cycles using the Phusion enzyme (NEB, Ipswich, Mass.) in the presence of GC buffer (NEB, Ipswich, Mass.) and 1M betaine. The oligonucleotides 5'-GGTCGTGTCCAC-GAACTTCC-3' (SEQ ID NO: 48) and 5' CCTTGTAGTCg-gatccGGCGAAGCCGCGCGC-3' (SEQ ID NO: 51) were used.

Four individual gene-positive clones were chosen for protein expression analysis. Cells were struck onto TAP/zeocin plates and incubated at 23° C. in 5000 lux for 3-4 days. Biomass was then scraped from the plates into lysis buffer (50 mM Tris pH 7.9, 150 mM NaCl, 0.1% Triton) and sonicated at 4° C., 10% power for 1 second on, 1 second off for 30 total seconds on. Soluble protein extract was incubated with 40 µls of FLAG-resin (Sigma) for 1 hour at 4° C. The resin was collected by centrifugation and bound protein was eluted by boiling the resin in 1× Laemmli sample buffer. Samples were analyzed using SDS-PAGE Western blotting, probing the membranes with and anti-FLAG antibody conjugated to alkaline phosphatase (Sigma). Of the four sCD14 gene-positive clones analyzed, all four expressed detectible levels of sCD14 FLAG-tagged protein.

A single clone was grown in liquid TAP in a 20-liter bioreactor for sCD14 protein purification and analysis. 20 liters of TAP was inoculated with a saturated 250 ml culture and grown for 4-5 days at 23° C. in 5000 lux of light with bubbling air. Biomass was collected and soluble protein extracts were prepared as described above. 1 ml of FLAG-resin was used for sCD14 protein purification (0.6 mg binding capacity). Resin and algae protein extract were incubated for 1 hour at 4° C. in batch. The resin was washed 3-4 times with PBS in batch and eluted with 5×1 ml of 0.1 M glycine, 400 mM NaCl pH 3.5. Elutions were analyzed for the presence of sCD14 by Western blotting with an anti-FLAG antibody. Elutions containing sCD14 were collected and buffer exchanged into PBS. Protein was concentrated, quantitated, and frozen in aliquots at −20° C.

Purified protein was analyzed by Coomassie staining and Western blotting to verify presence and purity of protein (FIG. 11). To confirm the presence of sCD14, mass spectrometry was performed.

To determine whether algal-expressed sCD14 is bioactive, an activity assay was performed with purified algal-produced sCD14. sCD14 is a pattern recognition receptor in milk that binds to the bacterial endotoxin lipopolysaccharide (LPS) and may prevent LPS toxicity and/or reduce inflammation associated with the immune response to its presence (Vidal, *Adv. Exp. Med. Biol.* 606, 195-216 (2008); Hidaka, *Eur. J. Pharmacol.* 721, 305-12 (2013)). FIG. 14A illustrates bioactivity of sCD14 expressed from the nuclear genome in binding to LPS. Microtiter plates were coated with anti-FLAG antibodies and blocked with bovine serum albumin. 2 ng/µl of soluble CD14-FLAG or a negative control protein (lactadherin-FLAG) was bound to the plates through an affinity interaction between the FLAG-tag and the anti-FLAG antibodies. After washing unbound protein, 100 ng/ml or 250 ng/ml of LPS conjugated to biotin was then incubated with immobilized sCD14 or lactadherin in the presence of 5% bovine serum. After washing unbound LPS-biotin, the amount of LPS bound to sCD14 or lactadherin was quantitated using Streptavidin-horseradish peroxidase (HRP), which binds to the biotin molecule on LPS. The data indicate that sCD14, but not the negative control protein, binds to LPS in a concentration-dependent manner, indicating that algae-expressed sCD14 is bioactive.

Example 4: Expression of Nuclear Mammary Associated Serum Amyloid A3 (MAA) and Chloroplast Osteopontin A cDNA encoding for bovine osteopontin was synthesized in *C. reinhardtii* chloroplast codon bias and ligated into a *C. reinhardtii* chloroplast transformation vector. This vector directed the osteopontin cDNA into the chloroplast genome via homologous recombination and allowed the cDNA to directly replace the psbA gene. This vector also contained regulatory elements, untranslated regions (UTRs) that ensure the stable expression of the osteopontin mRNA.

The transformation vector containing the osteopontin cDNA was introduced into the chloroplast genome by first coating the vector onto 1 µM gold particles and then shooting the gold particles into *C. reinhardtii* cells that had been plated on Tris-Acetate-phosphate (TAP) plates containing 100 µg/mL kanamycin with a particle gun from Bio-Rad laboratory. Places were incubated in the dark for 24 hours followed by an incubation in light with an intensity of 4000 lux for 2 weeks. Transformed algae formed colonies following the incubation. Colonies from the transformation was patched onto TAP plates containing 150 µg/mL kanamycin.

To ensure that colonies from algal chloroplast transformations contained our gene of interest PCR gene screens were done using a forward primer, 5' gtgctaggtaactaacgttt-gattttt-3' (SEQ ID NO: 52), that anneals to the untranslated region of the psbA gene that is used to drive the accumulation of the osteopontin protein and a reverse primer, 5' GGGGGAGCGAATAGGATTAG-3' (SEQ ID NO: 53), that anneals to the chloroplast codon optimized cDNA. The PCR yields a product that is approximately 700 bp. The chloroplast also contains up to 80 copies of its genome. To ensure that the osteopontin is integrated into all copies of the chloroplast genome a PCR screen was done to ensure that the gene that was being replaced was completely removed. Two sets of primers were used: 1. A control set of primers to ensure that the PCR worked amplifies the DNA that encodes for the 16srRNA with a forward primer 5'-ccgaact-gaggttgggttta-3' (SEQ ID NO: 54) and a reverse primer 5' GGGGGAGCGAATAGGATTAG-3' (SEQ ID NO: 53). 2. A set of primers to amplify the psbA gene that resided in the psbA locus of the untransformed strain with a forward primer 5' ggaagggaggacgtaggtacataaa-3' (SEQ ID NO: 55) and a reverse primer 5'-ttagaacgtgttttgttcccaat-3' (SEQ ID NO: 56). The loss of the MAA PCR product indicates a strain that is homoplasmic for mammary associated serum amyloid A3 (MAA).

A cDNA encoding for bovine MAA was synthesized in *C. reinhardtii* nuclear codon bias and ligated into a *C. reinhardtii* nuclear transformation vector. This vector also contained regulatory elements, untranslated regions (UTRs) that ensure the stable expression of the MAA mRNA.

The transformation vector containing the MAA cDNA was introduced into the nuclear genome of the homoplasmic osteopontin-transformed strain by first linearlizing the vector by digesting it with XbaI and Kpn I endonucleases, and then electroporating it into *C. reinhardtii* cells. Cells were recovered for 16 hours followed by an incubation in light with an intensity of 60 µmols m-2 s-1 for 1 weeks on TAP plates supplemented with 5 or 10 µg/ml of zeocin. Transformed algae formed colonies following the incubation. Colonies from the transformation was patched onto TAP plates containing 5-10 µg/mL zeocin.

Thus, the osteopontin expression construct was stabling transformed into the chloroplast genome and the MAA expression cassette was transformed into the nuclear genome of the same cell.

Figure 15:
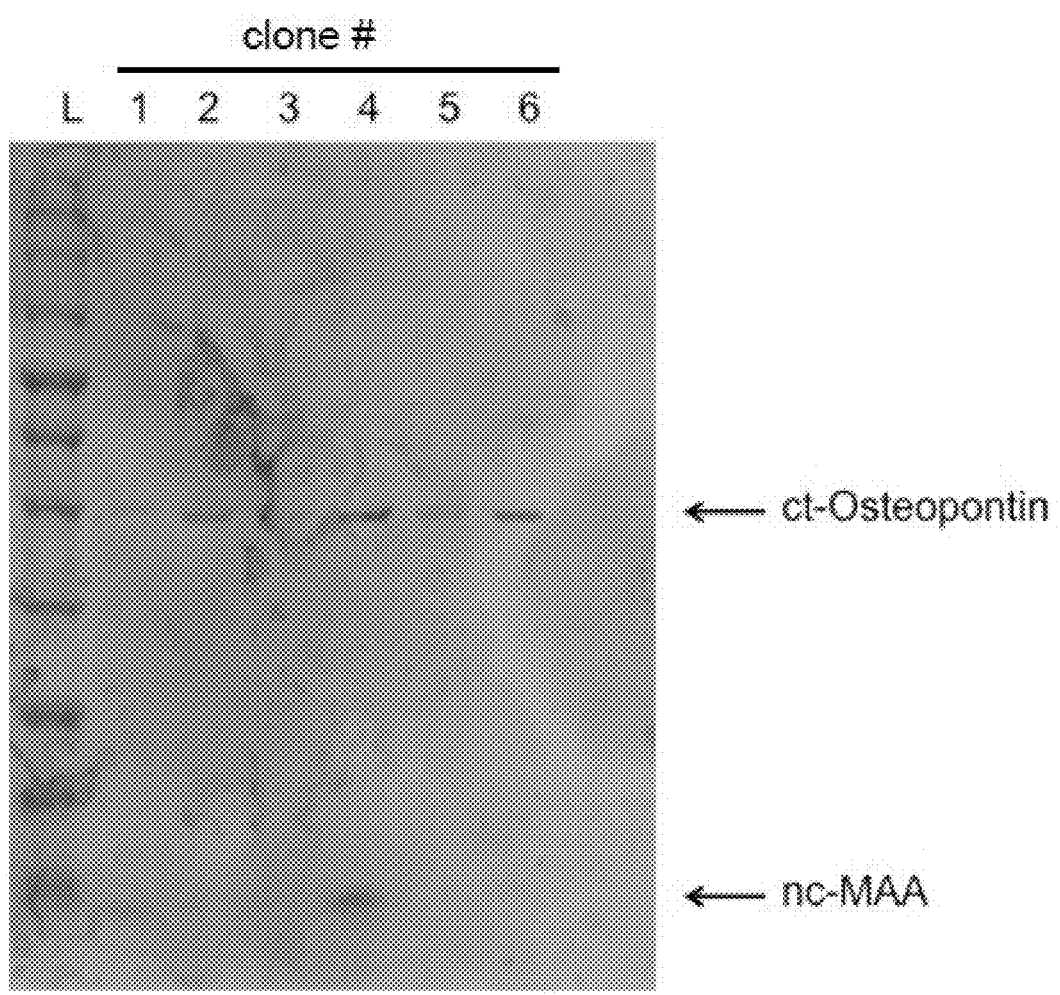
FIG. 15 illustrates a Western blot showing protein co-expression of osteopontin from the chloroplast and mammary-associated serum amyloid A3 (MAA) from the nucleus or nuclear genome in a single algal cell. Western blots were performed on lysates from six independent clones. Osteopontin was detected with anti-FLAG antibodies (upper band) while anti-MAA antibodies were used to detect MAA (lower bands). L, molecular weight ladder.

Clones were checked by Western blot for the presence of both the MAA protein using an anti-MAA antibody and the osteopontin protein using an anti-flag antibody (FIG. 15). FIG. 15 demonstrates strains of algae that produce both the MAA protein and the osteopontin protein.

The commonly owned, co-pending application International Appl. No. PCT/US2015/016460, entitled "COLOSTRUM/MILK PROTEIN COMPOSITIONS," filed on Feb.

19, 2015 is explicitly incorporated by reference in its entirety for its teachings regarding expressions of mammalian colostrum/milk proteins from the chloroplast of a photosynthetic organism.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| INFORMAL SEQUENCE LISTING |
|---|
| Sequence ID No: 1 - osteopontin nucleic acid sequence with optional N-terminal flag tag (underlined) for expression in the chloroplast genome<br>GATTACAAAGATGATGACGATAAAAGTTTACCTGTAAAACCAACATCATCAGGTTCATCAG<br>AAGAAAAACAATTAAATAATAAATATCCAGATGCTGTTGCAATTTGGTTAAAACCTGATCC<br>ATCACAAAAACAAACATTTTTAACACCACAAAATTCAGTATCATCAGAAGAAACAGATGAT<br>AATAAACAAAATACATTACCATCAAAATCAAATGAATCACCAGAACAAACTGATGATTTAG<br>ATGATGATGATGATAATTCACAAGATGTTAATTCAAATGATTCAGATGATGCTGAAACAAC<br>AGATGATCCTGATCATTCAGATGAATCACATCACTCAGATGAATCAGATGAAGTTGATTTT<br>CCTACAGATATTCCAACTATTGCTGTTTTTACACCCATTTATTCCTACAGAATCAGCTAATG<br>ATGGTCGTGGTGATTCAGTAGCTTATGGTTTAAAATCACGTTCAAAAAAATTTCGTCGTTC<br>AAATGTACAATCACCAGATGCTACTGAAGAAGATTTCACATCACACATTGAATCAGAAGAA<br>ATGCACGATGCTCCAAAAAAAACTTCACAATTAACAGATCATTCAAAAGAAACTAATTCAT<br>CAGAATTATCAAAAGAATTAACACCAAAAGCTAAAGATAAAAATAAACATTCAAATTTAAT<br>TGAATCACAAGAAAATTCAAAATTATCACAAGAATTTCATTCATTAGAAGATAAATTAGAT<br>TTAGATCACAAATCAGAAGAAGATAAACATTTAAAAATTCGTATTTCACATGAATTAGATT<br>CAGCTTCATCAGAAGTTAAT<br><br>Sequence ID No: 2 - osteopontin amino acid sequence with optional N-terminal flag tag (underlined)<br><u>DYKDDDDK</u>SLPVKPTSSGSSEEKQLNNKYPDAVAIWLKPDPSQKQTFLTPQNSVSSEETDD<br>NKQNTLPSKSNESPEQTDDLDDDDNSQDVNSNDSDDAETTDDPDHSDESHHSDESDEVDF<br>PTDIPTIAVFTPFIPTESANDGRGDSVAYGLKSRSKKFRRSNVQSPDATEEDFTSHIESEE<br>MHDAPKKTSQLTDHSKETNSSELSKELTPKAKDKNKHSNLIESQENSKLSQEFHSLEDKLD<br>LDHKSEEDKHLKIRISHELDSASSEVN<br><br>Sequence ID No: 3 - lactadherin amino acid sequence with optional N-terminal flag tag (underlined)<br><u>DYKDDDDK</u>SFSGDFCDSSQCLHGGTCLLNEDRTPPFYCLCPEGFTGLLCNETEHGPCFPNP<br>CHNDAECQVTDDSHRGDVFIQYICKCPLGYVGIHCETTCTSPLGMQTGAIADSQISASSMH<br>LGFMGLQRWAPELARLHQTGIVNAWTSGNYDKNPWIQVNLMRKMWVTGVVTQGASRAGSAE<br>YLKTFKVAYSTDGRQFQFIQVAGRSGDKIFIGNVNNSGLKINLFDTPLETQYVRLVPIICH<br>RGCTLRFELLGCELNGCTEPLGLKDNTIPNKQITASSYYKTWGLSAFSWFPYYARLDNQGK<br>FNAWTAQTNSASEWLQIDLGSQKRVTGIITQGARDFGHIQYVAAYRVAYGDDGVTWTEYKD<br>PGASESKIFPGNMDNNSHKKNIFETPFQARFVRIQPVAWHNRITLRVELLGC<br><br>Sequence ID No: 4 - bovine milk lysozyme nucleic acid sequence with optional C-terminal linker in italics, C-terminal flag tag single underlined, and C-terminal KDEL ER retention sequence double underlined for expression in the nuclear genome<br>AAGAAGTTCCAGCGCTGCGAGCTGGCCCGCACCCTGAAGAAGCTGGGCCTGGACGGCTACC<br>GCGGCGTGTCCCTGGCCAACTGGGTGTGCCTGGCCCGCTGGGAGAGCAACTACAACACCCG<br>CGCCACCAACTACAACCGCGGCGACAAGAGCACCGACTACGGCATCTTCCAGATCAACAGC<br>CGCTGGTGGTGCAACGACGGCAAGACCCCCAAGGCCGTGAACGCCTGCCGCATCCCCTGCA<br>GCGCCCTGCTGAAGGACGACATCACCCAGGCCGTGGCCTGCGCCAAGCGCGTCGTGCGCGA<br>CCCCCAGGGCATCAAGGCGTGGGTGGCGTGGCGCAACAAGTGCCAGAACCGCGACCTGCGC<br>AGCTACGTGCAGGGCTGCCGCGTG*ggatcc*<u>GACTACAAGGACGACGACGACAAGGACGAGC<br>TC</u><br><br>Sequence ID No: 5 - bovine milk lysozyme amino acid sequence with optional C-terminal linker in italics, C-terminal flag tag single underlined, and C-terminal KDEL ER retention sequence double underlined for expression in the nuclear genome<br>KKFQRCELARTLKKLGLDGYRGVSLANWVCLARWESNYNTRATNYNRGDKSTDYGIFQINS<br>RWWCNDGKTPKAVNACRIPCSALLKDDITQAVACAKRVVRDPQGIKAWVAWRNKCQNRDLR<br>SYVQGCRV*GS*<u>DYKDDDD</u><u>KDEL</u><br><br>Sequence ID No: 6 - lactadherin nucleic acid sequence with optional C-terminal linker in italics, C-terminal flag tag single underlined, and C-terminal KDEL ER retention sequence double underlined for expression in the nuclear genome<br>TTCAGCGGCGACTTCTGCGACAGCAGCCAGTGCCTGCACGGCGGCACCTGCCTGCTGAACG<br>AGGACCGCACCCCCCCCTTCTACTGCCTGTGCCCCGAGGGCTTCACCGGCCTGCTGTGCAA<br>CGAGACCGAGCACGGCCCCTGCTTCCCCAACCCCTGCCACAACGACGCCGAGTGCCAGGTG<br>ACCGACGACAGCCACCGCGGCGACGTGTTCATCCAGTACATCTGCAAGTGCCCCCTGGGCT<br>ACGTGGGCATCCACTGCGAGACCACCTGCACCTCGCCCCTGGGCATGCAGACCGGCGCGAT<br>CGCCGACAGCCAGATCAGCGCCAGCAGCATGCACCTGGGCTTCATGGGCCTGCAGCGCTGG<br>GCCCCCGAGCTGGCCCGCCTGCACCAGACCGGCATCGTGAACGCCTGGACCAGCGGCAACT<br>ACGACAAGAACCCCGTGGATTCAGGTGAACCTGATGCGCAAGATGTGGGTCACCGGCGTCGT |

INFORMAL SEQUENCE LISTING

```
GACCCAGGGCGCCAGCCGCGCCGGCAGCGCCGAGTACCTGAAGACCTTCAAGGTGGCCTAC
AGCACCGACGGCCGCCAGTTCCAGTTCATCCAGGTGGCCGGCCGCAGCGGCGACAAGATCT
TCATCGGCAACGTGAACAACTCCGGCCTGAAGATCAACCTGTTCGACACCCCCCTGGAGAC
CCAGTACGTGCGCCTGGTGCCCATCATCTGCCACCGCGGCTGCACCCTGCGCTTCGAGCTG
CTGGGCTGCGAGCTGAACGGCTGCACCGAGCCGCTGGGCCTGAAGGACAACACCATCCCCA
ACAAGCAGATCACCGCCTCCAGCTACTACAAGACCTGGGGCCTGAGCGCCTTCTCCTGGTT
CCCCTACTACGCCCGCCTGGACAACCAGGGCAAGTTCAACGCGTGGACCGCCCAGACCAAC
AGCGCCTCCGAGTGGCTGCAGATCGACCTGGGCAGCCAGAAGCGCGTGACCGGCATCATCA
CCCAGGGCGCGCGCGACTTCGGCCACATCCAGTACGTGGCCGCCTACCGCGTGGCCTACGG
CGACGACGGCGTGACCTGGACCGAGTACAAGGACCCCGGCGCCAGCGAGAGCAAGATCTTC
CCGGGCAACATGGACAACAACAGCCACAAGAAGAACATCTTCGAGACCCCCTTCCAGGCCC
GCTTCGTGCGCATCCAGCCCGTGGCCTGGCACAACCGCATCACCCTGCGCGTGGAGCTGCT
GGGCTGCggcggcggaggatccGACTACAAGGACGACGACGACAAGGACGAGCTC
```

Sequence ID No: 7 - lactadherin amino acid sequence with optional C-terminal linker in italics, C-terminal flag tag single underlined, and C-terminal KDEL ER retention sequence double underlined for expression in the nuclear genome FSGDFCDSSQCLHGGTCLLNEDRTPPFYCLCPEGFTGLLCNETEHGPCFPNPCHNDAECQV
TDDSHRGDVFIQYICKCPLGYVGIHCETTCTSPLGMQTGAIADSQISASSMHLGFMGLQRW
APELARLHQTGIVNAWTSGNYDKNPWIQVNLMRKMWVTGVVTQGASRAGSAEYLKTFKVAY
STDGRQFQFIQVAGRSGDKIFIGNVNNSGLKINLFDTPLETQYVRLVPIICHRGCTLRFEL
LGCELNGCTEPLGLKDNTIPNKQITASSYYKTWGLSAFSWFPYYARLDNQGKFNAWTAQTN
SASEWLQIDLGSQKRVTGIITQGARDFGHIQYVAAYRVAYGDDGVTWTEYKDPGASESKIF
PGNMDNNSHKKNIFETPFQARFVRIQPVAWHNRITLRVELLGC*GGGGS*DYKDDDDKDEL Sequence ID No: 8 - osteopontin nucleic acid sequence with optional C-terminal linker in italics, C-terminal flag tag single underlined, and C-terminal KDEL ER retention sequence double underlined for expression in the nuclear genome

```
CTGCCCGTGAAGCCCACCAGCAGCGGCAGCAGCGAGGAGAAGCAGCTGAACAACAAGTACC
CCGACGCCGTGGCCACCTGGCTGAAGCCCGACCCCAGCCAGAAGCAGACCTTCCTGGCCCC
CCAGAACAGCGTGTCCTCCGAGGAGACCGACGACAACAAGCAGAACACCCTGCCCAGCAAG
AGCAACGAGAGCCCCGAGCAGACCGACGACCTGGACGACGACGACGACAACAGCCAGGACG
TGAACAGCAACGACAGCGACGACGCCGAGACCACCGACGACCCCGACCACAGCGACGAGAG
CCACCACTCCGACGAGTCGGACGAGGTGGACTTCCCCACCGACATCCCCACCATCGCGGTG
TTCACCCCCTTCATCCCCACCGAGAGCGCCAACGACGGCCGCGGCGACAGCGTGGCCTACG
GCCTGAAGTCCCGCAGCAAGAAGTTCCGCCGCAGCAACGTGCAGTCGCCCGACGCCACCGA
GGAGGACTTCACCTCCCACATCGAGTCGGAGGAGATGCACGACGCCCCCAAGAAGACCAGC
CAGCTGACCGACCACTCCAAGGAGACCAACAGCTCCGAGCTGAGCAAGGAGCTGACCCCCA
AGGCCAAGGACAAGAACAAGCACAGCAACCTGATCGAGAGCCAGGAGAACAGCAAGCTGTC
CCAGGAGTTCCACAGCCTGGAGGACAAGCTGGACCTGGACCACAAGAGCGAGGAGGACAAG
CACCTGAAGATCCGCATCAGCCACGAGCTGGACAGCGCCTCCAGCGAGGTGAAC*ggcggcg
gaggatcc*GACTACAAGGACGACGACGACAAGGACGAGCTC
```

Sequence ID No: 9 - osteopontin amino acid sequence with optional C-terminal linker in italics, C-terminal flag tag single underlined, and C-terminal KDEL ER retention sequence double underlined for expression in the nuclear genome LPVKPTSSGSSEEKQLNNKYPDAVATWLKPDPSQKQTFLAPQNSVSSEETDDNKQNTLPSK
SNESPEQTDDLDDDDDNSQDVNSNDSDDAETTDDPDHSDESHHSDESDEVDFPTDIPTIAV
FTPFIPTESANDGRGDSVAYGLKSRSKKFRRSNVQSPDATEEDFTSHIESEEMHDAPKKTS
QLTDHSKETNSSELSKELTPKAKDKNKHSNLIESQENSKLSQEFHSLEDKLDLDHKSEEDK
HLKIRISHELDSASSEVN*GGGGS*DYKDDDDKDEL Sequence ID No: 10 -alpha-lactalbumin nucleic acid sequence with optional C-terminal linker in italics, C-terminal flag tag single underlined, and C-terminal KDEL ER retention sequence double underlined for expression in the nuclear genome

```
GAGCAGCTGACCAAGTGCGAGGTGTTCCGCGAGCTGAAGGACCTGAAGGGCTACGGCGGCG
TGTCGCTGCCCGAGTGGGTGTGCACCACCTTCCACACCAGCGGCTACGACACCCAGGCGAT
CGTGCAGAACAACGACAGCACCGAGTACGGCCTGTTCCAGATCAACAACAAGATCTGGTGC
AAGGACGACCAGAACCCCCACAGCAGCAACATCTGCAACATCAGCTGCGACAAGTTCCTGG
ACGACGACCTGACCGACGACATTATGTGCGTGAAGAAGATCCTGGACAAGGTGGGCATCAA
CTACTGGCTGGCCCACAAGGCCCTGTGCAGCGAGAAGCTGGACCAGTGGCTGTGCGAGAAG
CTG*ggcggcggaggatcc*GACTACAAGGACGACGACGACAAGGACGAGCTC
```

Sequence ID No: 11 -alpha-lactalbumin amino acid sequence with optional C-terminal linker in italics, C-terminal flag tag single underlined, and C-terminal KDEL ER retention sequence double underlined for expression in the nuclear genome EQLTKCEVFRELKDLKGYGGVSLPEWVCTTFHTSGYDTQAIVQNNDSTEYGLFQINNKIWC
KDDQNPHSSNICNISCDKFLDDDLTDDIMCVKKILDKVGINYWLAHKALCSEKLDQWLCEK
L*GGGGS*DYKDDDDKDEL

INFORMAL SEQUENCE LISTING

Sequence ID No: 12 - cathelicidin-1 nucleic acid sequence with optional C-terminal linker in italics, C-terminal flag tag single underlined, and C-terminal KDEL ER retention sequence double underlined for expression in the nuclear genome CAGGCCCTGAGCTACCGCGAGGCCGTGCTGCGCGCCGTGGACCAGCTGAACGAGCAGAGCA
GCGAGCCCAACATCTACCGCCTGCTGGAGCTGGACCAGCCCCCCCAGGACGACGAGGACCC
CGACAGCCCCAAGCGCGTGTCCTTCCGCGTGAAGGAGACCGTGTGCAGCCGCACCACCCAG
CAGCCCCCCGAGCAGTGCGACTTCAAGGAGAACGGCCTGCTGAAGCGCTGCGAGGGCACCG
TGACCCTGGACCAGGTGCGCGGCAACTTCGACATCACCTGCAACAACCACCAGAGCATCCG
CATCACCAAGCAGCCGTGGGCCCCCCCGCAGGCCGCCCGCCTGTGCCGCATCGTCGTGATC
CGCGTGTGCCGC*ggcggcggaggatcc*<u>GACTACAAGGACGACGACGACAAG</u><u><u>GACGAGCTC</u></u>

Sequence ID No: 13 - cathelicidin-1 amino acid sequence with optional C-terminal linker in italics, C-terminal flag tag single underlined, and C-terminal KDEL ER retention sequence double underlined for expression in the nuclear genome QALSYREAVLRAVDQLNEQSSEPNIYRLLELDQPPQDDEDPDSPKRVSFRVKETVCSRTTQ
QPPEQCDFKENGLLKRCEGTVTLDQVRGNFDITCNNHQSIRITKQPWAPPQAARLCRIVVI
RVCR*GGGGS*<u>DYKDDDDK</u><u><u>KDEL</u></u>

Sequence ID No: 14 - lingual antimicrobial peptide nucleic acid sequence with optional C-terminal linker in italics, C-terminal flag tag single underlined, and C-terminal KDEL ER retention sequence double underlined for expression in the nuclear genome GTGCGCAACAGCCAGAGCTGCCGCCGCAACAAGGGCATCTGCGTGCCCATCCGCTGCCCCG
GCAGCATGCGCCAGATCGGCACCTGCCTGGGCGCCCAGGTGAAGTGCTGCCGCCGCAAG*gg
cggcggaggatcc*<u>GACTACAAGGACGACGACGAC</u><u><u>AAGGACGAGCTC</u></u>

Sequence ID No: 15 - lingual antimicrobial peptide amino acid sequence with optional C-terminal linker in italics, C-terminal flag tag single underlined, and C-terminal KDEL ER retention sequence double underlined for expression in the nuclear genome VRNSQSCRRNKGICVPIRCPGSMRQIGTCLGAQVKCCRRK*GGGGS*<u>DYKDDDDK</u><u><u>KDEL</u></u>

Sequence ID No: 16 - soluble CD14 nucleic acid sequence with optional C-terminal linker in italics, C-terminal flag tag single underlined, and C-terminal KDEL ER retention sequence double underlined for expression in the nuclear genome GACACCACCGAGCCCTGCGAGCTGGACGACGACGACTTCCGCTGCGTGTGCAACTTCACCG
ACCCCAAGCCCGACTGGTCCAGCGCCGTGCAGTGCATGGTGGCCGTGGAGGTGGAGATCAG
CGCCGGCGGCCGCAGCCTGGAGCAGTTCCTGAAGGGCGCGGACACCAACCCGAAGCAGTAC
GCCGACACCATCAAGGCGCTGCGCGTGCGCCGCCTGAAGCTGGGCGCGGCCCAGGTGCCCG
CGCAGCTGCTGGTGGCGGTGCTGCGCGCCCTGGGCTACTCGCGCCTGAAGGAGCTGACCCT
GGAGGACCTGGAGGTGACCGGCCCCACCCCCCCGACCCCCCTGGAGGCCGCGGGCCCCGCC
CTGACCACCCTGAGCCTGCGCAACGTGTCCTGGACCACCGGCGCGCCTGGCTGGGCGAGC
TGCAGCAGTGGCTGAAGCCCGGCCTGCGCGTGCTGAACATCGCCCAGGCCCACAGCCTGGC
CTTCCCCGTGCGCGGGCCTGAGCACCTTCGAGGCGCTGACCACCCTGGACCTGAGCGACAAC
CCCTCGCTGGGCGACAGCGGCCTGATGGCCGCCCTGTGCCCCAACAAGTTCCCCGCGCTGC
AGTACCTGGCGCTGCGCAACGCCGGCATGGAGACCCCCAGCGGCGTGTGCGCCGCGCTGGC
CGCCGCCCGCGTGCAGCCCCAGTCGCTGGACCTGTCCCACAACTCCCTGCGCGTGACCGCG
CCCGGCGCCACCCGCTGCGTGTGGCCCAGCGCCCTGCGCAGCCTGAACCTGAGCTTCGCCG
GCCTGGAGCAGGTGCCCAAGGGCCTGCCCCCCAAGCTGAGCGTGCTGGACCTGAGCTGCAA
CAAGCTGAGCCGCGAGCCGCGCCGCGACGAGCTGCCCGAGGTGAACGACCTGACCCTGGAC
GGCAACCCCTTCCTGGACCCGGGCGCCCTGCAGCACCAGAACGACCCCATGATCTCCGGCG
TGGTGCCCGCCTGCGCCCGCTCGGCCCTGACCATGGGCGTGTCGGGCGCGCTGGCCCTGCT
GCAGGGCGCGCGCGGCTTCGCC*ggcggcggaggatcc*<u>GACTACAAGGACGACGACGACAAG
GACGAGCTC</u>

Sequence ID No: 17 - soluble CD14 amino acid sequence with optional C-terminal linker in italics, C-terminal flag tag single underlined, and C-terminal KDEL ER retention sequence double underlined for expression in the nuclear genome DTTEPCELDDDDFRCVCNFTDPKPDWSSAVQCMVAVEVEISAGGRSLEQFLKGADTNPKQY
ADTIKALRVRRLKLGAAQVPAQLLVAVLRALGYSRLKELTLEDLEVTGPTPPTPLEAAGPA
LTTLSLRNVSWTTGGAWLGELQQWLKPGLRVLNIAQAHSLAFPCAGLSTFEALTTLDLSDN
PSLGDSGLMAALCPNKFPALQYLALRNAGMETPSGVCAALAAARVQPQSLDLSHNSLRVTA
PGATRCVWPSALRSLNLSFAGLEQVPKGLPPKLSVLDLSCNKLSREPRRDELPEVNDLTLD
GNPFLDPGALQHQNDPMISGVVPACARSALTMGVSGALALLQGARGFA*GGGGS*<u>DYKDDDDK</u>
<u>DEL</u>

Sequence ID No: 18 - mammary associated serum amyloid A3 nucleic acid sequence for expression in the nuclear genome ATGTGGGGCACCTTCCTGAAGGAGGCGGGCCAGGGCGCGAAGGACATGTGGCGCGCCTACC
AGGACATGAAGGAGGCCAACTACCGCGGCGCGGACAAGTACTTCCACGCCCGCGGCAACTA

```
CGACGCGGCCCGCCGCGGCCCCGGCGGCGCGTGGGCGGCGAAGGTGATCAGCAACGCGCGC
GAGACCATCCAGGGCATCACCGACCCCTGTTCAAGGGCATGACCCGCGACCAGGTGCGCG
AGGACAGCAAGGCCGACCAGTTCGCGAACGAGTGGGGCCGCAGCGGCAAGGACCCCAACCA
CTTCCGCCCCGCGGGCCTGCCCGACAAGTAC
```

Sequence ID No: 19 - mammary associated serum amyloid A3
amino acid sequence for expression in the nuclear genome
```
MWGTFLKEAGQGAKDMWRAYQDMKEANYRGADKYFHARGNYDAARRGPGGAWAAKVISNAR
ETIQGITDPLFKGMTRDQVREDSKADQFANEWGRSGKDPNHFRPAGLPDKY
```

Sequence ID No: 20 - osteopontin nucleic acid sequence for
expression in the chloroplast genome
```
AGTTTACCTGTAAAACCAACATCATCAGGTTCATCAGAAGAAAAACAATTAAATAATAAAT
ATCCAGATGCTGTTGCAATTTGGTTAAAACCTGATCCATCACAAAAACAAACATTTTTAAC
ACCACAAAATTCAGTATCATCAGAAGAAACAGATGATAATAAACAAAATACATTACCATCA
AAATCAAATGAATCACCAGAACAAACTGATGATTTAGATGATGATGATAATTCACAAG
ATGTTAATTCAAATGATTCAGATGATGCTGAAACAACAGATGATCCTGATCATTCAGATGA
ATCACATCACTCAGATGAATCAGATGAAGTTGATTTTCCTACAGATATTCCAACTATTGCT
GTTTTTACACCATTTATTCCTACAGAATCAGCTAATGATGGTCGTGGTGATTCAGTAGCTT
ATGGTTTAAAATCACGTTCAAAAAAATTTCGTCGTTCAAATGTACAATCACCAGATGCTAC
TGAAGAAGATTTCACATCACACATTGAATCAGAAGAAATGCACGATGCTCCAAAAAAAACT
TCACAATTAACAGATCATTCAAAAGAAACTAATTCATCAGAATTATCAAAAGAATTAACAC
CAAAAGCTAAAGATAAAAATAAACATTCAAATTTAATTGAATCACAAGAAAATTCAAATT
ATCACAAGAATTTCATTCATTAGAAGATAAATTAGATTTAGATCACAAATCAGAAGAAGAT
AAACATTTAAAAATTCGTATTTCACATGAATTAGATTCAGCTTCATCAGAAGTTAAT
```

Sequence ID No: 21 - osteopontin nucleic acid sequence for
expression in the nuclear genome
```
CTGCCCGTGAAGCCCACCAGCAGCGGCAGCAGCGAGGAGAAGCAGCTGAACAACAAGTACC
CCGACGCCGTGGCCACCTGGCTGAAGCCCGACCCCAGCCAGAAGCAGACCTTCCTGGCCCC
CCAGAACAGCGTGTCCTCCGAGGAGACCGACGACAACAAGCAGAACACCCTGCCCAGCAAG
AGCAACGAGAGCCCGAGCAGACCGACGACCTGGACGACGACGACGACAACAGCAGGACG
TGAACAGCAACGACAGCGACGACGCCGAGACCACCGACGACCCCGACCACAGCGACGAGAG
CCACCACTCCGACGAGTCGGACGAGGTGGACTTCCCCACCGACATCCCCACCATCGCGGTG
TTCACCCCCTTCATCCCGACCGAGAGCGCCAACGACGGCCGCGGCGACAGCGTGGCCTACG
GCCTGAAGTCCCGCAGCAAGAAGTTCCGCCGCAGCAACGTGCAGTCGCCCGACGCCACCGA
GGAGGACTTCACCTCCCACATCGAGTCGGAGGAGATGCACGACGCCCCCAAGAAGACCAGC
CAGCTGACCGACCACTCCAAGGAGACCAACAGCTCCGAGCTGAGCAAGGAGCTGACCCCCA
AGGCCAAGGACAAGAACAAGCACAGCAACCTGATCGAGAGCCAGGAGAACAGCAAGCTGTC
CCAGGAGTTCCACAGCCTGGAGGACAAGCTGGACCTGGACCACAAGAGCGAGGAGGACAAG
CACCTGAAGATCCGCATCAGCCACGAGCTGGACAGCGCCTCCAGCGAGGTGAAC
```

Sequence ID No: 22 - osteopontin amino acid sequence
The N-terminal methionine (M) is optionally absent.
```
MLPVKPTSSGSSEEKQLNNKYPDAVAIWLKPDPSQKQTFLTPQNSVSSEETDDNKQNTLPS
KSNESPEQTDDLDDDDDNSQDVNSNDSDDAETTDDPDHSDESHHSDESDEVDFPTDIPTIA
VFTPFIPTESANDGRGDSVAYGLKSRSKKFRRSNVQSPDATEEDFTSHIESEEMHDAPKKT
SQLTDHSKETNSSELSKELTPKAKDKNKHSNLIESQENSKLSQEFHSLEDKLDLDHKSEED
KHLKIRISHELDSASSEVN
```

Sequence ID No: 23 - lactadherin nucleic acid sequence for
expression in the nuclear genome
```
TTCAGCGGCGACTTCTGCGACAGCAGCCAGTGCCTGCACGGCGGCACCTGCCTGCTGAACG
AGGACCGCACCCCCCCCTTCTACTGCCTGTGCCCCGAGGGCTTCACCGGCCTGCTGTGCAA
CGAGACCGAGCACGGCCCCTGCTTCCCCAACCCCTGCCACAACGACGCCGAGTGCCAGGTG
ACCGACGACAGCCACCGCGGCGACGTGTTCATCCAGTACATCTGCAAGTGCCCCCTGGGCT
ACGTGGGCATCCACTGCGAGACCACCTGCACCTCGCCCCTGGGCATGCAGACCGGCGCGAT
CGCCGACAGCCAGATCAGCGCCAGCAGCATGCACCTGGGCTTCATGGGCCTGCAGCGCTGG
GCCCCCGAGCTGGCCCGCCTGCACCAGACCGGCATCGTGAACGCCTGGACCAGCGGCAACT
ACGACAAGAACCCGTGGATTCAGGTGAACCTGATGCGCAAGATGTGGGTCACCGGCGTCGT
GACCCAGGGCGCCAGCCGCGCCGGCAGCGCCGAGTACCTGAAGACCTTCAAGGTGGCCTAC
AGCACCGACGGCCGCCAGTTCCAGTTCATCCAGGTGGCCGGCCGCAGCGGCGACAAGATCT
TCATCGGCAACGTGAACAACTCCGGCCTGAAGATCAACCTGTTCGACACCCCCCTGGAGAC
CCAGTACGTGCGCCTGGTGCCCATCATCTGCCACCGCGGCTGCACCCTGCGCTTCGAGCTG
CTGGGCTGCGAGCTGAACGGCTGCACCGAGCCGCTGGGCCTGAAGGACAACACCATCCCCA
ACAAGCAGATCACCGCCTCCAGCTACTACAAGACCTGGGGCCTGAGCGCCTTCTCCTGGTT
CCCCTACTACGCCCGCCTGGACAACCAGGGCAAGTTCAACGCGTGGACCGCCCAGACCAAC
AGCGCCTCCGAGTGGCTGCAGATCGACCTGGGCAGCCAGAAGCGCGTGACCGGCATCATCA
CCCAGGGCGCGCGCGACTTCGGCCACATCCAGTACGTGGCCGCCTACCGCGTGGCCTACGG
CGACGACGGCGTGACCTGGACCGAGTACAAGGACCCCGGCGCCAGCGAGAGCAAGATCTTC
CCGGGCAACATGGACAACAACAGCCACAAGGAAGAACATCTTCGAGACCCCCTTCCAGGCCC
GCTTCGTGCGCATCCAGCCCGTGGCCTGGCACAACCGCATCACCCTGCGCGTGGAGCTGCT
GGGCTGC
```

Sequence ID No: 24 - lactadherin amino acid sequence
```
FSGDFCDSSQCLHGGTCLLNEDRTPPFYCLCPEGFTGLLCNETEHGPCFPNPCHNDAECQV
TDDSHRGDVFIQYICKCPLGYVGIHCETTCTSPLGMQTGAIADSQISASSMHLGFMGLQRW
```

| INFORMAL SEQUENCE LISTING |
|---|
| APELARLHQTGIVNAWTSGNYDKNPWIQVNLMRKMWVTGVVTQGASRAGSAEYLKTFKVAY
STDGRQFQFIQVAGRSGDKIFIGNVNNSGLKINLFDTPLETQYVRLVPIICHRGCTLRFEL
LGCELNGCTEPLGLKDNTIPNKQITASSYYKTWGLSAFSWFPYYARLDNQGKFNAWTAQTN
SASEWLQIDLGSQKRVTGIITQGARDFGHIQYVAAYRVAYGDDGVTWTEYKDPGASESKIF
PGNMDNNSHKKNIFETPFQARFVRIQPVAWHNRITLRVELLGC

Sequence ID No: 25 - cathelicidin-1 nucleic acid sequence for
expression in the nuclear genome
CAGGCCCTGAGCTACCGCGAGGCCGTGCTGCGCGCCGTGGACCAGCTGAACGAGCAGAGCA
GCGAGCCCAACATCTACCGCCTGCTGGAGCTGGACCAGCCCCCCAGGACGACGAGGACCC
CGACAGCCCCAAGCGCGTGTCCTTCCGCGTGAAGGAGACCGTGTGCAGCCGCACCACCCAG
CAGCCCCCCGAGCAGTGCGACTTCAAGGAGAACGGCCTGCTGAAGCGCTGCGAGGGCACCG
TGACCCTGGACCAGGTGCGCGGCAACTTCGACATCACCTGCAACAACCACCAGAGCATCCG
CATCACCAAGCAGCCGTGGGCCCCCCCGCAGGCCGCCCGCCTGTGCCGCATCGTCGTGATC
CGCGTGTGCCGC Sequence ID No: 26 - cathelicidin-1 amino acid sequence
QALSYREAVLRAVDQLNEQSSEPNIYRLLELDQPPQDDEDPDSPKRVSFRVKETVCSRTTQ
QPPEQCDFKENGLLKRCEGTVTLDQVRGNFDITCNNHQSIRITKQPWAPPQAARLCRIVVI
RVCR*

Sequence ID No: 27 - bovine milk lysozyme nucleic acid
sequence for expression in the nuclear genome
AAGAAGTTCCAGCGCTGCGAGCTGGCCCGCACCCTGAAGAAGCTGGGCCTGGACGGCTACC
GCGGCGTGTCCCTGGCCAACTGGGTGTGCCTGGCCCGCTGGGAGAGCAACTACAACACCCG
CGCCACCAACTACAACCGCGGCGACAAGAGCACCGACTACGGCATCTTCCAGATCAACAGC
CGCTGGTGGTGCAACGACGGCAAGACCCCCAAGGCCGTGAACGCCTGCCGCATCCCCTGCA
GCGCCCTGCTGAAGGACGACATCACCCAGGCCGTGGCCTGCGCCAAGCGCGTCGTGCGCGA
CCCCCAGGGCATCAAGGCGTGGGTGGCGTGGCGCAACAAGTGCCAGAACCGCGACCTGCGC
AGCTACGTGCAGGGCTGCCGCGTG Sequence ID No: 28 - bovine milk lysozyme amino acid sequence
KKFQRCELARTLKKLGLDGYRGVSLANWVCLARWESNYNTRATNYNRGDKSTDYGIFQINS
RWWCNDGKTPKAVNACRIPCSALLKDDITQAVACAKRVVRDPQGIKAWVAWRNKCQNRDLR
SYVQGCRV Sequence ID No: 29 - alpha-lactalbumin nucleic acid sequence
for expression in the nuclear genome
GAGCAGCTGACCAAGTGCGAGGTGTTCCGCGAGCTGAAGGACCTGAAGGGCTACGGCGGCG
TGTCGCTGCCCGAGTGGGTGTGCACCACCTTCCACACCAGCGGCTACGACACCCAGGCGAT
CGTGCAGAACAACGACAGCACCGAGTACGGCCTGTTCCAGATCAACAACAAGATCTGGTGC
AAGGACGACCAGAACCCCCACAGCAGCAACATCTGCAACATCAGCTGCGACAAGTTCCTGG
ACGACGACCTGACCGACGACATTATGTGCGTGAAGAAGATCCTGGACAAGGTGGGCATCAA
CTACTGGCTGGCCCACAAGGCCCTGTGCAGCGAGAAGCTGGACCAGTGGCTGTGCGAGAAG
CTG Sequence ID No: 30 - alpha-lactalbumin amino acid sequence
EQLTKCEVFRELKDLKGYGGVSLPEWVCTTFHTSGYDTQAIVQNNDSTEYGLFQINNKIWC
KDDQNPHSSNICNISCDKFLDDDLTDDIMCVKKILDKVGINYWLAHKALCSEKLDQWLCEK
L Sequence ID No: 31 - lingual antimicrobial peptide nucleic
acid sequence for expression in the nuclear genome
GTGCGCAACAGCCAGAGCTGCCGCCGCAACAAGGGCATCTGCGTGCCCATCCGCTGCCCCG
GCAGCATGCGCCAGATCGGCACCTGCCTGGGCGCCCAGGTGAAGTGCTGCCGCCGCAAG Sequence ID No: 32 - lingual antimicrobial peptide amino acid
sequence
VRNSQSCRRNKGICVPIRCPGSMRQIGTCLGAQVKCCRRK Sequence ID No: 33 - soluble CD14 nucleic acid sequence for
expression in the nuclear genome
GACACCACCGAGCCCTGCGAGCTGGACGACGACGACTTCCGCTGCGTGTGCAACTTCACCG
ACCCCAAGCCCGACTGGTCCAGCGCCGTGCAGTGCATGGTGGCCGTGGAGGTGGAGATCAG
CGCCGGCGGCCGCAGCCTGGAGCAGTTCCTGAAGGGCGCGGACACCAACCCGAAGCAGTAC
GCCGACACCATCAAGGCGCTGCGCGTGCGCCGCCTGAAGCTGGGCGCGGCCCAGGTGCCCG
CGCAGCTGCTGGTGGCGGTGCTGCGCGCCCTGGGCTACTCGCGCCTGAAGGAGCTGACCCT
GGAGGACCTGGAGGTGACCGGCCCCACCCCCCGACCCCCTGGAGGCCGCGGGCCCCGCC
CTGACCACCCTGAGCCTGCGCAACGTGTCCTGGACCACCGGCGGCGCCTGGCTGGGCGAGC
TGCAGCAGTGGCTGAAGCCCGGCCTGCGCGTGCTGAACATCGCCCAGGCCCACAGCCTGGC
CTTCCCGTGCGCGGGCCTGAGCACCTTCGAGGCGCTGACCACCCTGGACCTGAGCGACAAC
CCCTCGCTGGGCGACAGCGGCCTGATGGCCGCCCTGTGCCCCAACAAGTTCCCCGCGCTGC
AGTACCTGGCGCTGCGCAACGCCGGCATGGAGACCCCCAGCGGCGTGTGCGCCGCGCTGGC
CGCCGCCCGCGTGCAGCCCCAGTCGCTGGACCTGTCCCACAACTCCCTGCGCGTGACCGCG
CCCGGCGCCACCCGCTGCGTGTGGCCCAGCGCCCTGCGCAGCCTGAACCTGAGCTTCGCCG
GCCTGGAGCAGGTGCCCAAGGGCCTGCCCCCCAAGCTGAGCGTGCTGGACCTGAGCTGCAA
CAAGCTGAGCCGCGAGCCGCGCCGCGACGAGCTGCCCGAGGTGAACGACCTGACCCTGGAC |

INFORMAL SEQUENCE LISTING

```
GGCAACCCCTTCCTGGACCCGGGCGCCCTGCAGCACCAGAACGACCCCATGATCTCCGGCG
TGGTGCCCGCCTGCGCCCGCTCGGCCCTGACCATGGGCGTGTCGGGCGCGCTGGCCCTGCT
GCAGGGCGCGCGCGGCTTCGCC
```

Sequence ID No: 34 - soluble CD14 amino acid sequence
```
DTTEPCELDDDDFRCVCNFTDPKPDWSSAVQCMVAVEVEISAGGRSLEQFLKGADTNPKQY
ADTIKALRVRRLKLGAAQVPAQLLVAVLRALGYSRLKELTLEDLEVTGPTPPTPLEAAGPA
LTTLSLRNVSWTTGGAWLGELQQWLKPGLRVLNIAQAHSLAFPCAGLSTFEALTTLDLSDN
PSLGDSGLMAALCPNKFPALQYLALRNAGMETPSGVCAALAAARVQPQSLDLSHNSLRVTA
PGATRCVWPSALRSLNLSFAGLEQVPKGLPPKLSVLDLSCNKLSREPRRDELPEVNDLTLD
GNPFLDPGALQHQNDPMISGVVPACARSALTMGVSGALALLQGARGFA
```

Sequence ID No: 35 - gamma zein (Zera) amino acid sequence for increased protein accumulation
```
MRVLLVALALLLALAASATSTHTSGGCGCQPPPPVHLPPPVHLPPPVHLPPPVHLPPPVHLP
PPVHLPPPVHVPPPVHLPPPPCHYPTQPPRPQPHPQHPCPCQQPHPSPCQ
```

Sequence ID No: 36 - hydrophobin (HBN1) amino acid sequence for increased protein accumulation
```
GSSNGNGNVCPPGLFSNPQCCATQVLGLIGLDCKVPSQNVYDGTDFRNVCAKTGAQPLCCV
APVAGQALLCQTAVGA
```

Sequence ID No: 37 - lactoperoxidase nucleic acid sequence with optional C-terminal linker in italics, C-terminal flag tag single underlined, and C-terminal KDEL ER retention sequence double underlined for expression in the nuclear genome
```
GACACCACCCTGACCAACGTGACCGACCCCAGCCTGGACCTGACCGCCCTGAGCTGGGAGG
TGGGCTGCGGCGCCCCCGTGCCCCTGGTCAAGTGCGACGAGAACAGCCCCTACCGCACCAT
CACCGGCGACTGCAACAACCGCCGCTCCCCCGCCCTGGGCGCCGCCAACCGCGCCCTGGCC
CGCTGGCTGCCCGCCGAGTACGAGGACGGCCTGGCCCTGCCCTTCGGCTGGACCCAGCGCA
AGACCCGCAACGGCTTCCGCGTGCCGCTGGCCCGCGAGGTGTCCAACAAGATCGTGGGCTA
CCTGGACGAGGAGGGCGTGCTGGACCAGAACCGCAGCCTGCTGTTCATGCAGTGGGGCCAG
ATCGTGGACCACGACCTGGACTTCGCCCCCGAGACCGAGCTGGGCAGCAACGAGCACAGCA
AGACCCAGTGCGAGGAGTACTGCATCCAGGGCGACAACTGCTTCCCCATCATGTTCCCCAA
GAACGACCCCAAGCTGAAGACCCAGGGCAAGTGCATGCCGTTCTTCCGCGCCGGCTTCGTG
TGCCCCACCCCCCCGTACCAGAGCCTGGCGCGCGAGCAGATCAACGCCGTGACCTCGTTCC
TGGACGCCAGCCTGGTGTACGGCAGCGAGCCCTCCCTGGCCTCCCGCCTGCGCAACCTGTC
CAGCCCCCTGGGCCTGATGGCCGTGAACCAGGAGGCCTGGGACCACGGCCTGGCCTACCTG
CCCTTCAACAACAAGAAGCCCAGCCCCTGCGAGTTCATCAACACCACCGCCCGCGTGCCCT
GCTTCCTGGCGGGCGACTTCCGCGCGTCGGAGCAGATCCTGCTGGCCACCGCCCACACCCT
GCTGCTGCGCGAGCACAACCGCCTGGCCCGCGAGCTGAAGAAGCTGAACCCCCACTGGAAC
GGCGAGAAGCTGTACCAGGAGGCGCGCAAGATCCTGGGCGCCTTCATCCAGATCATCACCT
TCCGCGACTACCTGCCCGATCGTGCTGGGCTCCGAGATGCAGAAGTGGATTCCGCCCTACCA
GGGCTACAACAACAGCGTGGACCCCGCATCAGCAACGTGTTCACCTTCGCCTTCCGCTTC
GGCCACATGGAGGTGCCCAGCACCGTGTCCCGCCTGGACGAGAACTACCAGCCCTGGGGCC
CCGAGGCGGAGCTGCCCCTGCACACCCTGTTCTTCAACACCTGGCGCATCATCAAGGACGG
CGGCATCGACCCCCTGGTGCGCGGCCTGCTGGCGAAGAAGTCCAAGCTGATGAACCAGGAC
AAGATGGTCACCAGCGAGCTGCGCAACAAGCTGTTCCAGCCCACCCACAAGATCCACGGCT
TCGACCTGGCCGCCATCAACCTGCAGCGCTGCCGCGACCACGGCATGCCCGGCTACAACTC
GTGGCGCGGCTTCTGCGGCCTGAGCCAGCCCAAGACCCTGAAGGGCCTGCAGACCGTGCTG
AAGAACAAGATCCTGGCCAAGAAGCTGATGGACCTGTACAAGACCCCCGACAACATCGACA
TCTGGATCGGCGGCAACGCCGAGCCCATGGTGGAGCGCGGCCGCGTGGGCCCGCTGCTGGC
CTGCCTGCTGGGCCGCCAGTTCCAGCAGATCCGCGACGGCGACCGCTTCTGGTGGGAGAAC
CCCGGCGTGTTCACCGAGAAGCAGCGCGACAGCCTGCAGAAGGTGTCCTTCAGCCGCCTGA
TCTGCGACAACACCCACATCACCAAGGTGCCGCTGCACGCCTTCCAGGCCAACAACTACCC
CCACGACTTCGTGGACTGCTCCACCGTGGACAAGCTGGACCTGTCCCCGTGGGCCAGCCGC
GAGAACggatccGACTACAAGGACGACGACGACAAGGACGAGCTC
```

Sequence ID No: 38 - lactoperoxidase amino acid sequence with optional C-terminal linker in italics, C-terminal flag tag single underlined, and C-terminal KDEL ER retention sequence double underlined for expression in the nuclear genome
```
DTTLTNVTDPSLDLTALSWEVGCGAPVPLVKCDENSPYRTITGDCNNRRSPALGAANRALA
RWLPAEYEDGLALPFGWTQRKTRNGFRVPLAREVSNKIVGYLDEEGVLDQNRSLLFMQWGQ
IVDHDLDFAPETELGSNEHSKTQCEEYCIQGDNCFPIMFPKNDPKLKTQGKCMPFFRAGFV
CPTPPYQSLAREQINAVTSFLDASLVYGSEPSLASRLRNLSSPLGLMAVNQEAWDHGLAYL
PFNNKKPSPCEFINTTARVPCFLAGDFRASEQILLATAHTLLLREHNRLARELKKLNPHWN
GEKLYQEARKILGAFIQIITFRDYLPIVLGSEMQKWIPPYQGYNNSVDPRISNVFTFAFRF
GHMEVPSTVSRLDENYQPWGPEAELPLHTLFFNTWRIIKDGGIDPLVRGLLAKKSKLMNQD
KMVTSELRNKLFQPTHKIHGFDLAAINLQRCRDHGMPGYNSWRGFCGLSQPKTLKGLQTVL
KNKILAKKLMDLYKTPDNIDIWIGGNAEPMVERGRVGPLLACLLGRQFQQIRDGDRFWWEN
PGVFTEKQRDSLQKVSFSRLICDNTHITKVPLHAFQANNYPHDFVDCSTVDKLDLSPWASR
ENGSDYKDDDDKDEL
```

INFORMAL SEQUENCE LISTING

Sequence ID No: 39 - lactoperoxidase nucleic acid sequence
for expression in the nuclear genome
GACACCACCCTGACCAACGTGACCGACCCCAGCCTGGACCTGACCGCCCTGAGCTGGGAGG
TGGGCTGCGGCGCCCCCGTGCCCTGGTCAAGTGCGACGAGAACAGCCCCTACCGCACCAT
CACCGGCGACTGCAACAACCGCCGCTCCCCCGCCCTGGGCGCCGCCAACCGCGCCCTGGCC
CGCTGGCTGCCCGCCGAGTACGAGGACGGCCTGGCCCTGCCCTTCGGCTGGACCCAGCGCA
AGACCCGCAACGGCTTCCGCGTGCCGCTGGCCCGCGAGGTGTCCAACAAGATCGTGGGCTA
CCTGGACGAGGAGGGCGTGCTGGACCAGAACCGCAGCCTGCTGTTCATGCAGTGGGGCCAG
ATCGTGGACCACGACCTGGACTTCGCCCCCGAGACCGAGCTGGGCAGCAACGAGCACAGCA
AGACCCAGTGCGAGGAGTACTGCATCCAGGGCGACAACTGCTTCCCCATCATGTTCCCCAA
GAACGACCCCAAGCTGAAGACCCAGGGCAAGTGCATGCCGTTCTTCCGCGCCGGCTTCGTG
TGCCCCACCCCCCCGTACCAGAGCCTGGCGCGCGAGCAGATCAACGCCGTGACCTCGTTCC
TGGACGCCAGCCTGGTGTACGGCAGCGAGCCCTCCCTGGCCTCCCGCCTGCGCAACCTGTC
CAGCCCCCTGGGCCTGATGGCCGTGAACCAGGAGGCCTGGGACCACGGCCTGGCCTACCTG
CCCTTCAACAACAAGAAGCCCAGCCCCTGCGAGTTCATCAACACCACCGCCCGCGTGCCCT
GCTTCCTGGCGGGCGACTTCCGCGCGTCGGAGCAGATCCTGCTGGCCACCGCCCACACCCT
GCTGCTGCGCGAGCACAACCGCCTGGCCCGCGAGCTGAAGAAGCTGAACCCCACTGGAAC
GGCGAGAAGCTGTACCAGGAGGCGCGCAAGATCCTGGGCGCCTTCATCCAGATCATCACCT
TCCGCGACTACCTGCCGATCGTGCTGGGCTCCGAGATGCAGAAGTGGATTCCGCCCTACCA
GGGCTACAACAACAGCGTGGACCCCGCATCAGCAACGTGTTCACCTTCGCCTTCCGCTTC
GGCCACATGGAGGTGCCCAGCACCGTGTCCCGCCTGGACGAGAACTACCAGCCCTGGGGCC
CCGAGGCGGAGCTGCCCCTGCACACCCTGTTCTTCAACACCTGGCGCATCATCAAGGACGG
CGGCATCGACCCCCTGGTGCGCGGCCTGCTGGCGAAGAAGTCCAAGCTGATGAACCAGGAC
AAGATGGTCACCAGCGAGCTGCGCAACAAGCTGTTCCAGCCCACCCACAAGATCCACGGCT
TCGACCTGGCCGCCATCAACCTGCAGCGCTGCCGCGACCACGGCATGCCCGGCTACAACTC
GTGGCGCGGCTTCTGCGGCCTGAGCCAGCCCAAGACCCTGAAGGGCCTGCAGACCGTGCTG
AAGAACAAGATCCTGGCCAAGAAGCTGATGGACCTGTACAAGACCCCCGACAACATCGACA
TCTGGATCGGCGGCAACGCCGAGCCCATGGTGGAGCGCGGCCGCGTGGGCCCGCTGCTGGC
CTGCCTGCTGGGCCGCCAGTTCCAGCAGATCCGCGACGGCGACCGCTTCGGTGGGAGAAC
CCCGGCGTGTTCACCGAGAAGCAGCGCGACAGCCTGCAGAAGGTGTCCTTCAGCCGCCTGA
TCTGCGACAACACCCACATCACCAAGGTGCCGCTGCACGCCTTCCAGGCCAACAACTACCC
CCACGACTTCGTGGACTGCTCCACCGTGGACAAGCTGGACCTGTCCCCGTGGGCCAGCCGC
GAGAAC

What is claimed is:

1. An isolated nucleus of a photosynthetic organism, wherein the nucleus is transformed with a polynucleotide encoding mammalian milk lactadherin, wherein the lactadherin polypeptide has at least about 90%, 95%, 96%, 97%, 98%, or 99% sequence identity to SEQ ID NO:24.

2. The nucleus of claim 1, wherein the nucleus is from a microalgae.

3. The nucleus of claim 1, wherein the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae).

4. The nucleus of claim 1, wherein the nucleus is from a Chlorophyta (green algae) nucleus.

5. The nucleus of claim 1, wherein the photosynthetic organism is selected from the group consisting of Chlamydomonas reinhardtii, Dunaliella salina, Haematococcus pluvialis, Chlorella vulgaris, Acutodesmus obliquus, and Scenedesmus dimorphus.

6. The nucleus of claim 4, wherein the green alga is selected from the group consisting of Chlamydomonas, Dunaliella, Haematococcus, Chlorella, and Scenedesmaceae.

7. The nucleus of claim 1, wherein the polynucleotide encoding mammalian milk lactadherin is integrated into the nuclear genome.

8. The nucleus of claim 1, wherein the mammalian milk lactadherin is from a mammal selected from the group consisting of bovine, ovine and caprine.

9. An isolated photosynthetic cell comprising the nucleus of claim 1.

10. An isolated cell from a photosynthetic organism, the cell transformed with a polynucleotide encoding mammalian milk lactadherin, wherein the lactadherin polypeptide has at least about 90%, 95%, 96%, 97%, 98%, or 99% sequence identity to SEQ ID NO:24.

11. The cell of claim 10, wherein the cell is from a cyanobacteria.

12. The cell of claim 10, wherein the mammalian milk lactadherin is from a mammal selected from the group consisting of bovine, ovine and caprine.

13. The cell of claim 10, wherein the polynucleotide encoding mammalian milk lactadherin is integrated into the nuclear genome of the cell.

14. The cell of claim 10, wherein the cell is intact and/or freeze-dried.

15. A photosynthetic organism comprising the cell of claim 10.

16. A method for producing mammalian milk lactadherin, comprising culturing the cell of claim 10 under conditions sufficient to produce milk lactadherin.

17. A composition edible by a mammal comprising a population of cells of claim 10.

18. The composition of claim 17, wherein the composition is selected from a beverage, a food, a feed, a food supplement and a nutraceutical.

19. The composition of claim 17, wherein the composition is selected from the group consisting of a compressed algal cake, an algal paste and an algal powder.

20. The composition of claim 17, wherein the composition is freeze-dried, lyophilized or spray-dried.

21. The nucleus of claim 1, wherein the polynucleotide encoding mammalian milk lactadherin has at least about 90%, 95%, 98%, or 99% sequence identity to SEQ ID NO:23.

22. The nucleus of claim 1, wherein the nucleus is from a higher plant selected from Brassicaceae, Solanaceae, Phaseoleae, *Zea* and Oryzeae.

23. The cell of claim 10, wherein the polynucleotide encoding mammalian milk lactadherin has at least about 90%, 95%, 98%, or 99% sequence identity to SEQ ID NO:23.

24. The cell of claim 10, wherein the cell is from a microalgae.

25. The cell of claim 10, wherein the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae).

26. The cell of claim 10, wherein the nucleus is from a Chlorophyta (green algae) nucleus.

27. The cell of claim 10, wherein the green alga is selected from the group consisting of *Chlamydomonas, Dunaliella, Haematococcus, Chlorella*, and Scenedesmaceae.

28. The cell of claim 10, wherein the photosynthetic organism is selected from the group consisting of *Chlamydomonas reinhardtii, Dunaliella salina, Haematococcus pluvialis, Chlorella vulgaris, Acutodesmus obliquus*, and *Scenedesmus dimorphus*.

29. The cell of claim 10, wherein the cell is from a higher plant selected from Brassicaceae, Solanaceae, Phaseoleae, *Zea* and Oryzeae.

30. The cell of claim 10, wherein the lactadherin polypeptide comprises an amino acid sequence that promotes retention in the endoplasmic reticulum.

31. The cell of claim 10, wherein the lactadherin polypeptide comprises an amino acid sequence that promotes secretion from the cell.

32. The cell of claim 31, wherein the amino acid sequence that promotes secretion from the cell comprises SEQ ID NO:45, SEQ ID NO:46 or SEQ ID NO:47.

33. A culture medium comprising a population of cells of claim 31.

34. The method of claim 16, further comprising purifying or isolating the milk lactadherin.

35. The method of claim 16, wherein the milk lactadherin is not purified or isolated.

* * * * *